US010221278B2

(12) United States Patent
Lee et al.

(10) Patent No.: US 10,221,278 B2
(45) Date of Patent: Mar. 5, 2019

(54) CATALYTIC CARBONYLATION CATALYSTS AND METHODS

(71) Applicant: Novomer, Inc., Ithaca, NY (US)

(72) Inventors: Han Lee, Ithaca, NY (US); Scott D. Allen, Ithaca, NY (US); Jay J. Farmer, Ithaca, NY (US); Geoff Coates, Lansing, NY (US)

(73) Assignee: Novomer, Inc., Boston, MA (US)

( * ) Notice: Subject to any disclaimer, the term of this patent is extended or adjusted under 35 U.S.C. 154(b) by 0 days.

(21) Appl. No.: 15/130,810

(22) Filed: Apr. 15, 2016

(65) Prior Publication Data
US 2017/0073463 A1 Mar. 16, 2017

Related U.S. Application Data

(63) Continuation of application No. 14/117,393, filed as application No. PCT/US2012/037675 on May 12, 2012, now Pat. No. 9,327,280.

(60) Provisional application No. 61/485,660, filed on May 13, 2011.

(51) Int. Cl.
| *B01J 31/12* | (2006.01) |
| *B01J 31/18* | (2006.01) |
| *C08G 63/82* | (2006.01) |
| *C07F 15/06* | (2006.01) |
| *C07F 5/06* | (2006.01) |
| *C07C 51/54* | (2006.01) |
| *C07D 487/22* | (2006.01) |
| *B01J 31/22* | (2006.01) |
| *C07D 305/08* | (2006.01) |
| *C07D 307/20* | (2006.01) |

(52) U.S. Cl.
CPC .......... *C08G 63/823* (2013.01); *B01J 31/183* (2013.01); *B01J 31/2217* (2013.01); *B01J 31/2243* (2013.01); *C07C 51/54* (2013.01); *C07D 305/08* (2013.01); *C07D 307/20* (2013.01); *C07D 487/22* (2013.01); *C07F 5/069* (2013.01); *C07F 15/065* (2013.01); *B01J 2231/34* (2013.01); *B01J 2531/025* (2013.01); *B01J 2531/0216* (2013.01); *B01J 2531/0252* (2013.01); *B01J 2531/16* (2013.01); *B01J 2531/22* (2013.01); *B01J 2531/26* (2013.01); *B01J 2531/31* (2013.01); *B01J 2531/32* (2013.01); *B01J 2531/33* (2013.01); *B01J 2531/46* (2013.01); *B01J 2531/62* (2013.01); *B01J 2531/72* (2013.01); *B01J 2531/821* (2013.01); *B01J 2531/822* (2013.01); *B01J 2531/824* (2013.01); *B01J 2531/842* (2013.01); *B01J 2531/845* (2013.01); *B01J 2531/847* (2013.01); *B01J 2540/42* (2013.01); *B01J 2540/54* (2013.01)

(58) Field of Classification Search
CPC .................................. B01J 31/12; B01J 31/18
USPC .................................. 502/161, 164; 544/64
See application file for complete search history.

(56) References Cited

U.S. PATENT DOCUMENTS

| 2,245,404 | A | 6/1941 | Kise et al. |
| 2,302,321 | A | 11/1942 | Hopff et al. |
| 2,469,704 | A | 5/1949 | Stone |
| 2,526,554 | A | 10/1950 | Gresham et al. |
| 3,002,017 | A | 9/1961 | Wearsch et al. |
| 3,326,938 | A | 6/1967 | Wagner |
| 3,418,338 | A | 12/1968 | Gilman et al. |
| 3,751,435 | A | 8/1973 | Van Der Ven et al. |
| 3,800,006 | A | 3/1974 | Katayama et al. |
| 4,026,967 | A | 5/1977 | Flexman, Jr. et al. |
| 4,081,253 | A | 3/1978 | Marion |
| 4,221,727 | A | 9/1980 | Tsang et al. |
| 4,590,293 | A | 5/1986 | Pascoe |
| 4,873,378 | A | 10/1989 | Murphy et al. |
| 5,096,470 | A | 3/1992 | Krishnamurthy |
| 5,198,578 | A | 3/1993 | Etzkorn et al. |
| 5,310,948 | A | 5/1994 | Drent et al. |
| 5,731,252 | A | 3/1998 | Warner et al. |
| 6,123,812 | A | 9/2000 | Bessling et al. |
| 6,147,126 | A | 11/2000 | DeGeorge et al. |
| 6,348,611 | B1 | 2/2002 | Lee et al. |
| 6,392,078 | B1 | 5/2002 | Ryu et al. |
| 6,492,535 | B1 | 12/2002 | Castiglioni et al. |
| 6,573,340 | B1 | 6/2003 | Khemani et al. |
| 6,773,578 | B1 | 8/2004 | O'Rear et al. |
| 6,852,865 | B2 * | 2/2005 | Coates .................. B01J 31/183 502/161 |

(Continued)

FOREIGN PATENT DOCUMENTS

| CN | 101362103 A | 2/2009 |
| CN | 103822811 A | 5/2014 |

(Continued)

OTHER PUBLICATIONS

Church, T.L. et al.: The mechanism of epoxide carbonylation by [lewis acid]+{Co(CO)4} catalysts. J. Am. Chem. Soc., vol. 128, pp. 10125-10133, 2006.*

(Continued)

*Primary Examiner* — Charanjit Aulakh
(74) *Attorney, Agent, or Firm* — Morrison & Foerster LLP

(57) ABSTRACT

In one aspect, the present invention provides catalysts for the carbonylation of heterocycles. The inventive catalysts feature metal-ligand complexes having cationic functional groups tethered to the ligand, wherein the tethered cationic groups are associated with anionic metal carbonyl species. The invention also provides methods of using the inventive catalysts to affect the ring opening carbonylation of epoxides.

30 Claims, No Drawings

(56) References Cited

U.S. PATENT DOCUMENTS

| | | |
|---|---|---|
| 6,916,951 B2 | 7/2005 | Tustin et al. |
| 7,304,172 B2 | 12/2007 | Coates et al. |
| 7,569,709 B2 | 8/2009 | Coates et al. |
| 7,754,899 B2 * | 7/2010 | Katsuki .................. C07B 53/00 548/961 |
| 8,247,520 B2 | 8/2012 | Allen et al. |
| 8,277,660 B2 | 10/2012 | Kimball et al. |
| 8,445,703 B2 | 5/2013 | Allen et al. |
| 8,470,956 B2 | 6/2013 | Allen et al. |
| 8,530,677 B2 | 9/2013 | Coates et al. |
| 8,604,155 B2 | 12/2013 | Allen et al. |
| 8,633,123 B2 | 1/2014 | Allen et al. |
| 8,796,475 B2 | 8/2014 | Allen et al. |
| 8,921,508 B2 | 12/2014 | Allen et al. |
| 8,946,109 B2 | 2/2015 | Allen et al. |
| 8,951,930 B2 | 2/2015 | Allen et al. |
| 8,956,989 B2 | 2/2015 | Allen et al. |
| 9,096,510 B2 | 8/2015 | Porcelli et al. |
| 9,156,803 B2 | 10/2015 | Allen et al. |
| 9,206,144 B2 | 12/2015 | Allen et al. |
| 9,327,280 B2 | 5/2016 | Lee et al. |
| 9,403,788 B2 | 8/2016 | Lee et al. |
| 9,493,391 B2 | 11/2016 | Allen et al. |
| 9,914,689 B2 | 3/2018 | Porcelli et al. |
| 2003/0098274 A1 | 5/2003 | Lee et al. |
| 2003/0162961 A1 | 8/2003 | Coates et al. |
| 2004/0102532 A1 | 5/2004 | Landis et al. |
| 2005/0014977 A1 | 1/2005 | Drent et al. |
| 2005/0196343 A1 | 9/2005 | Reddy et al. |
| 2005/0209411 A1 | 9/2005 | Nestler et al. |
| 2005/0222458 A1 | 10/2005 | Craciun et al. |
| 2005/0240032 A1 | 10/2005 | Luinstra et al. |
| 2006/0189833 A1 | 8/2006 | Powell et al. |
| 2007/0155984 A1 | 7/2007 | Sielcken et al. |
| 2007/0217965 A1 | 9/2007 | Johnson et al. |
| 2007/0225522 A1 | 9/2007 | Kobayashi et al. |
| 2007/0293695 A1 | 12/2007 | Zoeller et al. |
| 2009/0075295 A1 | 3/2009 | Lindsey |
| 2009/0124787 A1 | 5/2009 | Preishuber-Pflugl et al. |
| 2009/0173694 A1 | 7/2009 | Peinemann et al. |
| 2009/0178495 A1 | 7/2009 | Steigmiller et al. |
| 2009/0253934 A1 | 10/2009 | Ho et al. |
| 2009/0287000 A1 | 11/2009 | Coates et al. |
| 2009/0287280 A1 | 11/2009 | Wong et al. |
| 2009/0299032 A1 | 12/2009 | Allen |
| 2010/0145046 A1 | 6/2010 | Coates et al. |
| 2010/0323573 A1 | 12/2010 | Chu et al. |
| 2010/0323885 A1 | 12/2010 | Herfert et al. |
| 2011/0065894 A1 | 3/2011 | Allen |
| 2011/0226697 A1 | 9/2011 | McLellan et al. |
| 2011/0301027 A1 | 12/2011 | Bitis et al. |
| 2011/0319849 A1 | 12/2011 | Collias et al. |
| 2012/0108695 A1 | 5/2012 | Won et al. |
| 2012/0123137 A1 | 5/2012 | Allen et al. |
| 2012/0189861 A1 | 7/2012 | Matsumoto et al. |
| 2012/0202951 A1 | 8/2012 | Gartner et al. |
| 2013/0004454 A1 | 1/2013 | Weiss et al. |
| 2013/0072645 A1 | 3/2013 | Balduf et al. |
| 2013/0165670 A1 | 6/2013 | Allen et al. |
| 2013/0172524 A1 | 7/2013 | Farmer |
| 2013/0274697 A1 | 10/2013 | Godlewski et al. |
| 2013/0281715 A1 | 10/2013 | Allen et al. |
| 2013/0299417 A1 | 11/2013 | Luchinger et al. |
| 2014/0018570 A1 | 1/2014 | Pazicky et al. |
| 2014/0018574 A1 | 1/2014 | Raith et al. |
| 2014/0221702 A1 | 8/2014 | Weston et al. |
| 2014/0228538 A1 | 8/2014 | Allen et al. |
| 2014/0275575 A1 | 9/2014 | Allen et al. |
| 2014/0296522 A1 | 10/2014 | Lee et al. |
| 2014/0309399 A1 | 10/2014 | Porcelli et al. |
| 2014/0336354 A1 | 11/2014 | Job et al. |
| 2014/0343246 A1 | 11/2014 | Allen et al. |
| 2015/0005513 A1 | 1/2015 | Lee et al. |
| 2015/0141693 A1 | 5/2015 | Allen et al. |
| 2015/0232496 A1 | 8/2015 | Job et al. |
| 2015/0252145 A1 | 9/2015 | Allen et al. |
| 2015/0299083 A1 | 10/2015 | Porcelli et al. |
| 2015/0368394 A1 | 12/2015 | Allen |
| 2016/0016876 A1 | 1/2016 | Mahoney |
| 2016/0102040 A1 | 4/2016 | Allen et al. |
| 2016/0102068 A1 | 4/2016 | Allen et al. |
| 2016/0204465 A1 | 7/2016 | Mimura et al. |
| 2016/0288057 A1 | 10/2016 | Lapointe et al. |
| 2017/0029352 A1 | 2/2017 | Sookraj et al. |
| 2017/0080409 A1 | 3/2017 | Farmer et al. |
| 2017/0096407 A1 | 4/2017 | Sookraj |
| 2017/0107103 A1 | 4/2017 | Sookraj et al. |
| 2017/0145126 A1 | 5/2017 | Mahoney |
| 2017/0225157 A1 | 8/2017 | Lee |
| 2017/0247309 A1 | 8/2017 | Porcelli et al. |
| 2018/0016219 A1 | 1/2018 | Farmer et al. |
| 2018/0022677 A1 | 1/2018 | Sookraj |
| 2018/0029005 A1 | 2/2018 | Sookraj |
| 2018/0030014 A1 | 2/2018 | Sookraj et al. |
| 2018/0030015 A1 | 2/2018 | Farmer et al. |
| 2018/0030201 A1 | 2/2018 | Farmer et al. |
| 2018/0057619 A1 | 3/2018 | Sookraj |
| 2018/0094100 A1 | 4/2018 | Farmer et al. |

FOREIGN PATENT DOCUMENTS

| | | |
|---|---|---|
| EP | 0352850 A1 | 1/1990 |
| EP | 0441447 A1 | 8/1991 |
| EP | 0577206 A2 | 1/1994 |
| EP | 0705821 A1 | 4/1996 |
| EP | 1304321 A2 | 4/2003 |
| EP | 2325214 A1 | 5/2011 |
| FR | 2725446 A1 | 4/1996 |
| GB | 762138 A | 11/1956 |
| JP | 57-14596 A | 1/1982 |
| JP | 6-65223 A | 3/1994 |
| JP | 2003-183225 A | 7/2003 |
| JP | 2005-511753 A | 4/2005 |
| JP | 2006-500338 A | 1/2006 |
| JP | 2006-524213 A | 10/2006 |
| JP | 2009-169753 A | 7/2009 |
| JP | 2012-523421 A | 10/2012 |
| WO | 2002/09781 A2 | 2/2002 |
| WO | 2003/050154 A2 | 6/2003 |
| WO | 2004/089923 A1 | 10/2004 |
| WO | 2006/087556 A1 | 8/2006 |
| WO | 2010/022388 A2 | 2/2010 |
| WO | 2010/028362 A1 | 3/2010 |
| WO | 2010/118128 A1 | 10/2010 |
| WO | 2010/137974 A1 | 12/2010 |
| WO | 2011/123558 A1 | 10/2011 |
| WO | 2011/163133 A1 | 12/2011 |
| WO | 2011/163309 A2 | 12/2011 |
| WO | 2012/030619 A1 | 3/2012 |
| WO | 2012/037282 A2 | 3/2012 |
| WO | 2012/158573 A1 | 11/2012 |
| WO | 2013/012895 A1 | 1/2013 |
| WO | 2013/063191 A1 | 5/2013 |
| WO | 2013/067460 A1 | 5/2013 |
| WO | 2013/068846 A1 | 5/2013 |
| WO | 2013/090276 A1 | 6/2013 |
| WO | 2013/122905 A1 | 8/2013 |
| WO | 2013/126375 A1 | 8/2013 |
| WO | 2013/180659 A1 | 12/2013 |
| WO | 2013/185009 A1 | 12/2013 |
| WO | 2014/004858 A1 | 1/2014 |
| WO | 2014/008232 A2 | 1/2014 |
| WO | 2014/031811 A1 | 2/2014 |
| WO | 2015/085295 A2 | 6/2015 |
| WO | 2015/110321 A1 | 7/2015 |
| WO | 2015/138975 A1 | 9/2015 |
| WO | 2015/171372 A1 | 11/2015 |
| WO | 2015/184289 A1 | 12/2015 |
| WO | 2016/015019 A1 | 1/2016 |
| WO | 2016/130947 A1 | 8/2016 |
| WO | 2016/130977 A1 | 8/2016 |
| WO | 2016/130988 A1 | 8/2016 |
| WO | 2016/130993 A1 | 8/2016 |
| WO | 2016/130998 A1 | 8/2016 |

(56) References Cited

FOREIGN PATENT DOCUMENTS

| WO | 2016/131001 A1 | 8/2016 |
|---|---|---|
| WO | 2016/131003 A1 | 8/2016 |
| WO | 2016/131004 A1 | 8/2016 |
| WO | 2017/023777 A1 | 2/2017 |
| WO | 2017/023820 A1 | 2/2017 |
| WO | 2017/165344 A1 | 9/2017 |
| WO | 2017/165345 A1 | 9/2017 |
| WO | 2018/085251 A1 | 5/2018 |
| WO | 2018/085254 A1 | 5/2018 |

OTHER PUBLICATIONS

Gianneschi, N. C. et al.: A supramolecular approach to an allosteric catalyst. J. Am. Chem. Soc., vol. 125, pp. 10508-10509, 2003.*

International Preliminary Report on Patentability received for PCT Patent Application No. PCT/US2012/037675, dated Nov. 28, 2013, 10 pages.

Wilen et al., "Strategies in Optical Resolutions", Tetrahedron, vol. 33, 1977, pp. 2725-2736.

Extended European Search Report (includes Supplementary European Search Report and Search Opinion) received for European Patent Application No. 12786675.4, dated Mar. 18, 2015, 7 pages.

Getzler, et al., "Synthesis of β-Lactones: A Highly Active and Selective Catalyst for Epoxide Carbonylation", Journal of the American Chemical Society. vol. 124, No. 7, 2002, pp. 1174-1175.

International Search Report and Written Opinion received for PCT Patent Application No. PCT/US2012/037675, dated Aug. 9, 2012, 12 pages.

Kramer, et al., "Fluorinated Beta-Lactones and Poly(Beta-Hydroxyalkanoate)S: Synthesis via Epoxide Carbonylation vnd Ring-Opening Polymerization", Tetrahedron, vol. 64, No. 29, 2008, pp. 6973-6978.

Kramer, et al., "Practical Beta-Lactone Synthesis: Epoxide Carbonylation at 1 Atm", Organic Letters, vol. 8, No. 17, 2006, pp. 3709-3712.

Lee, et al., "Synthesis of Beta-Lactones by the Regioselective, Cobalt and Lewis Acid Catalyzed Carbonylation of Simple and Functionalized Epoxides", The Journal of Organic Chemistry, vol. 66, No. 16, 2001, pp. 5424-5426.

Mahadevan, et al., "[Lewis Acid]+[Co(C0)(4)]—Complexes: A Versatile Class of Catalysts for Carbonylative Ring Expansion of Epoxides and Aziridines", Angewandte Chemie International Edition, vol. 41, No. 15, 2002, pp. 2781-2784.

Non-Final Office Action received for U.S. Appl. No. 14/117,393, dated Jun. 2, 2015, 9 pages.

Notice of Allowance received for U.S. Appl. No. 14/117,393, dated Dec. 22, 2015, 7 pages.

Rowley, et al., "Catalytic Double Carbonylation of Epoxides to Succinic Anhydrides: Catalyst Discovery, Reaction Scope, and Mechanism", Journal of the American Chemical Society, vol. 129, 2007, pp. 4948-4960.

Schmidt, et al., "A Readily Synthesized and Highly Active Epoxide Carbonylation Catalyst Based on a Chromium Porphyrin Framework: Expanding the Range of Available Beta-Lactones", Organic Letters, vol. 6, No. 3, 2004, pp. 373-376.

Schmidt, et al., "Chromium(III) Octaethylporphyrinato Tetracarbonylcobaltate: A Highly Active, Selective, and Versatile Catalyst for Epoxide Carbonylation", Journal of the American Chemical Society, vol. 127, No. 32, 2005, pp. 11426-11435.

Ahmed et al., "Enantioselective Polymerization of Epoxides Using Biaryl-Linked Bimetallic Cobalt Catalysts: A Mechanistic Study", Journal of the American Chemical Society, vol. 135, 2013, pp. 18901-18911.

Coates et al., "Quantitative Ring-Closing Metathesis of Polyolefins", Journal of the American Chemical Society, vol. 118, 1996, pp. 229-230.

Diciccio et al., "Development of Highly Active and Regioselective Catalysts for the Copolymerization of Epoxides with Cyclic Anhydrides: An Unanticipated Effect of Electronic Variation", Journal of the American Chemical Society, vol. 138, 2016, pp. 7107-7113.

Diciccio et al., "Ring-Opening Copolymerization of Maleic Anhydride with Epoxides: A Chain-Growth Approach to Unsaturated Polyesters", Journal of the American Chemical Society, vol. 133, 2011, pp. 10724-10727.

Dunn et al., "Carbonylative Polymerization of Propylene Oxide: A Multicatalytic Approach to the Synthesis of Poly(3-Hydroxybutyrate)", Journal of the American Chemical Society, vol. 132, No. 33, 2010, pp. 11412-11413.

Fieser et al., "Mechanistic Insights into the Alternating Copolymerization of Epoxides and Cyclic Anhydrides Using a (Salph)AlCl and Iminium Salt Catalytic System", Journal of the American Chemical Society, vol. 139, 2017, pp. 15222-15231.

Ganji et al., "In Situ Generation of the Coates Catalyst: A Practical and Versatile Catalytic System for the Carbonylation of Meso-Epoxides", Organic Letters, vol. 13, No. 12, 2011, pp. 3142-3145.

Ganji et al., "In Situ Generation of the Coatescatalyst: a Practical and Versatile Catalytic System for the Carbonylation of Meso-Epoxides", ChemInform Abstract, vol. 42, No. 39, 2011, 1 page.

Getzler et al., "Catalytic Carbonylation of β-Lactones to Succinic Anhydrides", Journal of the American Chemical Society, vol. 126, No. 22, 2004, pp. 6842-6843.

Hirahata et al., "Enantioselective Polymerization of Epoxides: A Highly Active and Selective Catalyst for the Preparation of Stereoregular Polyethers and Enantiopure Epoxides", Journal of the American Chemical Society, vol. 130, No. 52, 2008, pp. 17658-17659.

International Search Report and Written Opinion received for PCT Patent Application No. PCT/US11/49125, dated Jan. 11, 2012, 10 pages.

International Search Report and Written Opinion received for PCT Patent Application No. PCT/US13/25683, dated Apr. 23, 2013, 8 pages.

International Search Report and Written Opinion received for PCT Patent Application No. PCT/US17/23302, dated Jun. 5, 2017, 9 pages.

International Search Report and Written Opinion received for PCT Patent Application No. PCT/US17/23303, dated Jun. 7, 2017, 18 pages.

International Search Report and Written Opinion received for PCT Patent Application No. PCT/US2010/030230, dated Jun. 10, 2010, 17 pages.

International Search Report and Written Opinion received for PCT Patent Application No. PCT/US2012/061791, dated Feb. 8, 2013, 10 pages.

International Search Report and Written Opinion received for PCT Patent Application No. PCT/US2013/026810, dated Apr. 30, 2013, 8 pages.

International Search Report and Written Opinion received for PCT Patent Application No. PCT/US2013/048238, dated Dec. 3, 2013, 8 pages.

International Search Report and Written Opinion received for PCT Patent Application No. PCT/US2013/049026, dated Dec. 17, 2013, 9 pages.

International Search Report and Written Opinion received for PCT Patent Application No. PCT/US2014/069066, dated Mar. 16, 2015, 10 pages.

International Search Report and Written Opinion received for PCT Patent Application No. PCT/US2015/020562, dated Jun. 18, 2015, 9 pages.

International Search Report and Written Opinion received for PCT Patent Application No. PCT/US2015/028123, dated Jul. 23, 2015, 7 pages.

International Search Report and Written Opinion received for PCT Patent Application No. PCT/US2015/033232, dated Aug. 19, 2015, 8 pages.

International Search Report and Written Opinion received for PCT Patent Application No. PCT/US2015/042124, dated Dec. 15, 2015, 14 pages.

International Search Report and Written Opinion received for PCT Patent Application No. PCT/US2016/017797, dated May 5, 2016, 9 pages.

International Search Report and Written Opinion received for PCT Patent Application No. PCT/US2016/017844, dated May 6, 2016, 10 pages.

(56) References Cited

OTHER PUBLICATIONS

International Search Report and Written Opinion received for PCT Patent Application No. PCT/US2016/017861, dated Apr. 29, 2016, 25 pages.
International Search Report and Written Opinion received for PCT Patent Application No. PCT/US2016/017868, dated May 2, 2016, 9 pages.
International Search Report and Written Opinion received for PCT Patent Application No. PCT/US2016/017875, dated May 6, 2016, 16 pages.
International Search Report and Written Opinion received for PCT Patent Application No. PCT/US2016/017878, dated May 2, 2016, 9 pages.
International Search Report and Written Opinion received for PCT Patent Application No. PCT/US2016/017880, dated Apr. 29, 2016, 9 pages.
International Search Report and Written Opinion received for PCT Patent Application No. PCT/US2016/017881, dated May 2, 2016, 8 pages.
International Search Report and Written Opinion received for PCT Patent Application No. PCT/US2016/044772, dated Nov. 8, 2016, 17 pages.
International Search Report and Written Opinion received for PCT Patent Application No. PCT/US2016/044927, dated Nov. 8, 2016, 17 pages.
International Search Report and Written Opinion received for PCT Patent Application No. PCT/US2017/059243, dated Feb. 1, 2018, 10 pages.
International Search Report and Written Opinion received for PCT Patent Application No. PCT/US2017/059249, dated Feb. 22, 2018, 11 pages.
International Search Report and Written Opinion received for PCT Patent Application No. PCT/US2018/014243, dated Mar. 28, 2018, 11 pages.
Jeske et al., "Alternating Copolymerization of Epoxides and Cyclic Anhydrides: An Improved Route to Aliphatic Polyesters", Journal of the American Chemical Society, vol. 129, No. 37, 2007, pp. 11330-11331.
Kramer et al., "Carbonylation of Epoxides to Substituted 3-Hydroxy-δ-Lactones", Organic Letters, vol. 9, No. 26, 2007, pp. 5581-5583.
Lamb et al., "Regioselective Isomerization of 2,3-Disubstituted Epoxides to Ketones: An Alternative to the Wacker Oxidation of Internal Alkenes", Journal of the American Chemical Society, vol. 137, 2015, pp. 15049-15054.
Rieth et al., "Single-Site β-Diiminate Zinc Catalysts for the Ring-Opening Polymerization of β-Butyrolactone and β-Valerolactone to Poly(3-Hydroxyalkanoates).", Journal of the American Chemical Society, vol. 124, No. 51, 2002, pp. 15239-15248.
Slowik et al., "Catalytic Conversion of Waste Carbon Monoxide to Valuable Chemicals & Materials", Clean Technology, 2010, pp. 283-286.
Stanghellini et al., "Redox Reactions of Metal Carbonyls. I. Kinetics and Mechanism of Disproportionation of $Co_2(Co)_8$ with Piperidine", Inorganica Chimica Acta, vol. 22, 1977, pp. 19-22.
Thomas et al., "Enantioselective Epoxide Polymerization Using a Bimetallic Cobalt Catalyst", Journal of the American Chemical Society, vol. 132, No. 46, 2010, pp. 16520-16525.
Trimm, D. L., "Minimisation of Carbon Monoxide in a Hydrogen Stream for Fuel Cell Application", Applied Catalysis A: General, vol. 296, 2005, 11 pages.
Van Zee et al., "Electronic Effects of Aluminum Complexes in the Copolymerization of Propylene Oxide with Tricyclic Anhydrides: Access to Well-Defined, Functionalizable Aliphatic Polyesters", Journal of the American Chemical Society, vol. 138, 2016, pp. 2755-2761.
Whiting et al., "Synthesis and Polymerization of Bicyclic Ketals: A Practical Route to High-Molecular Weight Polyketals", Journal of the American Chemical Society, vol. 135, 2013, pp. 10974-10977.
"Understanding Biobased Carbon Content", Society of the Plastics Industry Bioplastics Council, Feb. 2012, pp. 1-12.

\* cited by examiner

CATALYTIC CARBONYLATION CATALYSTS AND METHODS

CROSS REFERENCE TO RELATED APPLICATIONS

The present application is a continuation of U.S. patent application Ser. No. 14/117,393 (now U.S. Pat. No. 9,327,280), which is a U.S National Stage application of PCT/US2012/037675, filed internationally May 12, 2012, which claims priority to and the benefit of U.S. provisional patent application Ser. No. 61/485,660, filed May 13, 2011, each of which is hereby incorporated herein by reference in the present disclosure in its entirety.

FIELD OF THE INVENTION

The invention pertains to the field of catalytic carbonylation of heterocycles. More particularly, the invention pertains to unimolecular catalysts and related methods to carbonylate epoxides, aziridines, thiiranes, oxetanes, lactones, lactams and analogous compounds in the presence of such catalysts.

BACKGROUND

Catalytic carbonylation of epoxides, aziridines, thiiranes, oxetanes, lactones, lactams and analogous compounds have been shown to be useful for the synthesis of ring expanded products of such compounds. The early catalyst for the carbonylation of epoxides was based on the use of $[Co_2(CO)_8]$. EP-B-0 577 206 by Drent and Kragtwijk relates to a process for the carbonylation of epoxides to form beta-lactone in the presence of $[Co_2(CO)_8]$ and a hydroxy substituted pyridine compound. Alper and co-workers (*J. Org. Chem.* 2001, 66, 5424-5426) reported increased activity of carbonylation and selectivity for beta-lactone using combinations of $[PPN]^+[Co(CO)_4]^-$ and neutral metal complexes (PPN=bis(triphenylphosphine)iminium).

Further improvement of activity of carbonylation disclosed in U.S. Pat. No. 6,852,865 relates to bimetallic catalysts of the general type [metal complex]$^+$[Co(CO)$_4$]$^-$ for the ring-expanding carbonylation of epoxides, aziridines, thiiranes, oxetanes, lactones, lactams and analogous compounds.

Nonetheless, there remains a need for catalysts that have increased activity that will further reduce the catalyst cost in the carbonylation of epoxides, aziridines, thiiranes, oxetanes, lactones, lactams and analogous compounds.

SUMMARY OF THE INVENTION

The present invention provides catalyst systems having increased activity, and/or longer catalyst life in the carbonylation of heterocycles such as aziridines, thiiranes, oxetanes, lactones, lactams and, in particular, epoxides.

In one aspect, the present invention encompasses catalysts for the carbonylation of heterocycles comprising the combination of:
  i) one or more cationic functional moieties, where each cationic functional moiety comprises a linker and 1 to 4 cationic functional groups;
  ii) one or more ligands to which at least one cationic functional moiety is covalently tethered wherein the one or more ligand(s) are coordinated to one or two metal atoms; and
  iii) at least one anionic metal carbonyl species associated with a cation present on the metal complex.

In certain embodiments, a catalyst of the present invention has a formula $[(L^c)_a M_b (L'')_c]^{z+}$, where:
  $L^c$ is a ligand that includes at least one cationic functional moiety where, when two or more $L^c$ are present, each may be the same or different;
  M is a metal atom where, when two M are present, each may be the same or different;
  $L''$ is optionally present, and if present, is a ligand that does not include a cationic moiety where, when two or more $L''$ are present, each may be the same or different;
  a is an integer from 1 to 4 inclusive;
  b is an integer from 1 to 2 inclusive;
  c is an integer from 0 to 6 inclusive; and
  z is an integer greater than 0 that represents the cationic charge on the metal complex.

In certain embodiments, catalysts of the present conform to structure I:

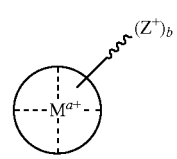

I wherein:
  ⊕ is a multidentate ligand;
  M is a metal atom coordinated to the multidentate ligand;
  a is the charge of the metal atom and ranges from 0 to 2; and
  ⁓⁓⁓(Z$^+$)$_b$ represents a cationic functional moiety,
  where ⁓⁓⁓ is a linker moiety covalently coupled to the multidentate ligand;
    $Z^+$ is a cationic functional group covalently coupled to the linker moiety; and
    b is the number of cationic functional groups coupled to the linker moiety and is an integer between 1 and 4 inclusive;

In certain embodiments, provided metal complexes conform to structure II:

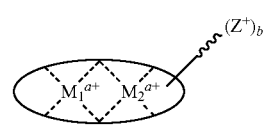

II

Where each of ⁓⁓⁓(Z$^+$)$_b$ and a is as defined above (each a may be the same or different), and
  $M^1$ is a first metal atom;
  $M^2$ is a second metal atom;
  ⬯ comprises a multidentate ligand system capable of coordinating both metal atoms.

In certain embodiments, the ligands in such catalyst comprise porphyrin or salen derivatives. In certain embodiments, the catalysts comprise a salen or porphyrin complex of a metal selected from the group consisting of: Zn(II), Cu(II), Mn(II), Co(II), Ru(II), Fe(II), Co(II), Rh(II), Ni(II), Pd(II), Mg(II), Al(III), Cr(III), Fe(III), Co(III), Ti(III), In(III), Ga(III), Mn(III). In certain embodiments M is Al(III). In certain embodiments M is Cr(III), Ti(IV) and Cr(IV). In certain embodiments, the catalysts comprise a salen or porphyrin complex of aluminum. In certain embodiments, the catalysts comprise a salen or porphyrin complex of chromium.

In certain embodiments, the catalysts comprise one or more cationic tethered functional groups comprising onium salts. In certain embodiments, the onium salts comprise at least one of nitrogen and phosphorous. In certain embodiments, the catalysts comprise one or more cationic tethered functional groups selected from the group consisting of:

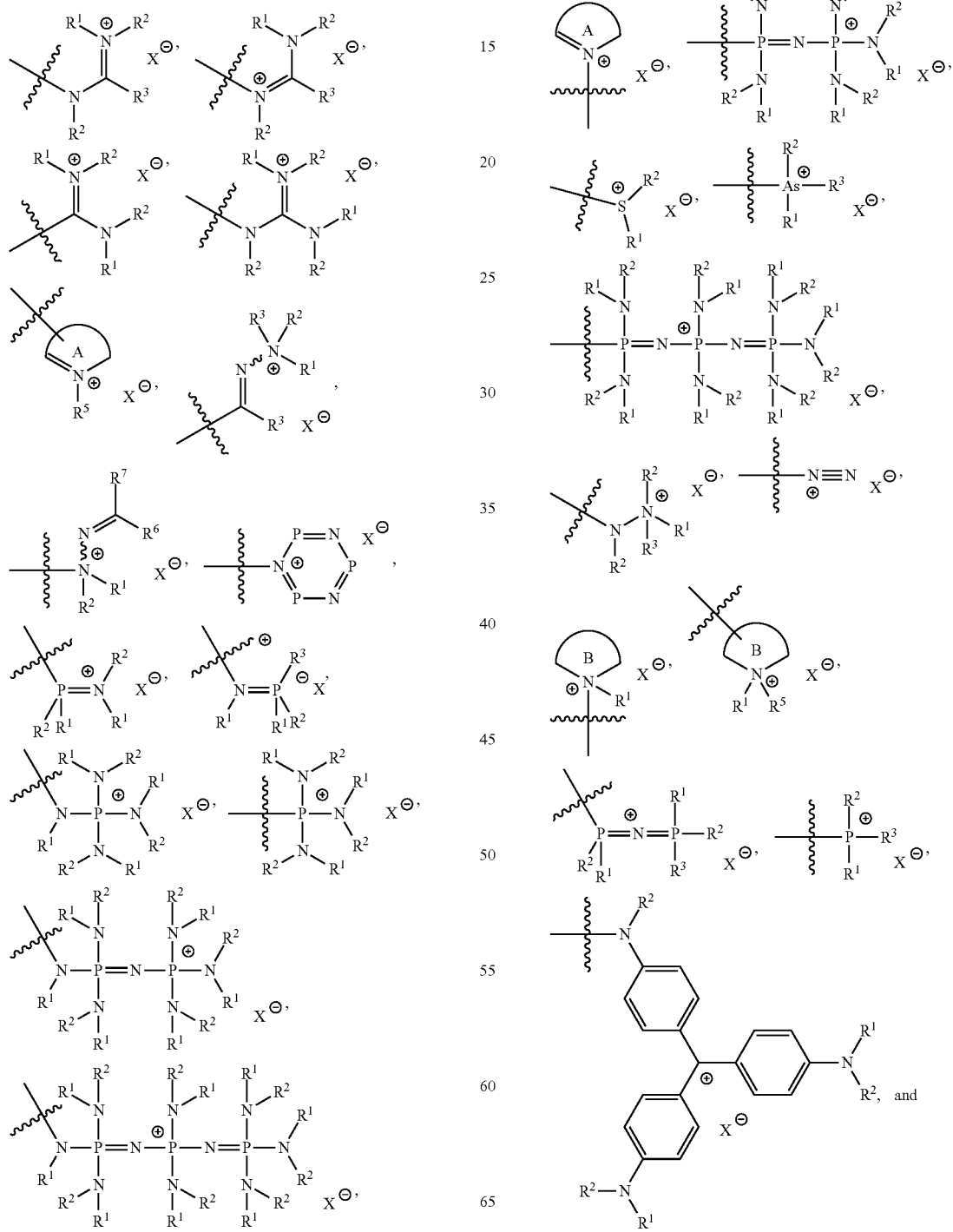

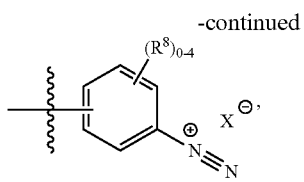

or a combination of two or more of these, wherein each of the variables is as defined below and in the classes and subclasses herein.

In certain embodiments, the catalysts comprise one or more cationic tethered functional groups selected from the group consisting of:

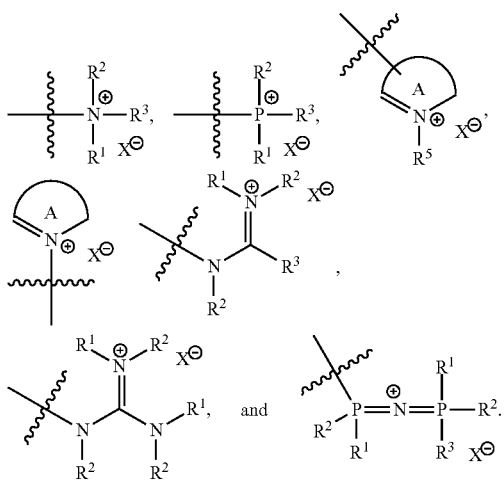

In another aspect, the present invention encompasses methods for the carbonylation of epoxides comprising the step of contacting an epoxide with carbon in the presence of a catalyst of the invention, to provide a product selected from the group consisting of beta lactone, cyclic anhydride, a polyester, and a mixture of any two or more of these.

In certain embodiments, the present invention provides methods for the carbonylation of ethylene oxide to provide a product consisting substantially of beta propiolactone.

In certain embodiments, the present invention provides methods for the carbonylation of ethylene oxide to provide a product consisting substantially of polypropiolactone.

Definitions

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

Certain compounds of the present invention can comprise one or more asymmetric centers, and thus can exist in various stereoisomeric forms, e.g., enantiomers and/or diastereomers. Thus, inventive compounds and compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of enantiomers or diastereomers are provided.

Furthermore, certain compounds, as described herein may have one or more double bonds that can exist as either a Z or E isomer, unless otherwise indicated. The invention additionally encompasses the compounds as individual isomers substantially free of other isomers and alternatively, as mixtures of various isomers, e.g., racemic mixtures of enantiomers. In addition to the above-mentioned compounds per se, this invention also encompasses compositions comprising one or more compounds.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, a compound may, in some embodiments, be provided substantially free of one or more corresponding stereoisomers, and may also be referred to as "stereochemically enriched."

Where a particular enantiomer is preferred, it may, in some embodiments be provided substantially free of the opposite enantiomer, and may also be referred to as "optically enriched." "Optically enriched," as used herein, means that the compound is made up of a significantly greater proportion of one enantiomer. In certain embodiments the compound is made up of at least about 90% by weight of an enantiomer. In some embodiments the compound is made up of at least about 95%, 97%, 98%, 99%, 99.5%, 99.7%, 99.8%, or 99.9% by weight of an enantiomer. In some embodiments the enantiomeric excess of provided compounds is at least about 90%, 95%, 97%, 98%, 99%, 99.5%, 99.7%, 99.8%, or 99.9%. In some embodiments, enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, NY, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E.L. Eliel, Ed., Univ. of Notre Dame Press, Notre Dame, Ind. 1972).

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-30 carbon atoms. In certain embodiments, aliphatic groups contain 1-12 carbon atoms. In certain embodiments, aliphatic groups contain 1-8 carbon atoms. In certain embodiments, aliphatic groups contain 1-6 carbon atoms. In some embodiments, aliphatic groups contain 1-5 carbon atoms, in some embodiments, aliphatic groups contain 1-4 carbon atoms, in yet other embodiments aliphatic groups contain 1-3 carbon atoms, and in yet other embodiments aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroaliphatic," as used herein, refers to aliphatic groups wherein one or more carbon atoms are independently replaced by one or more atoms selected from the group consisting of oxygen, sulfur, nitrogen, phosphorus, or boron. In certain embodiments, one or two carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle," "hetercyclyl," "heterocycloaliphatic," or "heterocyclic" groups.

The term "epoxide", as used herein, refers to a substituted or unsubstituted oxirane. Substituted oxiranes include monosubstituted oxiranes, disubstituted oxiranes, trisubstituted oxiranes, and tetrasubstituted oxiranes. Such epoxides may be further optionally substituted as defined herein. In certain embodiments, epoxides comprise a single oxirane moiety. In certain embodiments, epoxides comprise two or more oxirane moieties.

The term "glycidyl", as used herein, refers to an oxirane substituted with a hydroxyl methyl group or a derivative thereof. The term glycidyl as used herein is meant to include moieties having additional substitution on one or more of the carbon atoms of the oxirane ring or on the methylene group of the hydroxymethyl moiety, examples of such substitution may include, but are not limited to: alkyl groups, halogen atoms, aryl groups etc. The terms glycidyl ester, glycidyl acrylate, glydidyl ether etc. denote substitution at the oxygen atom of the above-mentioned hydroxymethyl group, i.e. that oxygen atom is bonded to an acyl group, an acrylate group, or an alkyl group respectively.

The term "acrylate" or "acrylates" as used herein refer to any acyl group having a vinyl group adjacent to the acyl carbonyl. The terms encompass mono-, di- and tri-substituted vinyl groups. Examples of acrylates include, but are not limited to: acrylate, methacrylate, ethacrylate, cinnamate (3-phenylacrylate), crotonate, tiglate, and senecioate. Because it is known that cylcopropane groups can in certain instances behave very much like double bonds, cyclopropane esters are specifically included within the definition of acrylate herein.

The term "polymer", as used herein, refers to a molecule of high relative molecular mass, the structure of which comprises the multiple repetition of units derived, actually or conceptually, from molecules of low relative molecular mass. In certain embodiments, a polymer is comprised of only one monomer species (e.g., polyethylene oxide). In certain embodiments, a polymer of the present invention is a copolymer, terpolymer, heteropolymer, block copolymer, or tapered heteropolymer of one or more epoxides.

The term "unsaturated", as used herein, means that a moiety has one or more double or triple bonds.

The terms "cycloaliphatic", "carbocycle", or "carbocyclic", used alone or as part of a larger moiety, refer to a saturated or partially unsaturated cyclic aliphatic monocyclic, bicyclic, or polycyclic ring systems, as described herein, having from 3 to 12 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic groups is bicyclic. In some embodiments, a carbocyclic group is tricyclic. In some embodiments, a carbocyclic group is polycyclic.

The term "alkyl," as used herein, refers to saturated, straight- or branched-chain hydrocarbon radicals derived from an aliphatic moiety containing between one and six carbon atoms by removal of a single hydrogen atom. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms, in some embodiments, alkyl groups contain 1-4 carbon atoms, in yet other embodiments alkyl groups contain 1-3 carbon atoms, and in yet other embodiments alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. Unless otherwise specified, alkenyl groups contain 2-12 carbon atoms. In certain embodiments, alkenyl groups contain 2-8 carbon atoms. In certain embodiments, alkenyl groups contain 2-6 carbon atoms. In some embodiments, alkenyl groups contain 2-5 carbon atoms, in some embodiments, alkenyl groups contain 2-4 carbon atoms, in yet other embodiments alkenyl groups contain 2-3 carbon atoms, and in yet other embodiments alkenyl groups contain 2 carbon atoms. Alkenyl groups include, for example, ethenyl, propenyl, butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. Unless otherwise specified, alkynyl groups contain 2-12 carbon atoms. In certain embodiments, alkynyl groups contain 2-8 carbon atoms. In certain embodiments, alkynyl groups contain 2-6 carbon atoms. In some embodiments, alkynyl groups contain 2-5 carbon atoms, in some embodiments, alkynyl groups contain 2-4 carbon atoms, in yet other embodiments alkynyl groups contain 2-3 carbon atoms, and in yet other embodiments alkynyl groups contain 2 carbon atoms. Representative alkynyl groups include, but are not limited to, ethynyl, 2-propynyl (propargyl), 1-propynyl, and the like.

The term "carbocycle" and "carbocyclic ring" as used herein, refers to monocyclic and polycyclic moieties wherein the rings contain only carbon atoms. Unless otherwise specified, carbocycles may be saturated, partially unsaturated or aromatic, and contain 3 to 20 carbon atoms. Representative carbocyles include cyclopropane, cyclobutane, cyclopentane, cyclohexane, bicyclo[2,2,1]heptane, norbornene, phenyl, cyclohexene, naphthalene, spiro[4.5]decane, The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In certain embodiments of the present invention, "aryl" refers to an aromatic ring system which includes, but is not limited to, phenyl, biphenyl, naphthyl, anthracyl and the like, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenantriidinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 14 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-14-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

In some chemical structures herein, substituents are shown attached to a bond which crosses a bond in a ring of the depicted molecule. This means that one or more of the substituents may be attached to the ring at any available position (usually in place of a hydrogen atom of the parent structure). In cases where an atom of a ring so substituted has two substitutable positions, two groups may be present on the same ring atom. When more than one substituent is present, each is defined independently of the others, and each may have a different structure. In cases where the substituent shown crossing a bond of the ring is —R, this has the same meaning as if the ring were said to be "optionally substituted" as described in the preceding paragraph.

Suitable monovalent substituents on a substitutable carbon atom of an "optionally substituted" group are independently halogen; —$(CH_2)_{0-4}R°$; —$(CH_2)_{0-4}OR°$; —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with R°; —$(CH_2)_{0-4}O(CH_2)_{0-1}Ph$ which may be substituted with R°; —CH=CHPh, which may be substituted with R°; —$NO_2$; —CN; —$N_3$; —$(CH_2)_{0-4}N(R°)_2$; —$(CH_2)_{0-4}N(R°)C(O)R°$; —N(R°)C(S)R°; —$(CH_2)_{0-4}N(R°)C(O)NR°_2$; —N(R°)C(S)NR°$_2$; —$(CH_2)_{0-4}N(R°)C(O)OR°$; —N(R°)N(R°)C(O)R°; —N(R°)N(R°)C(O)NR°$_2$; —N(R°)N(R°)C(O)OR°; —$(CH_2)_{0-4}C(O)R°$; —C(S)R°; —$(CH_2)_{0-4}C(O)OR°$; —$(CH_2)_{0-4}C(O)N(R°)_2$; —$(CH_2)_{0-4}C(O)SR°$; —$(CH_2)_{0-4}C(O)OSiR°_3$; —$(CH_2)_{0-4}OC(O)R°$; —OC(O)$(CH_2)_{0-4}SR$—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°; —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene) O—N(R°)$_2$; or —(C$_{1-4}$ straight or branched alkylene) C(O)O—N(R°)$_2$, wherein each R° may be substituted as defined below and is independently hydrogen, C$_{1-8}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or polycyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-4}$C(O)N(R°)$_2$; —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "catalyst" refers to a substance the presence of which increases the rate of a chemical reaction, while not being consumed or undergoing a permanent chemical change itself.

"Tetradentate" refers to ligands having four sites capable of coordinating to a single metal center.

DETAILED DESCRIPTION OF CERTAIN EMBODIMENTS

The present invention encompasses catalysts for the carbonylation of epoxides, aziridines, thiiranes, oxetanes, lactones, lactams and analogous compounds. According to one aspect, the present invention provides carbonylation catalysts comprising a metal complex with one or more cationic functional moieties covalently tethered to a ligand that is coordinated to a metal center of the complex and comprising one or more anionic metal carbonyl compounds. The metal complex contains one or more ligands, one or two metal atoms coordinated to the ligand or ligands, and one or more cationic functional moieties covalently tethered to the ligand. Each cationic functional moiety comprises a linker moiety and one or more cationic functional groups. In certain embodiments, at least one cationic functional group acts as a counterion for the anionic metal carbonyl compound.

In certain embodiments, provided carbonlyation catalysts of the present invention include a cationic metal complex and at least one anionic metal carbonyl compound balancing the charge of the metal complex. In certain embodiments, there are 1 to 17 such anionic metal carbonyls balancing the charge of the metal complex. In certain embodiments, there are 1 to 9 such anionic metal carbonyls balancing the charge of the metal complex. In certain embodiments, there are 1 to 5 such anionic metal carbonyls balancing the charge of the metal complex. In certain embodiments, there are 1 to 3 such anionic metal carbonyls balancing the charge of the metal complex.

In certain embodiments, the metal complex has the formula [(L$^c$)$_a$M$_b$(L$''$)$_c$]$^{z+}$, where:

L$^c$ is a ligand that includes at least one cationic functional moiety where, when two or more L$^c$ are present, each may be the same or different;

M is a metal atom where, when two M are present, each may be the same or different;

L″ is optionally present, and if present, is a ligand that does not include a cationic moiety where, when two or more L″ are present, each may be the same or different;

a is an integer from 1 to 4 inclusive;
b is an integer from 1 to 2 inclusive;
c is an integer from 0 to 6 inclusive; and
z is an integer greater than 0 that represents the cationic charge on the metal complex.

In certain embodiments, provided metal complexes conform to structure I:

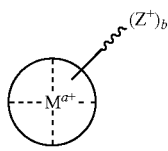

I wherein:
⊕ is a multidentate ligand;
M is a metal atom coordinated to the multidentate ligand;
a is the charge of the metal atom and ranges from 0 to 2; and
$\sim\sim(Z^1)_b$ represents a cationic functional moiety,
where $\sim\sim$ is a linker moiety covalently coupled to the multidentate ligand;
$Z^+$ is a cationic functional group covalently coupled to the linker moiety; and
b is the number of cationic functional groups coupled to the linker moiety and is an integer between 1 and 4 inclusive;

In certain embodiments, provided metal complexes conform to structure II:

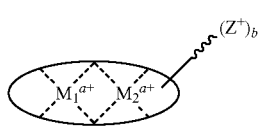

II

Where each of $\sim\sim(Z^+)_b$ and a is as defined above (each a may be the same or different), and
$M^1$ is a first metal atom;
$M^2$ is a second metal atom;
⟨⟩ comprises a multidentate ligand system capable of coordinating both metal atoms.

For sake of clarity, and to avoid confusion between the net and total charge of the metal atoms in complexes I and II and other structures herein, the charge ($a^+$) shown on the metal atom in complexes I and II above represents the net charge on the metal atom after it has satisfied any anionic sites of the multidentate ligand. For example, if a metal atom in a complex of formula I were Cr(III), and the ligand were porphyrin (a tetradentate ligand with a charge of −2), then the chromium atom would have a net change of +1, and a would be 1.

Before more fully describing the inventive catalysts, the following section provides a more detailed understanding of what the tethered cationic functional moieties are.

I. Cationic Functional Moieties

As described above, inventive metal complexes of the present invention include one or more cationic functional moieties. Each cationic functional moiety denoted generically herein as "$\sim\sim(Z^1)_b$" comprises a linker "$\sim\sim$" coupled to at least one cationic functional group Z, where b denotes the number of cationic functional groups present on a single linker moiety. Thus, a single cationic functional moiety may contain two or more cationic functional groups.

In some embodiments, there may be one or more cationic functional moieties $\sim\sim(Z^+)_b$ tethered to a given metal complex; each cationic functional moiety may itself contain more than one cationic functional group Z. In certain embodiments, each cationic functional moiety contains only one cationic functional group (i.e. b=1). In some embodiments, each cationic functional moiety contains more than one cationic functional groups (i.e. b>1). In certain embodiments, an cationic functional moiety contains two cationic functional groups (i.e. b=2). In certain embodiments, an cationic functional moiety contains three cationic functional groups (i.e. b=3). In certain embodiments, an cationic functional moiety contains four cationic functional groups (i.e. b=4). In certain embodiments where more than one cationic functional group is present on an cationic functional moiety, the cationic functional groups are the same. In some embodiments where more than one cationic functional group is present on an cationic functional moiety, two or more of the cationic functional groups are different.

Ia. Linkers

In certain embodiments, a linker $\sim\sim$ may comprise a bond. In this case, the cationic functional group Z is bonded directly to the ligand. To avoid the need to arbitrarily define where a ligand ends and a tether begins, it is to be understood that if a Z group is bonded directly to an atom that is typically regarded as part of the parent structure of the ligand, then the linker $\sim\sim$ is to be regarded as comprising a bond. In certain embodiments, when $\sim\sim$ comprises a bond, b is 1.

In certain embodiments, each linker $\sim\sim$ contains 1-30 atoms including at least one carbon atom, and optionally one or more atoms selected from the group consisting of N, O, S, Si, B, and P.

In certain embodiments, a linker is an optionally substituted $C_{2-30}$ aliphatic group wherein one or more methylene units are optionally and independently replaced by -Cy-, —NR$^y$—, —N(R$^y$)C(O)—, —C(O)N(R$^y$)—, —O—, —C(O)—, —OC(O)—, —C(O)O—, —S—, —SO—, —SO$_2$—, —C(=S)—, —C(=NR$^y$)—, or —N=N—, wherein:

each -Cy- is independently an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur; and each R$^y$ is independently —H, or an optionally substituted radical selected from the group consisting of $C_{1-6}$ aliphatic, phenyl, a 3-7 membered saturated or partially unsaturated carbocyclic ring, a 3-7 membered saturated or partially unsaturated monocyclic heterocyclic ring having 1-2 heteroatoms independently selected from nitrogen, oxygen, or sulfur, a 5-6 membered heteroaryl ring having 1-3 heteroatoms independently selected from nitrogen, oxygen, or sulfur, and 8- to 10-membered aryl.

In certain embodiments, a linker $\sim\sim$ is a $C_4$-$C_{12}$ aliphatic group substituted with one or more moieties selected from the group consisting of halogen, —NO$_2$, —CN, —SR$^y$, —S(O)R$^y$, —S(O)$_2$R$^y$, —NR$^y$C(O)R$^y$, —OC (O)R$^y$, —CO$_2$R$^y$, —NCO, —N$_3$, —OR$^4$, —OC(O)N(R$^y$)$_2$, —N(R$^y$)$_2$, —NR$^y$C(O)R$^y$, and —NR$^y$C(O)OR$^y$, where each R$^y$ and R$^4$ is independently as defined above and described in classes and subclasses herein.

In certain embodiments, a linker ———⁀⁀⁀ is an optionally substituted C$_3$-C$_{30}$ aliphatic group. In certain embodiments, a linker is an optionally substituted C$_{4-24}$ aliphatic group. In certain embodiments, a linker moiety is an optionally substituted C$_4$-C$_{20}$ aliphatic group. In certain embodiments, a linker moiety is an optionally substituted C$_4$-C$_{12}$ aliphatic group. In certain embodiments, a linker is an optionally substituted C$_{4-10}$ aliphatic group. In certain embodiments, a linker is an optionally substituted C$_{4-8}$ aliphatic group. In certain embodiments, a linker moiety is an optionally substituted C$_4$-C$_6$ aliphatic group. In certain embodiments, a linker moiety is an optionally substituted C$_6$-C$_{12}$ aliphatic group. In certain embodiments, a linker moiety is an optionally substituted C$_8$ aliphatic group. In certain embodiments, a linker moiety is an optionally substituted C$_7$ aliphatic group. In certain embodiments, a linker moiety is an optionally substituted C$_6$ aliphatic group. In certain embodiments, a linker moiety is an optionally substituted C$_5$ aliphatic group. In certain embodiments, a linker moiety is an optionally substituted C$_4$ aliphatic group. In certain embodiments, a linker moiety is an optionally substituted C$_3$ aliphatic group. In certain embodiments, a aliphatic group in the linker moiety is an optionally substituted straight alkyl chain. In certain embodiments, the aliphatic group is an optionally substituted branched alkyl chain. In some embodiments, a linker moiety is a C$_4$ to C$_{20}$ alkyl group having one or more methylene groups replaced by —C(R°)$_2$— wherein R° is as defined above. In certain embodiments, a linker ———⁀⁀⁀ consists of a bivalent aliphatic group having 4 to 30 carbons including one or more C$_{1-4}$ alkyl substituted carbon atoms. In certain embodiments, a linker moiety consists of a bivalent aliphatic group having 4 to 30 carbons including one or more gem-dimethyl substituted carbon atoms.

In certain embodiments, a linker ———⁀⁀⁀ includes one or more optionally substituted cyclic elements selected from the group consisting of saturated or partially unsaturated carbocyclic, aryl, heterocyclic, or heteroaryl. In certain embodiments, a linker moiety consists of the substituted cyclic element, in some embodiments the cyclic element is part of a linker with one or more non-ring heteroatoms or optionally substituted aliphatic groups comprising other parts of the linker moiety.

In some embodiments, a linker moiety is of sufficient length to allow an atom bearing a positive (either wholly or through a resonance structure) within a cationic functional group to be positioned near a metal atom of a metal complex. In certain embodiments, a linker moiety is of sufficient length to allow an atom bearing a positive within a cationic functional group to be positioned within about 6 Å, within about 5 Å, within about 4 Å, within about 3.5 Å, or within about 3 Å. In certain embodiments, structural constraints are built into a linker moiety to control the disposition and orientation of one or more cationic functional groups near a metal center of a metal complex. In certain embodiments, such structural constraints are selected from the group consisting of cyclic moieties, bicyclic moieties, bridged cyclic moieties and tricyclic moieties. In some embodiments, such structural constraints are the result of acyclic steric interactions. In certain embodiments, steric interactions due to syn-pentane, gauche-butane, and/or allylic strain in a linker moiety, bring about structural constraints that affect the orientation of a linker and one or more cationic groups. In certain embodiments, structural constraints are selected from the group consisting of cis double bonds, trans double bonds, cis allenes, trans allenes, and triple bonds. In some embodiments, structural constraints are selected from the group consisting of substituted carbons including geminally disubstituted groups such as sprirocyclic rings, gem dimethyl groups, gem diethyl groups and gem diphenyl groups. In certain embodiments, structural constraints are selected from the group consisting of heteroatom-containing functional groups such as sulfoxides, amides, and oximes.

In certain embodiments, linker moieties are selected from the group consisting of:

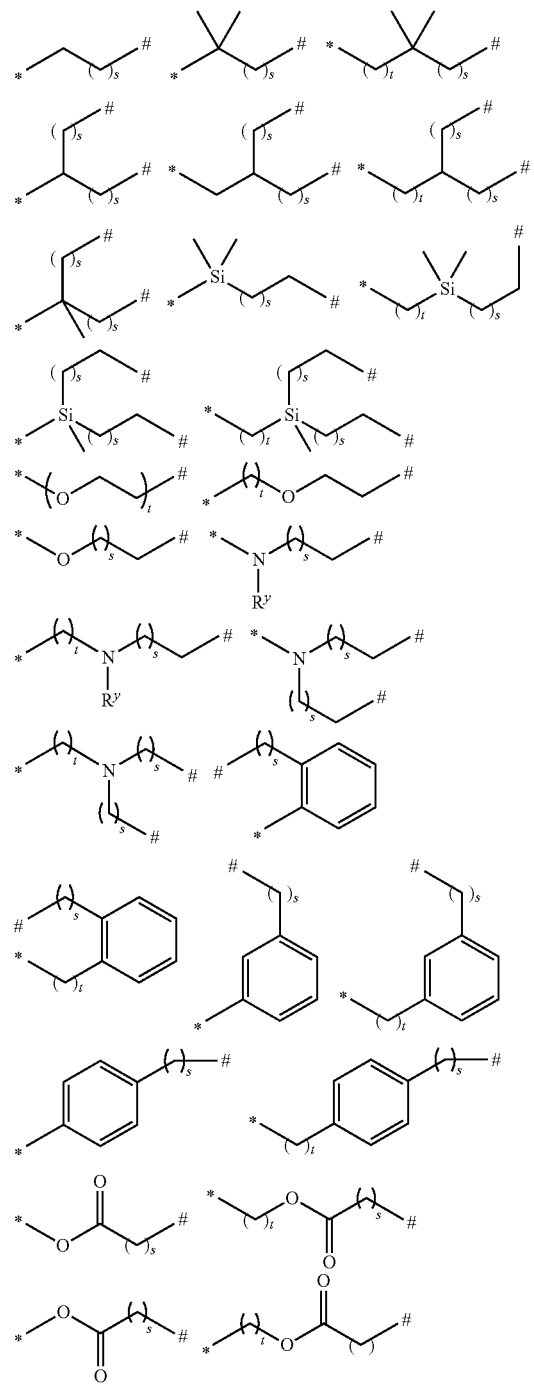

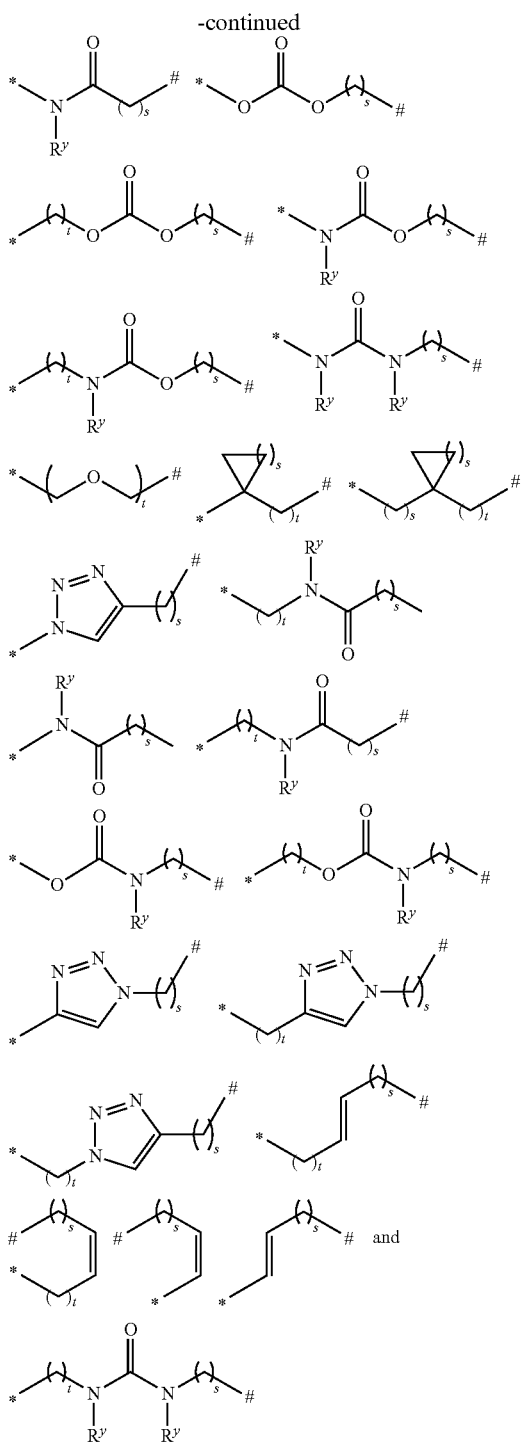

wherein each s is independently 0-6, t is 0-4, $R^y$ as defined above and described in classes and subclasses herein, * represents the site of attachment to a ligand, and each # represents a site of attachment of a cationic functional group.

In some embodiments, s is 0. In some embodiments, s is 1. In some embodiments, s is 2. In some embodiments, s is 3. In some embodiments, s is 4. In some embodiments, s is 5. In some embodiments, s is 6.

In some embodiments, t is 1. In some embodiments, t is 2. In some embodiments, t is 3. In some embodiments, t is 4.

In certain embodiments, there is at least one cationic functional moiety tethered to the multidentate ligand. In certain embodiments, there are 1 to 8 such cationic functional moieties tethered to the multidentate ligand. In certain embodiments, there are 1 to 4 such cationic functional moieties tethered to the multidentate ligand. In certain embodiments, there are 1 to 2 such cationic functional moieties tethered to the multidentate ligand.

Ib. Cationic Functional Groups

In certain embodiments, one or more tethered cationic groups ($Z^+$) comprise organic cations. In certain embodiments, one or more tethered cationic groups ($Z^+$) comprises an onium group. In certain embodiments, such onium groups include one or more nitrogen and/or phosphorous atoms.

In certain embodiments, one or more tethered cationic groups ($Z^+$) on provided metal complexes (i.e. complexes of formulae I or II or any of the embodiments, classes or subclasses thereof described herein) is selected from a structure in Table Z-2:

TABLE Z-2

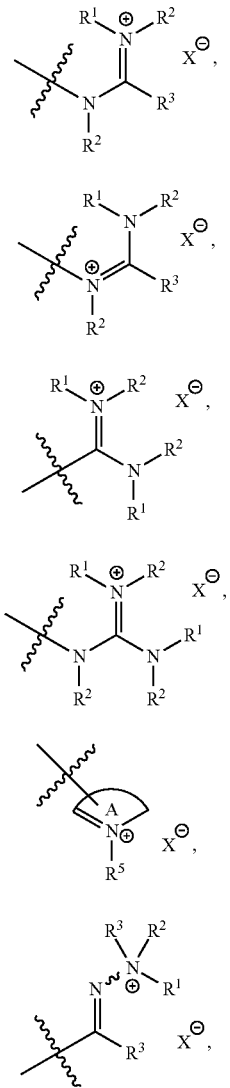

TABLE Z-2-continued
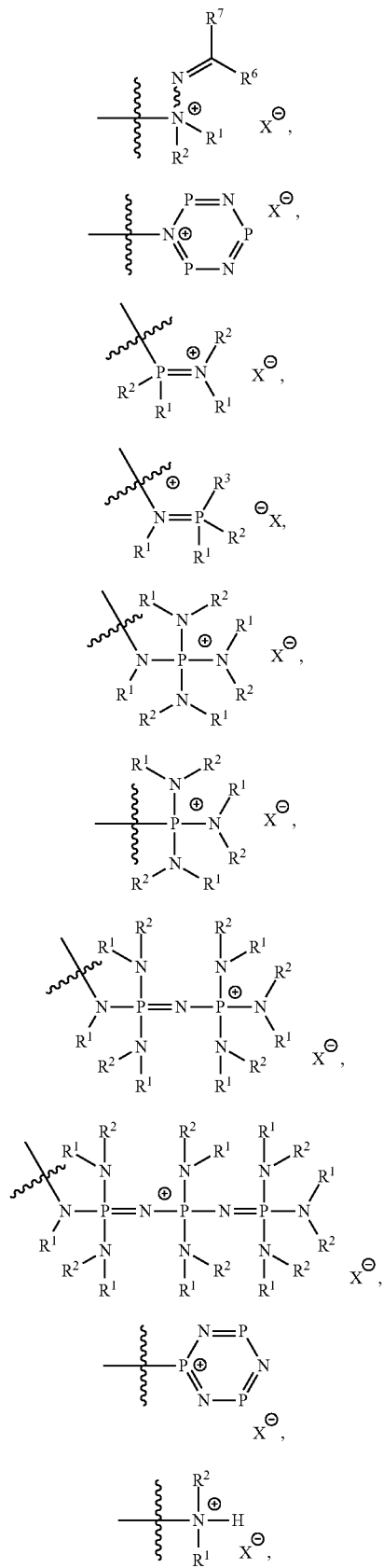
TABLE Z-2-continued
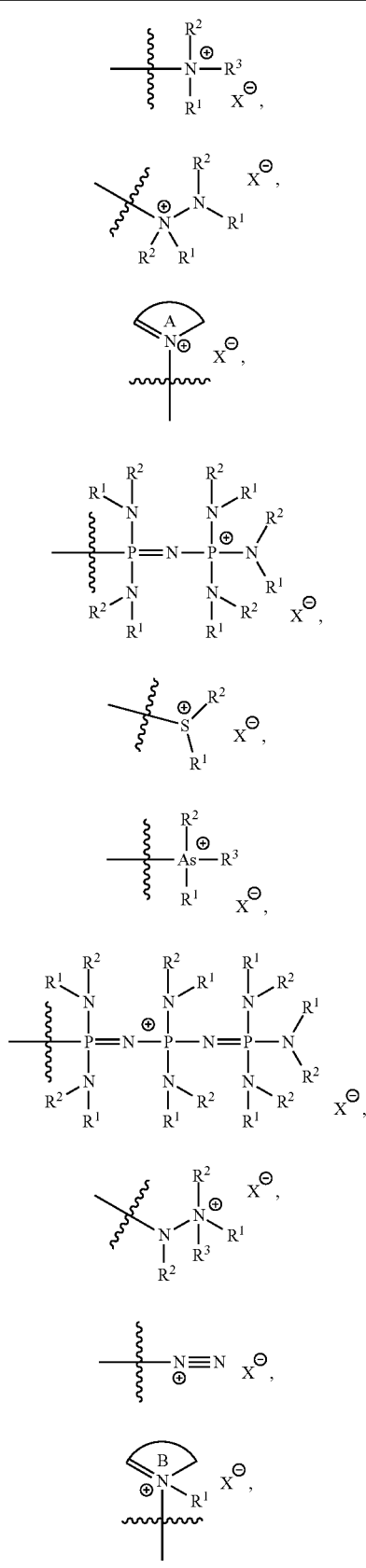

TABLE Z-2-continued

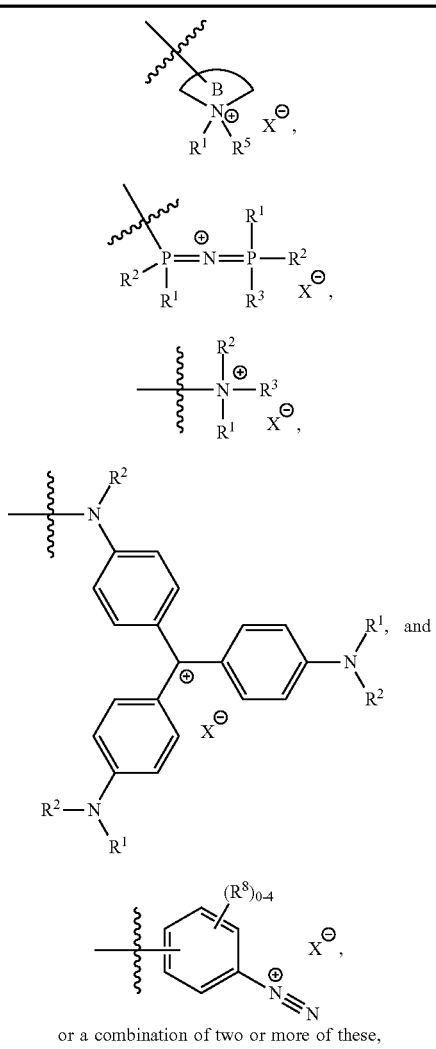

or a combination of two or more of these, wherein:
  each $R^1$ and $R^2$ is independently hydrogen or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein $R^1$ and $R^2$ can be taken together with intervening atoms to form one or more optionally substituted rings optionally containing one or more additional heteroatoms;
  each $R^3$ is independently hydrogen or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein an $R^3$ group can be taken with an $R^1$ or $R^2$ group to form one or more optionally substituted rings; and
  $R^5$ is $R^2$ or hydroxyl; wherein $R^1$ and $R^5$ can be taken together with intervening atoms to form one or more optionally substituted carbocyclic, heterocyclic, aryl, or heteroaryl rings;
  each $R^6$ and $R^7$ is independently hydrogen or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein $R^6$ and $R^7$ can be taken together with intervening atoms to form one or more optionally substituted rings optionally containing one or more heteroatoms, and an $R^6$ and $R^7$ group can be taken with an $R^1$ or $R^2$ group to form one or more optionally substituted rings;
  each occurrence of $R^8$ is independently selected from the group consisting of: halogen, $-NO_2$, $-CN$, $-SR^y$, $-S(O)R^y$, $-S(O)_2R^y$, $-NR^yC(O)R^y$, $-OC(O)R^y$, $-CO_2R^y$, $-NCO$, $-N_3$, $-OR^7$, $-OC(O)N(R^y)_2$, $-N(R^y)_2$, $-NR^yC(O)R^y$, $-NR^yC(O)OR^y$; or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur;

phenyl; or an 8- to 14-membered polycyclic aryl ring; wherein each $R^y$ is independently as defined above and described in classes and subclasses herein, and where two or more adjacent $R^8$ groups can be taken together to form an optionally substituted saturated, partially unsaturated, or aromatic 5- to 12-membered ring containing 0 to 4 heteroatoms;

$X^-$ is any anionic metal carbonyl compound;

Ring A is an optionally substituted, 5- to 10-membered heteroaryl group; and

Ring B is an optionally substituted, 3- to 8-membered saturated or partially unsaturated monocyclic heterocyclic ring having 0-2 heteroatoms in addition to the depicted ring nitrogen atom independently selected from nitrogen, oxygen, or sulfur.

In certain embodiments, each $R^1$ group is the same. In other embodiments, $R^1$ groups are different. In certain embodiments, $R^1$ is hydrogen. In some embodiments, $R^1$ is an optionally substituted radical selected from the group consisting of $C_{1-20}$ aliphatic; $C_{1-20}$ heteroaliphatic, 5- to 14-membered heteroaryl, phenyl, 8- to 10-membered aryl and 3- to 7-membered heterocyclic. In some embodiments, $R^1$ is an optionally substituted radical selected from the group consisting of a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring.

In certain embodiments, $R^1$ is an optionally substituted radical selected from the group consisting of $C_{1-12}$ aliphatic and $C_{1-12}$ heteroaliphatic. In some embodiments, $R^1$ is optionally substituted $C_{1-20}$ aliphatic. In some embodiments, $R^1$ is optionally substituted $C_{1-12}$ aliphatic. In some embodiments, $R^1$ is optionally substituted $C_{1-6}$ aliphatic. In some embodiments, $R^1$ is optionally substituted $C_{1-20}$ heteroaliphatic. In some embodiments, $R^1$ is optionally substituted $C_{1-12}$ heteroaliphatic. In some embodiments, $R^1$ is optionally substituted phenyl. In some embodiments, $R^1$ is optionally substituted 8- to 10-membered aryl. In some embodiments, $R^1$ is an optionally substituted 5- to 6-membered heteroaryl group. In some embodiments, $R^1$ is an optionally substituted 8- to 14-membered polycyclic heteroaryl group. In some embodiments, $R^1$ is optionally substituted 3- to 8-membered heterocyclic.

In certain embodiments, each $R^1$ is independently hydrogen, methyl, ethyl, propyl, butyl, pentyl, hexyl, heptyl, octyl, optionally substituted phenyl, or optionally substituted benzyl. In certain embodiments, $R^1$ is methyl, ethyl, propyl, butyl, pentyl, hexyl, heptyl, octyl, phenyl or benzyl. In some embodiments, $R^1$ is butyl. In some embodiments, $R^1$ is isopropyl. In some embodiments, $R^1$ is neopentyl. In some embodiments, $R^1$ is perfluoro. In some embodiments, $R^1$ is —$CF_2CF_3$. In some embodiments, $R^1$ is phenyl. In some embodiments, $R^1$ is benzyl.

In certain embodiments, each $R^2$ group is the same. In other embodiments, $R^2$ groups are different. In certain embodiments, $R^2$ is hydrogen. In some embodiments, $R^2$ is an optionally substituted radical selected from the group consisting of $C_{1-20}$ aliphatic; $C_{1-2o}$ heteroaliphatic, 5- to 14-membered heteroaryl, phenyl, 8- to 10-membered aryl and 3- to 7-membered heterocyclic. In some embodiments, $R^2$ is an optionally substituted radical selected from the group consisting of a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring.

In certain embodiments, $R^2$ is an optionally substituted radical selected from the group consisting of $C_{1-12}$ aliphatic and $C_{1-12}$ heteroaliphatic. In some embodiments, $R^2$ is optionally substituted $C_{1-20}$ aliphatic. In some embodiments, $R^2$ is optionally substituted $C_{1-12}$ aliphatic. In some embodiments, $R^2$ is optionally substituted $C_{1-6}$ aliphatic. In some embodiments, $R^2$ is optionally substituted $C_{1-20}$ heteroaliphatic. In some embodiments, $R^2$ is optionally substituted $C_{1-12}$ heteroaliphatic. In some embodiments, $R^2$ is optionally substituted phenyl. In some embodiments, $R^2$ is optionally substituted 8- to 10-membered aryl. In some embodiments, $R^2$ is an optionally substituted 5- to 6-membered heteroaryl group. In some embodiments, $R^2$ is an optionally substituted 8- to 14-membered polycyclic heteroaryl group. In some embodiments, $R^2$ is optionally substituted 3- to 8-membered heterocyclic.

In certain embodiments, each $R^2$ is independently hydrogen, methyl, ethyl, propyl, butyl, pentyl, hexyl, heptyl, octyl, optionally substituted phenyl, or optionally substituted benzyl. In certain embodiments, $R^2$ is methyl, ethyl, propyl, butyl, pentyl, hexyl, heptyl, octyl, phenyl or benzyl. In some embodiments, $R^2$ is butyl. In some embodiments, $R^2$ is isopropyl. In some embodiments, $R^2$ is neopentyl. In some embodiments, $R^2$ is perfluoro. In some embodiments, $R^2$ is —$CF_2CF_3$. In some embodiments, $R^2$ is phenyl. In some embodiments, $R^2$ is benzyl.

In certain embodiments, each $R^1$ and $R^2$ are hydrogen. In some embodiments, each $R^1$ is hydrogen each and each $R^2$ is other than hydrogen. In some embodiments, each $R^2$ is hydrogen each and each $R^1$ is other than hydrogen.

In certain embodiments, $R^1$ and $R^2$ are both methyl, ethyl, propyl, butyl, pentyl, hexyl, heptyl, octyl, phenyl or benzyl. In some embodiments, $R^1$ and $R^2$ are each butyl. In some embodiments, $R^1$ and $R^2$ are each isopropyl. In some embodiments, $R^1$ and $R^2$ are each perfluoro. In some embodiments, $R^1$ and $R^2$ are —$CF_2CF_3$. In some embodiments, $R^1$ and $R^2$ are each phenyl. In some embodiments, $R^1$ and $R^2$ are each benzyl.

In some embodiments, $R^1$ and $R^2$ are taken together with intervening atoms to form one or more optionally substituted carbocyclic, heterocyclic, aryl, or heteroaryl rings. In certain embodiments, $R^1$ and $R^2$ are taken together to form a ring fragment selected from the group consisting of: —$C(R^y)_2$—, —$C(R^y)_2C(R^y)_2$—, —$C(R^y)_2C(R^y)_2C(R^y)_2$—, —$C(R^y)_2OC(R^y)_2$—, and —$C(R^y)_2NR^yC(R^y)_2$—, wherein $R^y$ is as defined above. In certain embodiments, $R^1$ and $R^2$ are taken together to form a ring fragment selected from the group consisting of: —$CH_2$—, —$CH_2CH_2$—, —$CH_2CH_2CH_2$—, —$CH_2OCH_2$—, and —$CH_2NR^yCH_2$—. In some embodiments, $R^1$ and $R^2$ are taken together to form an unsaturated linker moiety optionally containing one or more additional heteroatoms. In some embodiments, the resulting nitrogen-containing ring is partially unsaturated. In certain embodiments, the resulting nitrogen-containing ring comprises a fused polycyclic heterocycle.

In certain embodiments, $R^3$ is H. In certain embodiments, $R^3$ is optionally $C_{1-20}$ aliphatic; $C_{1-20}$ heteroaliphatic, 5- to 14-membered heteroaryl, phenyl, 8- to 10-membered aryl or 3- to 7-membered heterocyclic. In some embodiments, $R^3$ is an optionally substituted radical selected from the group consisting of a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring. In certain embodiments, $R^3$ is optionally substituted $C_{1-12}$ aliphatic. In some embodiments, $R^3$ is optionally substituted $C_{1-6}$ aliphatic. In certain embodiments, $R^3$ is optionally substituted phenyl.

In certain embodiments, $R^3$ is methyl, ethyl, propyl, butyl, pentyl, hexyl, heptyl, octyl, phenyl or benzyl. In some embodiments, $R^3$ is butyl. In some embodiments, $R^3$ is isopropyl. In some embodiments, $R^3$ is perfluoro. In some embodiments, $R^3$ is $-CF_2CF_3$.

In some embodiments, one or more $R^1$ or $R^2$ groups are taken together with $R^3$ and intervening atoms to form an optionally substituted heterocyclic or heteroaryl ring. In certain embodiments, $R^1$ and $R^3$ are taken together to form an optionally substituted 5- or 6-membered ring. In some embodiments, $R^2$ and $R^3$ are taken together to form an optionally substituted 5- or 6-membered ring optionally containing one or more additional heteroatoms. In some embodiments, $R^1$, $R^2$ and $R^3$ are taken together to form an optionally substituted fused ring system. In some embodiments, such rings formed by combinations of any of $R^1$, $R^2$ and $R^3$ are partially unsaturated or aromatic.

In some embodiments, a cationic functional group is a quaternary ammonium group:

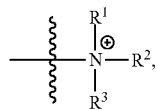

where each of $R^1$, $R^2$, and $R^3$ is as defined above and described in classes and subclasses herein. In certain embodiments, $R^1$, $R^2$, and $R^3$ are all methyl. In certain embodiments, $R^1$, $R^2$, and $R^3$ are all ethyl. In certain embodiments, $R^1$, $R^2$, and $R^3$ are all n-butyl. In some embodiments, $R^3$ is hydroxyl, thereby forming a substituted hydroxylamine or N-oxide.

In certain embodiments, a cationic functional group is a protonated amine:

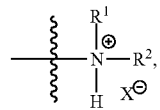

where each of $R^1$ and $R^2$ is as defined above and described in classes and subclasses herein.

In specific embodiments, a protonated amine cationic functional group is selected from the group consisting of:

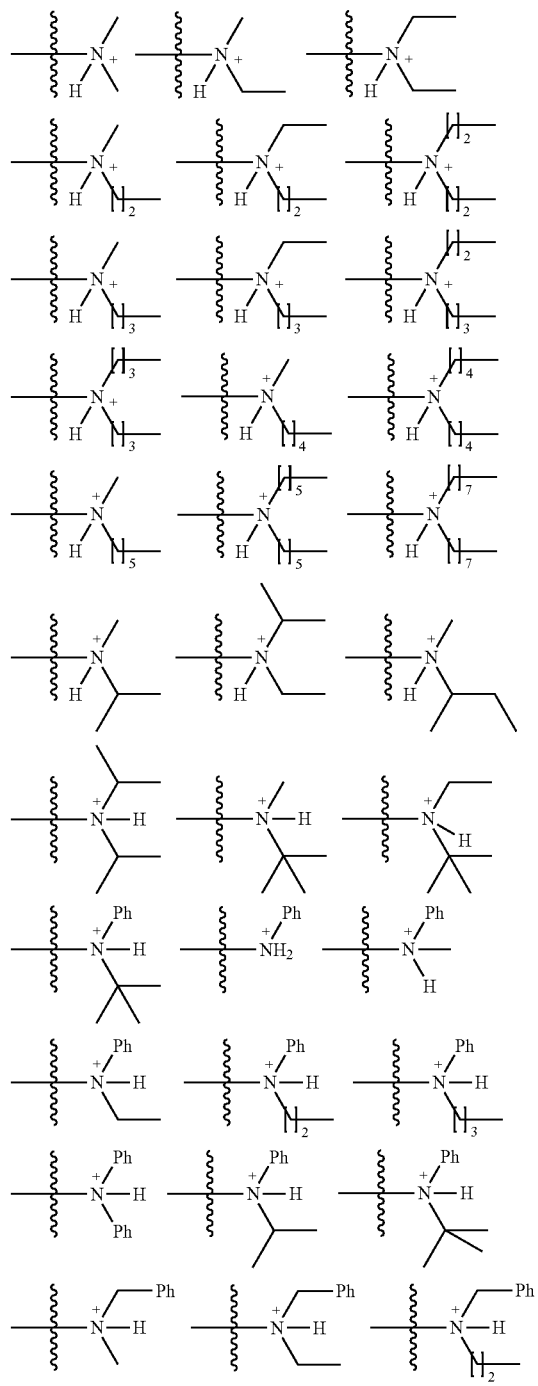

-continued

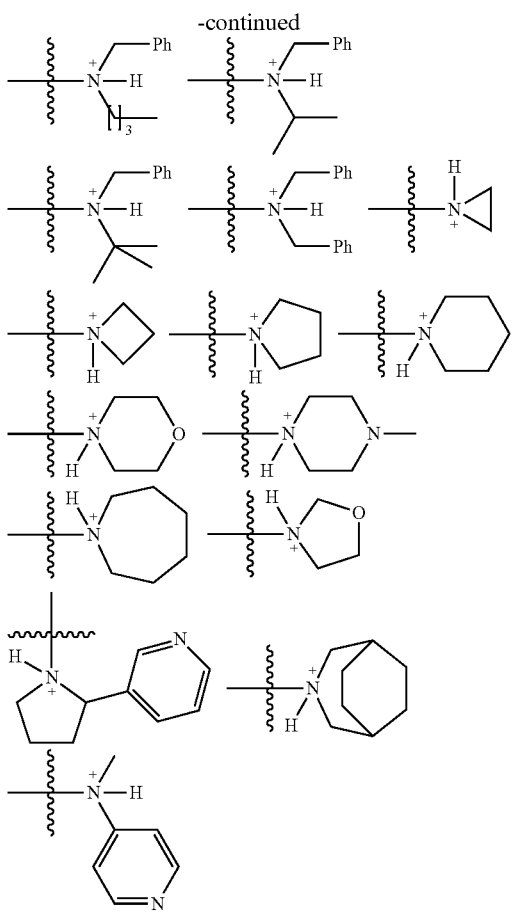

In certain embodiments, a cationic functional group is a guanidinium group:

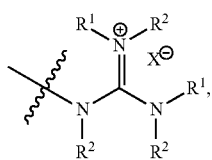

wherein each $R^1$ and $R^2$ is independently as defined above and described in classes and subclasses herein. In some embodiments, each $R^1$ and $R^2$ is independently hydrogen or $C_{1-20}$ aliphatic. In some embodiments, each $R^1$ and $R^2$ is independently hydrogen or $C_{1-12}$ aliphatic. In some embodiments, each $R^1$ and $R^2$ is independently hydrogen or $C_{1-20}$ heteroaliphatic. In some embodiments, each $R^1$ and $R^2$ is independently hydrogen or phenyl. In some embodiments, each $R^1$ and $R^2$ is independently hydrogen or 8- to 10-membered aryl. In some embodiments, each $R^1$ and $R^2$ is independently hydrogen or 5- to 10-membered heteroaryl. In some embodiments, each $R^1$ and $R^2$ is independently hydrogen or 3- to 7-membered heterocyclic. In some embodiments, one or more of $R^1$ and $R^2$ is optionally substituted $C_{1-12}$ aliphatic.

In some embodiments, any two or more $R^1$ or $R^2$ groups are taken together with intervening atoms to form one or more optionally substituted carbocyclic, heterocyclic, aryl, or heteroaryl rings. In certain embodiments, $R^1$ and $R^2$ groups are taken together to form an optionally substituted 5- or 6-membered ring. In some embodiments, three or more $R^1$ and/or $R^2$ groups are taken together to form an optionally substituted fused ring system.

In certain embodiments, a $R^1$ and $R^2$ group are taken together with intervening atoms to form a compound selected from:

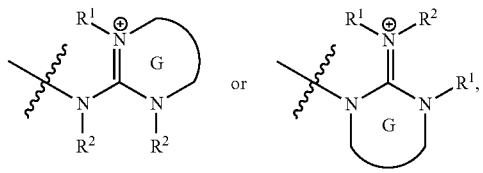

wherein each $R^1$ and $R^2$ is independently as defined above and described in classes and subclasses herein, and Ring G is an optionally substituted 5- to 7-membered saturated or partially unsaturated heterocyclic ring.

In certain embodiments, two or more $R^1$ and $R^2$ groups are taken together with intervening atoms to form a compound selected from:

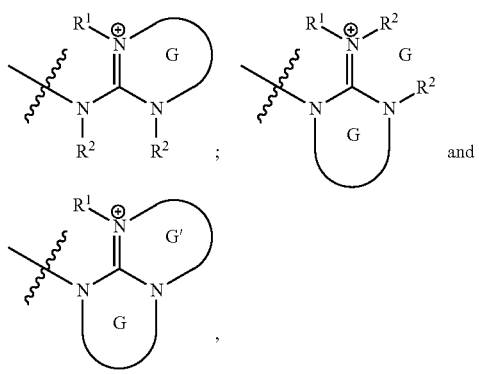

wherein each $R^1$ and $R^2$ is independently as defined above and described in classes and subclasses herein, and Ring G is an optionally substituted 5- to 8-membered saturated or partially unsaturated heterocyclic ring.

It will be appreciated that when a guanidinium cation is depicted as

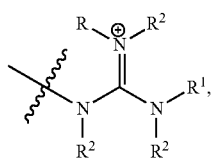

all resonance forms are contemplated and encompassed by the present disclosure. For example, such groups can also be depicted as

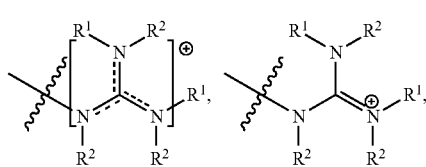

-continued

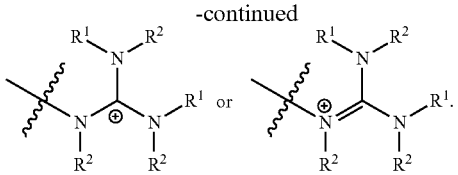

In specific embodiments, a guanidinium cationic functional group is selected from the group consisting of:

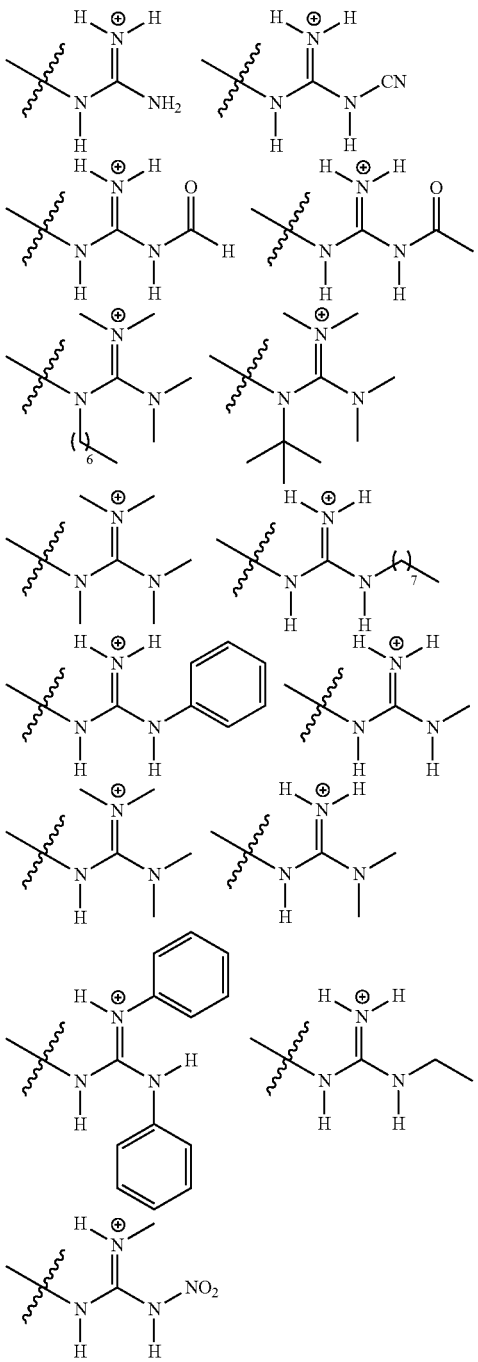

In certain embodiments, a guanidinium cationic functional group is selected from the group consisting of:

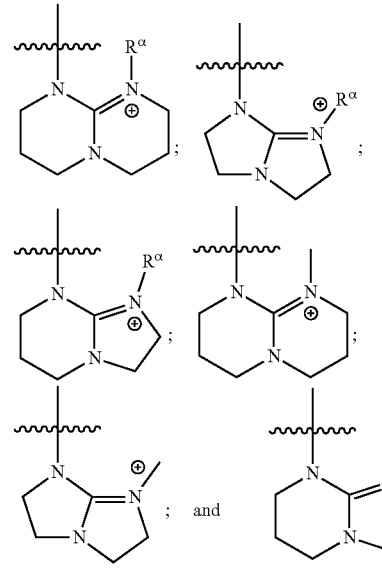

where $R^\alpha$ is selected from the group consisting of —H, optionally substituted $C_{1-12}$ aliphatic, and optionally substituted aryl.

In some embodiments, a cationic functional group is a phosphonium group

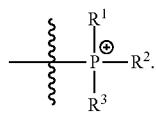

In certain embodiments, $R^1$, $R^2$, and $R^3$ are independently selected from the group consisting of optionally substituted $C_1$-$C_{12}$ aliphatic, optionally substituted $C_6$-$C_{10}$ aryl, and optionally substituted $C_1$-$C_{10}$ heterocyclic. In certain embodiments, $R^1$, $R^2$, and $R^3$ are phenyl. In certain embodiments, $R^1$, $R^2$, and $R^3$ are n-butyl. In certain embodiments, $R^1$, $R^2$, and $R^3$ are methyl.

In some embodiments, the cationic functional group is an arsonium group.

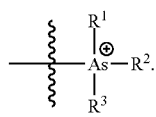

In some embodiments, each occurrence of $R^1$, $R^2$, and $R^3$ is independently hydrogen or optionally substituted $C_{1-20}$ aliphatic. In some embodiments, each occurrence of $R^1$, $R^2$, and $R^3$ is independently hydrogen or optionally substituted $C_{1-20}$ heteroaliphatic having 1-4 heteroatoms independently selected from the group consisting of nitrogen, oxygen, and sulfur. In some embodiments, each occurrence of $R^1$, $R^2$, and $R^3$ is independently hydrogen or optionally substituted 6- to 10-membered aryl. In some embodiments, each occurrence of $R^1$, $R^2$, and $R^3$ is independently hydrogen or optionally substituted 5- to 10-membered heteroaryl having 1-4 heteroatoms independently selected from nitrogen, oxygen, or sulfur. In some embodiments, each occurrence of $R^1$, $R^2$, and $R^3$ is independently hydrogen or optionally substituted 4- to 7-membered heterocyclic having 1-2 heteroatoms independently selected from the group consisting of nitrogen, oxygen, and sulfur. In some embodiments, $R^1$ and $R^2$ are taken together with their intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally substituted $C_5$-$C_{10}$ heteroaryl.

In specific embodiments, an arsonium cationic functional group is selected from the group consisting of:

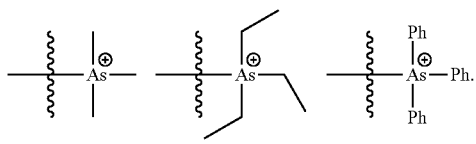

In some embodiments, a cationic functional group is a sulfonium group:

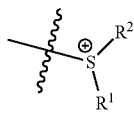

wherein each of $R^1$, $R^2$, and $R^3$ are as defined above and described in classes and subclasses herein.

In some embodiments, a cationic functional group is an optionally substituted nitrogen-containing heterocycle. In certain embodiments, the nitrogen-containing heterocycle is an aromatic heterocycle. In certain embodiments, the optionally substituted nitrogen-containing heterocycle is selected from the group consisting of: pyridine, imidazole, pyrrolidine, pyrazole, quinoline, thiazole, dithiazole, oxazole, triazole, pyrazolem, isoxazole, isothiazole, tetrazole, pyrazine, thiazine, and triazine.

In some embodiments, a nitrogen-containing heterocycle includes a quaternized nitrogen atom. In certain embodiments, a nitrogen-containing heterocycle includes an iminium moiety such as

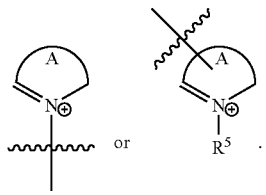

In certain embodiments, the optionally substituted nitrogen-containing heterocycle is selected from the group consisting of pyridinium, imidazolium, pyrrolidinium, pyrazolium, quinolinium, thiazolium, dithiazolium, oxazolium, triazolium, isoxazolium, isothiazolium, tetrazolium, pyrazinium, thiazinium, and triazinium.

In certain embodiments, a nitrogen-containing heterocycle is linked to a metal complex via a ring nitrogen atom. In some embodiments, a ring nitrogen to which the attachment is made is thereby quaternized, and in some embodiments, linkage to a metal complex takes the place of an N—H bond and the nitrogen atom thereby remains neutral. In certain embodiments, an optionally substituted N-linked nitrogen-containing heterocycle is a pyridinium derivative. In certain embodiments, optionally substituted N-linked nitrogen-containing heterocycle is an imidazolium derivative. In certain embodiments, optionally substituted N-linked nitrogen-containing heterocycle is a thiazolium derivative. In certain embodiments, optionally substituted N-linked nitrogen-containing heterocycle is a pyridinium derivative.

In some embodiments, a cationic functional group is

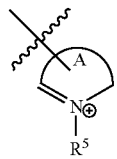

In certain embodiments, ring A is an optionally substituted, 5- to 10-membered heteroaryl group. In some embodiments, Ring A is an optionally substituted, 6-membered heteroaryl group. In some embodiments, Ring A is a ring of a fused heterocycle. In some embodiments, Ring A is an optionally substituted pyridyl group.

In some embodiments, when Z is

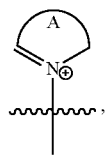

ring A is other than an imidazole, an oxazole, or a thiazole.

In specific embodiments, a nitrogen-containing heterocyclic cationic functional group is selected from the group consisting of:

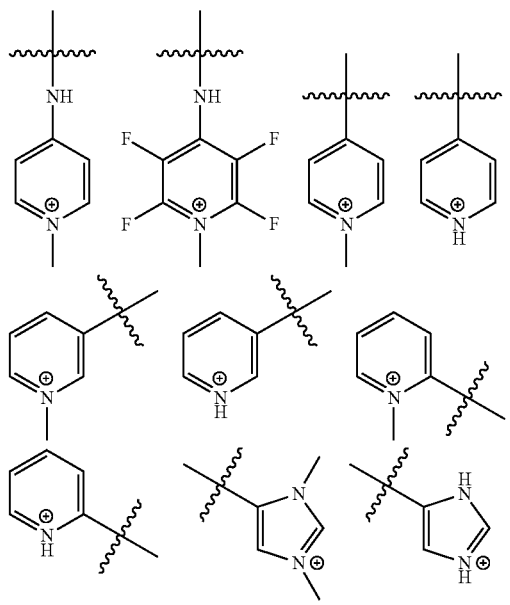

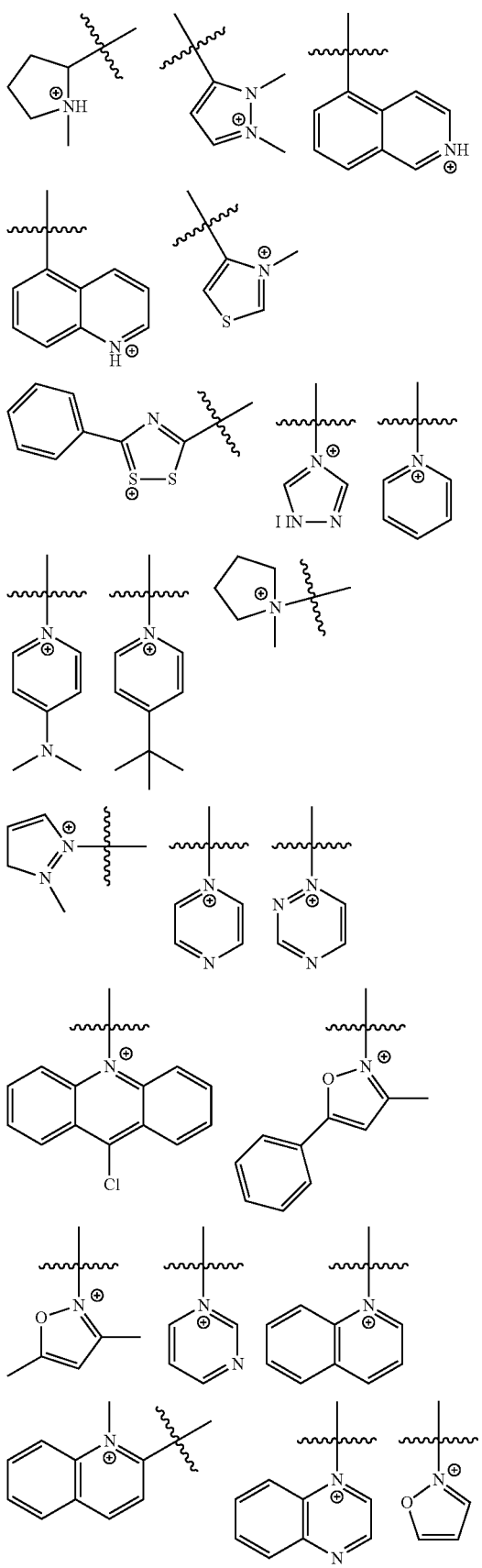

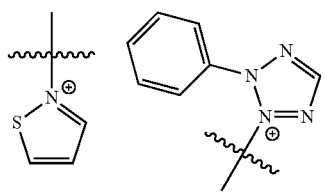

In certain embodiments, Ring B is a 5-membered saturated or partially unsaturated monocyclic heterocyclic ring. In certain embodiments, Ring B is a 6-membered saturated or partially unsaturated heterocycle. In certain embodiments, Ring B is a 7-membered saturated or partially unsaturated heterocycle. In certain embodiments, Ring B is tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. In some embodiments, Ring B is piperidinyl.

In some embodiments, a cationic functional group is an N-linked amidinium group such as:

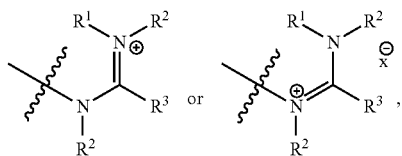

where each $R^1$, $R^2$, and $R^3$ is independently as defined above and described in classes and subclasses herein. In certain embodiments, an N-linked amidinium cation comprises a cyclic amidine such as an imidazolium group. In certain embodiments, an N-linked amidinium cation comprises a bicyclic amidinium group. In certain embodiments, such a group comprises:

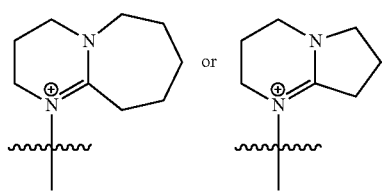 [SMILES: *[N+]1=C2CCCCCN2CCC1 ; *[N+]1=C2CCCN2CCC1]

In some embodiments, a cationic functional group is a C-linked amidinium group

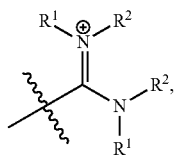

wherein each $R^1$ and $R^2$ is independently as defined above and described in classes and subclasses herein.

In some embodiments, a cationic functional group is

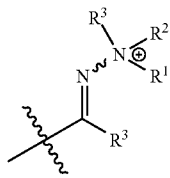

wherein each $R^1$, $R^2$, and $R^3$ is independently as defined above and described in classes and subclasses herein.

In some embodiments, a cationic functional group is

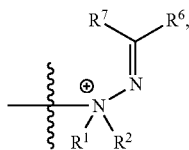

wherein each of $R^1$, $R^2$, $R^6$, and $R^7$ is as defined above and described in classes and subclasses herein.

In certain embodiments, $R^6$ and $R^7$ are each independently an optionally substituted group selected from the group consisting of $C_{1-20}$ aliphatic; $C_{1-20}$ heteroaliphatic; phenyl, and 8-10-membered aryl. In some embodiments, $R^6$ and $R^7$ are each independently an optionally substituted $C_{1-20}$ aliphatic. In some embodiments, $R^6$ and $R^7$ are each independently an optionally substituted $C_{1-20}$ heteroaliphatic having. In some embodiments, $R^6$ and $R^7$ are each independently an optionally substituted phenyl or 8-10-membered aryl. In some embodiments, $R^6$ and $R^7$ are each independently an optionally substituted 5- to 10-membered heteroaryl. In some embodiments, $R^6$ and $R^7$ can be taken together with intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally substituted 5- to 10-membered heteroaryl. In some embodiments, $R^6$ and $R^7$ are each independently an optionally substituted $C_{1-6}$ aliphatic. In some embodiments, each occurrence of $R^6$ and $R^7$ is independently methyl, ethyl, propyl, butyl, pentyl, hexyl, heptyl, octyl, or benzyl. In some embodiments, each occurrence of $R^6$ and $R^7$ is independently perfluoro. In some embodiments, each occurrence of $R^6$ and $R^7$ is independently —$CF_2CF_3$.

In some embodiments, a cationic functional group is

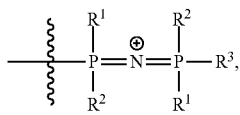

where each of $R^1$, $R^2$, and $R^3$ is as defined above and in the classes and subclasses herein. In certain embodiments, $R^1$, $R^2$, and $R^3$ are each independently selected from the group consisting of optionally substituted $C_1$-$C_{12}$ aliphatic, optionally substituted $C_6$-$C_{10}$ aryl, and optionally substituted $C_1$-$C_{10}$ heterocyclic. In certain embodiments, $R^1$, $R^2$, and $R^3$ are each phenyl.

In some embodiments, a cationic functional group is

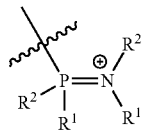

wherein each $R^1$ and $R^2$ is independently as defined above and described in classes and subclasses herein.

In some embodiments, a cationic functional group is

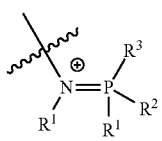

wherein each $R^1$, $R^2$, and $R^3$ is independently as defined above and described in classes and subclasses herein.

In some embodiments, a cationic functional group is

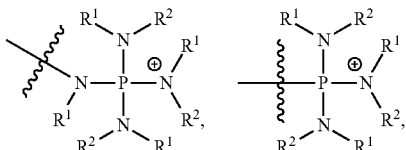

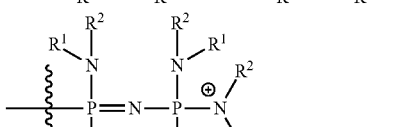

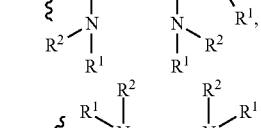

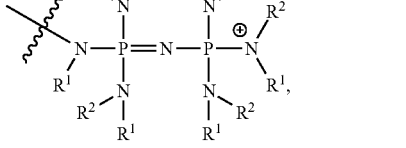

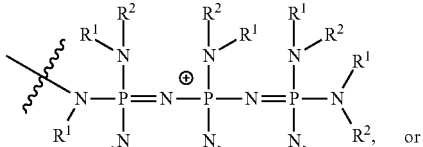

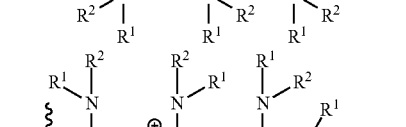, or

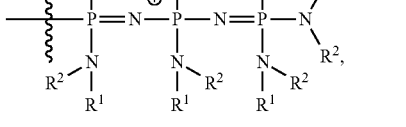

wherein each $R^1$ and $R^2$ is independently as defined above and described in classes and subclasses herein.

In some embodiments, a cationic functional group is

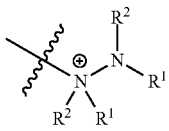

wherein each R¹ and R² is independently as defined above and described in classes and subclasses herein.

In some embodiments, a cationic functional group is

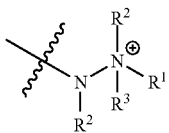

wherein each R¹, R², and R³ is independently as defined above and described in classes and subclasses herein.

In some embodiments, a cationic functional group is

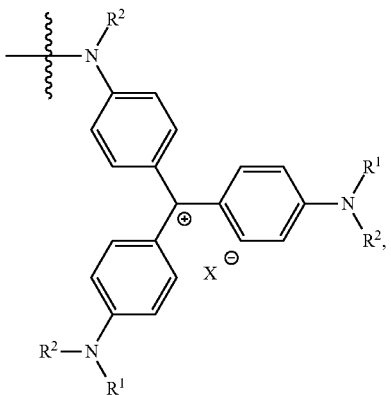

wherein each R¹ and R² is independently as defined above and described in classes and subclasses herein.

II. Metal Complexes

As described above, the catalysts of the present invention comprise one or more ligands. While many examples and embodiments herein are focused on the presence of a single multidentate ligand, this is not a limiting principle of the present invention and it is to be understood that two or more mono- or multidentate ligands may also be used, when two or more ligands are used, they need not all be substituted with tethered cationic functional moieties, only one ligand may be so substituted, or more than one may be substituted with one or more cationic functional moieties.

Suitable multidentate ligands include, but are not limited to: porphyrin derivatives 1, salen derivatives 2, dibenzotetramethyltetraaza[14]annulene (tmtaa) derivatives 3, phthalocyaninate derivatives 4, derivatives of the Trost ligand 5, and tetraphenylporphyrin derivatives 6. In certain embodiments, the multidentate ligand is a salen derivative. In other embodiments, the multidentate ligand is a tetraphenylporphyrin derivative.

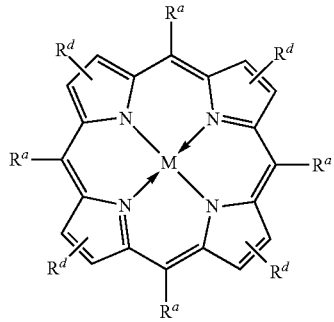

1

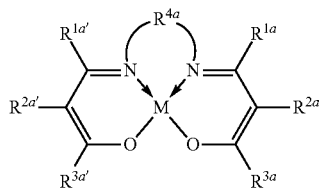

2

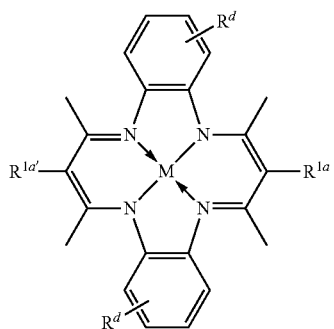

3

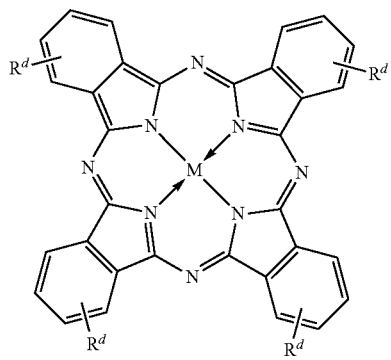

4

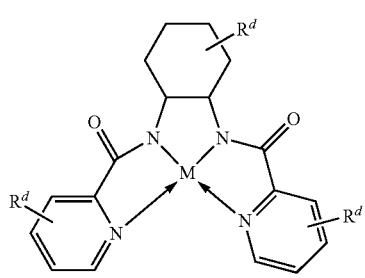

5

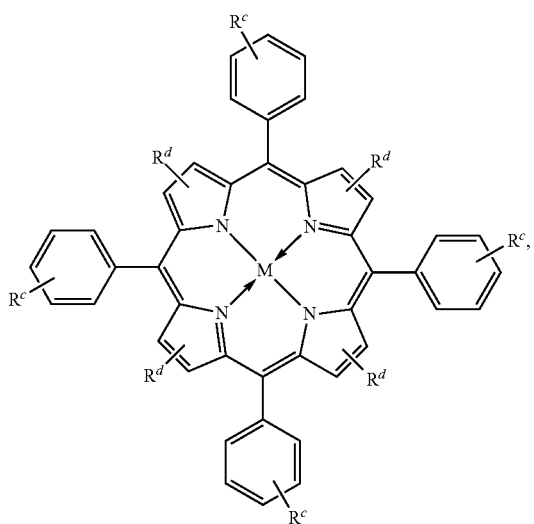

where each of $R^c$, $R^d$, $R^a$, $R^{1a}$, $R^{2a}$, $R^{3a}$, $R^{1a'}$, $R^{2a'}$, $R^{3a'}$, and m, is as defined and described in the classes and subclasses herein.

In certain embodiments, catalysts of the present invention comprise metal-porphinato complexes. In certain embodiments, the moiety ⊕ has the structure:

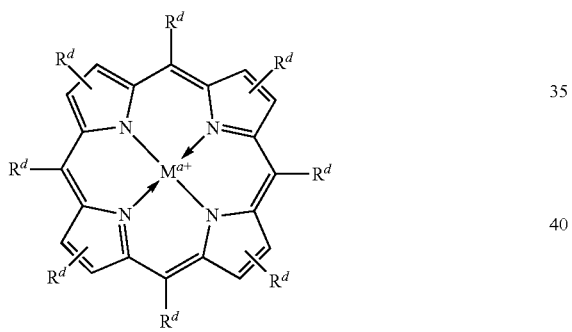

where each of M and a is as defined above and described in the classes and subclasses herein, and $R^d$ at each occurrence is independently a cationic functional moiety ( —$(Z^+)_b$ ), hydrogen, halogen, —$OR^4$, —$NR_2^y$, —SR, —CN, —$NO_2$, —$SO_2R^y$, —$SOR^y$, —$SO_2NR_2^y$; —CNO, —$NRSO_2R^y$, —NCO, —$N_3$, —$SiR_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, or sulfur; and 4- to 7-membered heterocyclic having 1-2 heteroatoms independently selected from the group consisting of nitrogen, oxygen, and sulfur, where two or more $R^d$ groups may be taken together to form one or more optionally substituted rings, where each $R^y$ is independently hydrogen, an optionally substituted group selected the group consisting of acyl; carbamoyl, arylalkyl; 6- to 10-membered aryl; $C_{1-12}$ aliphatic; $C_{1-12}$ heteroaliphatic having 1-2 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; an oxygen protecting group; and a nitrogen protecting group; two $R^y$ on the same nitrogen atom are taken with the nitrogen atom to form an optionally substituted 4- to 7-membered heterocyclic ring having 0-2 additional heteroatoms independently selected from the group consisting of nitrogen, oxygen, and sulfur; and each $R^4$ a hydroxyl protecting group or $R^y$;

In certain embodiments, the multidentate ligand is a porphyrin moiety. Examples include, but are not limited to:

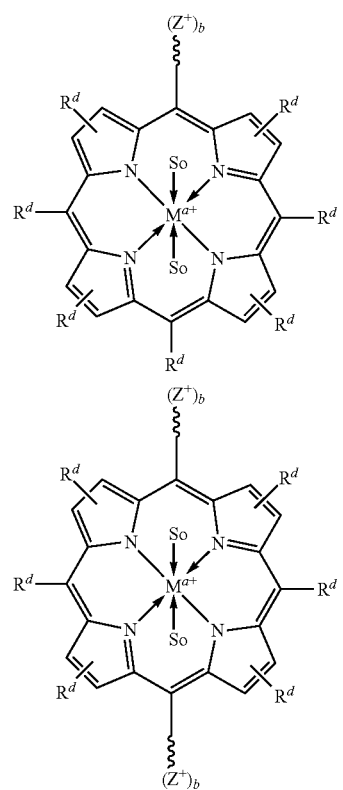

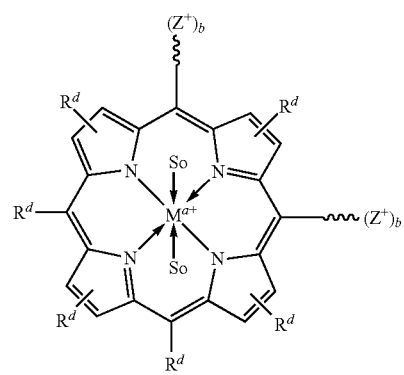

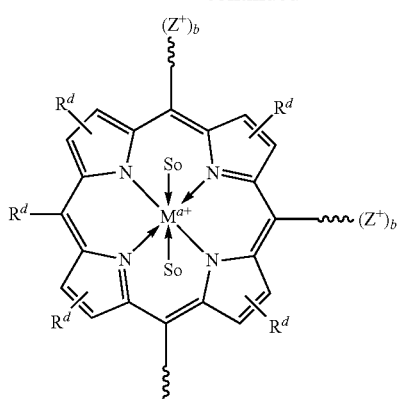

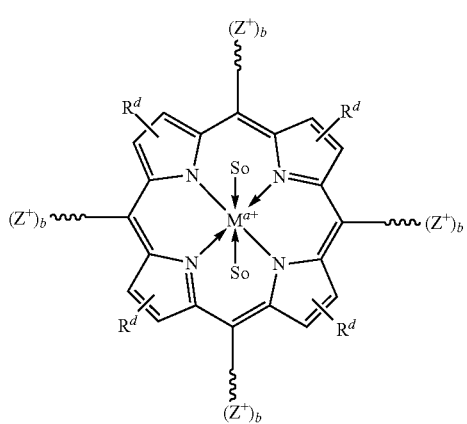

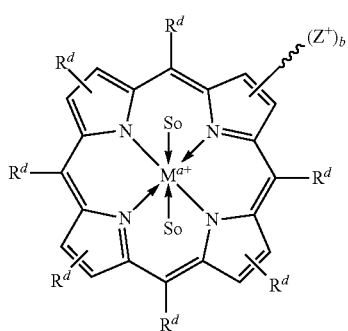

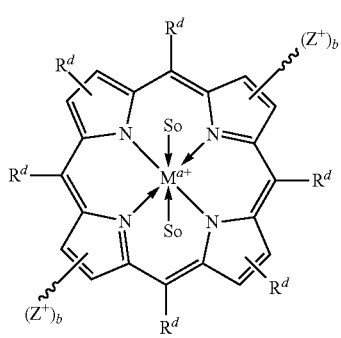

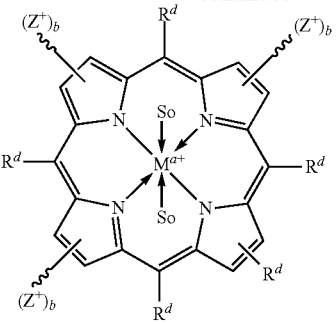

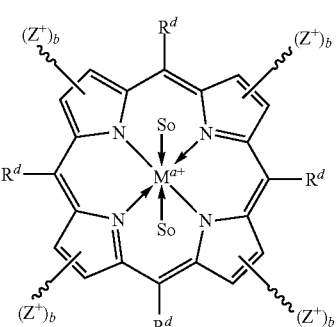

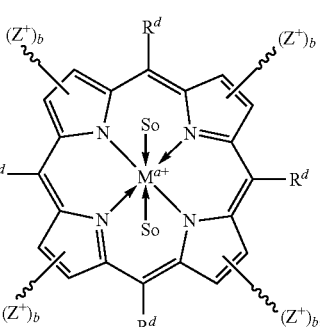

where M, a and $R^d$ are as defined above and in the classes and subclasses herein, and So, is an optionally present coordinated solvent molecule, such as an ether, epoxide, DMSO, amine or other Lewis basic moiety.

In certain embodiments, the moiety ⊕ has the structure:

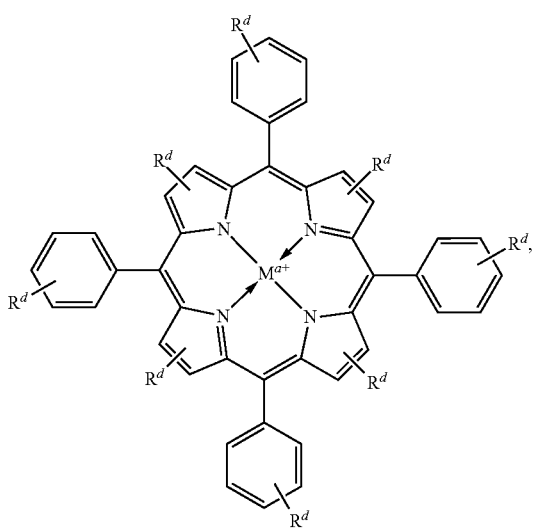

where M, a and $R^d$ are as defined above and in the classes and subclasses herein.

In certain embodiments, the multidentate ligand is an optionally substituted tetraphenyl porphyrin. Suitable examples include, but are not limited to:

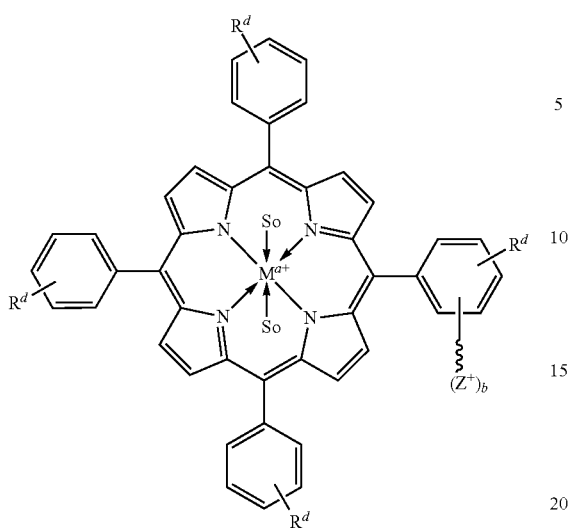
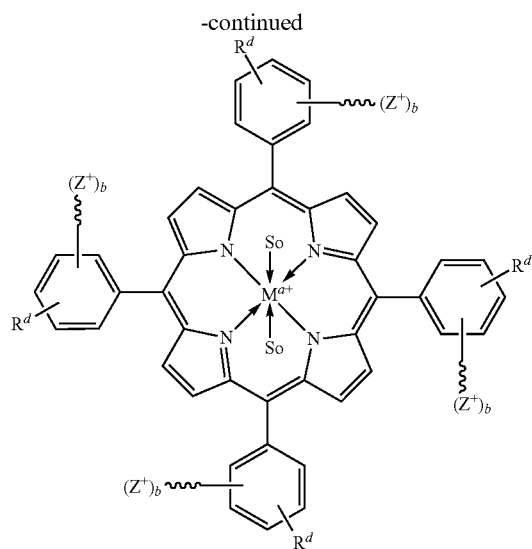
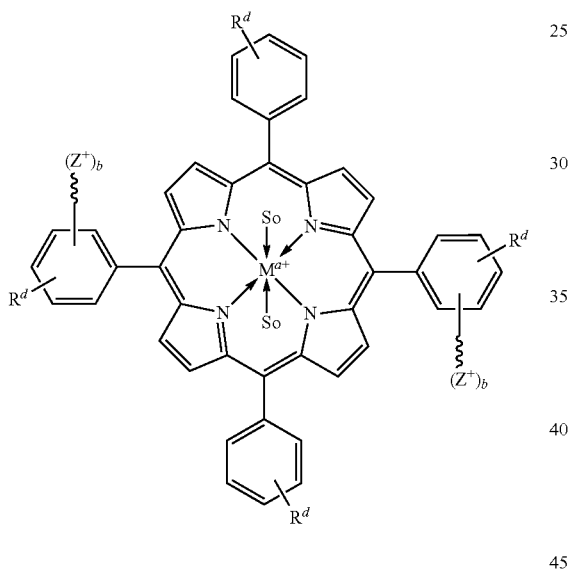
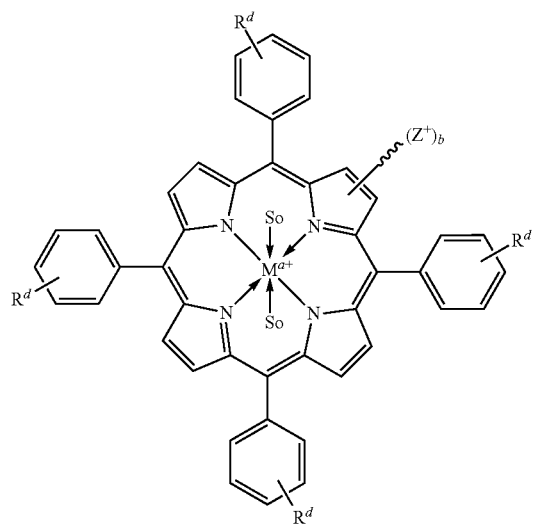
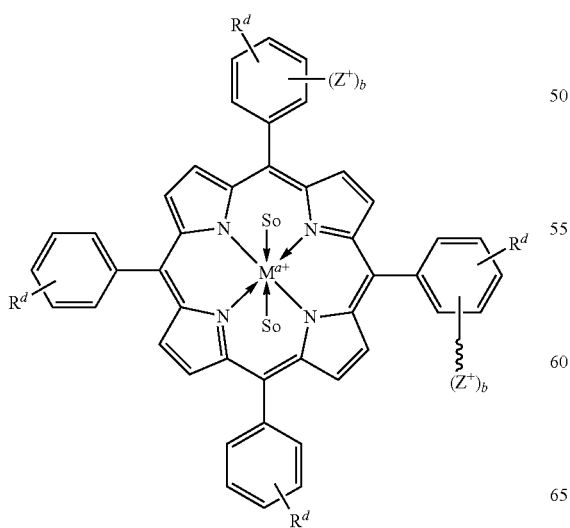
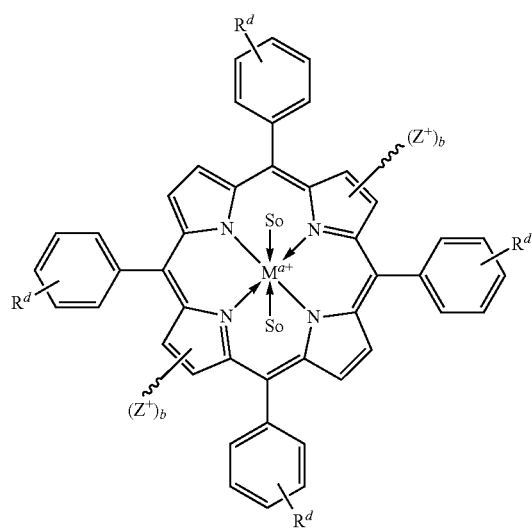

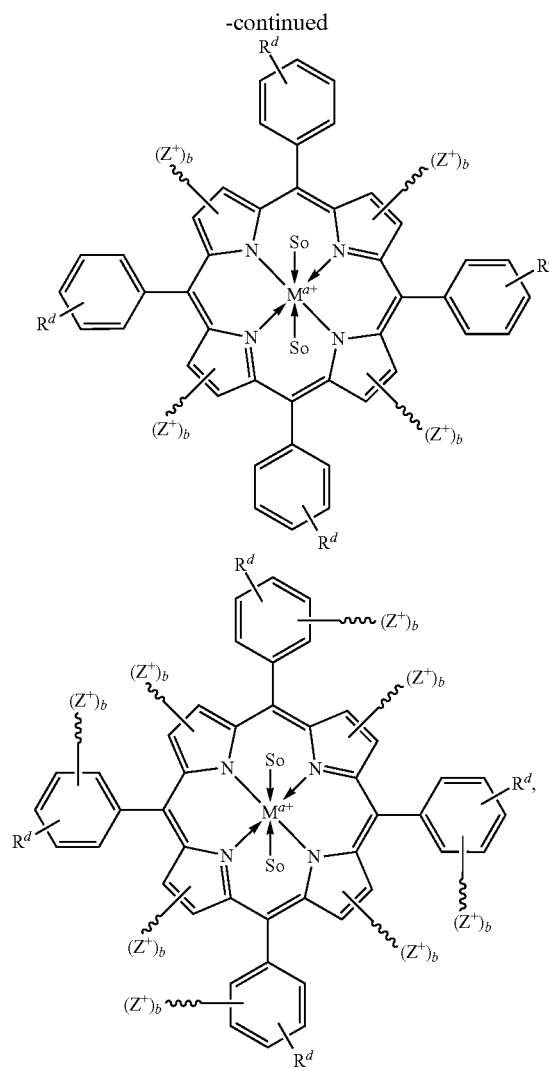

where M, a, R, So and ⎯⎯(Z⁺)ᵦ are as defined above and described in the classes and subclasses herein.

In certain embodiments, the moiety ⊕ has the structure:

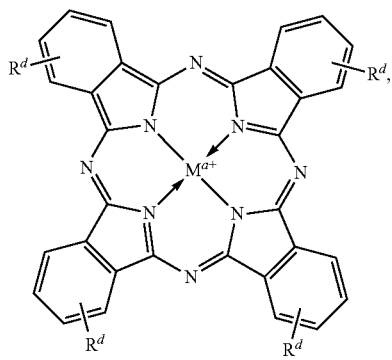

where M, a and $R^d$ are as defined above and in the classes and subclasses herein.

In certain embodiments, catalysts of the present invention comprise metallo salenate complexes. In certain embodiments, the moiety ⊕ has the structure:

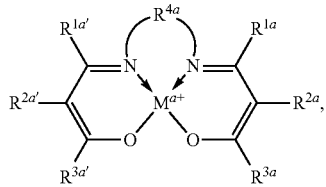

wherein:
M, and a are as defined above and in the classes and subclasses herein.

$R^{1a}$, $R^{1a'}$, $R^{2a}$, $R^{2a'}$, $R^{3a}$, and $R^{3a'}$ are independently a cationic functional moiety ( ⎯⎯(Z⁺)ᵦ ), hydrogen, halogen, —OR⁴, —NR₂ʸ, —SR, —CN, —NO₂, —SO₂Rʸ, —SOR, —SO₂NR₂ʸ; —CNO, —NRSO₂Rʸ, —NCO, —N₃, —SiR₃; or an optionally substituted group selected from the group consisting of C₁₋₂₀ aliphatic; C₁₋₂₀ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, or sulfur; and 4- to 7-membered heterocyclic having 1-2 heteroatoms independently selected from the group consisting of nitrogen, oxygen, and sulfur; wherein each R, R⁴, and Rʸ is independently as defined above and described in classes and subclasses herein, wherein any of ($R^{2a'}$ and $R^{3a'}$), ($R^{2a}$ and $R^{3a}$), ($R^{1a}$ and $R^{2a}$), and ($R^{1a'}$ and $R^{2a'}$) may optionally be taken together with the carbon atoms to which they are attached to form one or more rings which may in turn be substituted with one or more R groups; and $R^{4a}$ is selected from the group consisting of:

e)

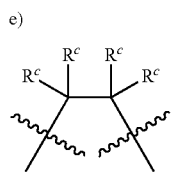

f)

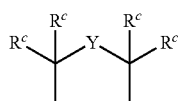

g)

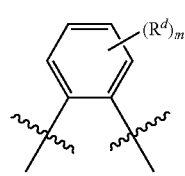

and h)

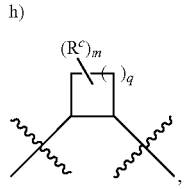

where

R$^c$ at each occurrence is independently a cationic functional moiety ( 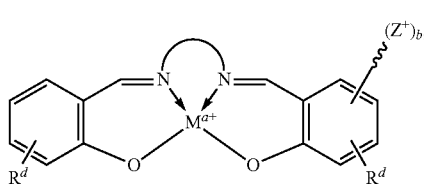 ), hydrogen, halogen, —OR, —NR$_2^y$, —SR$^y$, —CN, —NO$_2$, —SO$_2$R$^y$, —SOR$^y$, —SO$_2$NR$_2^y$; —CNO, —NRSO$_2$R$^y$, —NCO, —N$_3$, —SiR$_3$; or an optionally substituted group selected from the group consisting of C$_{1-20}$ aliphatic; C$_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, or sulfur; and 4- to 7-membered heterocyclic having 1-2 heteroatoms independently selected from the group consisting of nitrogen, oxygen, and sulfur;

where:
  two or more R$^c$ groups may be taken together with the carbon atoms to which they are attached and any intervening atoms to form one or more rings;
  when two R$^c$ groups are attached to the same carbon atom, they may be taken together along with the carbon atom to which they are attached to form a moiety selected from the group consisting of: a 3- to 8-membered spirocyclic ring, a carbonyl, an oxime, a hydrazone, an imine;

Y is a divalent linker selected from the group consisting of: —NR$^y$—, —N(R)C(O)—, —C(O)NR$^y$—, —O—, —C(O)—, —OC(O)—, —C(O)O—, —S—, —SO—, —SO$_2$—, —C(=S)—, —C(=NR$^y$)—, —N=N—; a polyether; a C$_3$ to C$_8$ substituted or unsubstituted carbocycle; and a C$_1$ to C$_8$ substituted or unsubstituted heterocycle;

m' is 0 or an integer from 1 to 4, inclusive;
q is 0 or an integer from 1 to 4, inclusive; and
x is 0, 1, or 2.

In certain embodiments, a provided metal complex comprises at least one cationic functional moiety tethered to a carbon atom of only one phenyl ring of the salicylaldehyde-derived portion of a salen ligand, as shown in formula Ia:

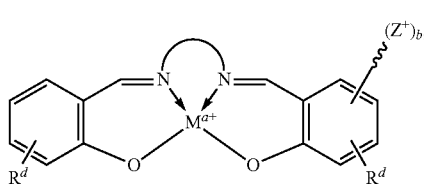

Ia wherein each of 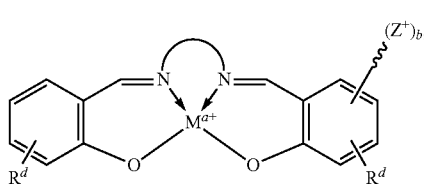(Z$^+$)$_b$ , M, R$^d$, and a, is as defined above and in the classes and subclasses herein, ⌒ represents is an optionally substituted moiety linking the two nitrogen atoms of the diamine portion of the salen ligand, where ⌒ is selected from the group consisting of a C$_3$-C$_{14}$ carbocycle, a C$_6$-C$_{10}$ aryl group, a C$_3$-C$_{14}$ heterocycle, and a C$_5$-C$_{10}$ heteroaryl group; or an optionally substituted C$_{2-20}$ aliphatic group, wherein one or more methylene units are optionally and independently replaced by —NR$^y$—, —N(R$^y$)C(O)—, —C(O)N(R$^y$)—, —OC(O)N(R$^y$)—, —N(R$^y$)C(O)O—, —OC(O)O—, —O—, —C(O)—, —OC(O)—, —C(O)O—, —S—, —SO—, —SO$_2$—, —C(=S)—, —C(=NR$^y$)—, —C(=NOR$^y$)— or —N=N—.

In certain embodiments, provided metal complexes of the present invention feature cationic functional moieties tethered to only one salicylaldehyde-derived portion of the salen ligand, while in other embodiments both salicylaldehyde-derived portions of the salen ligand bear one or more cationic functional moieties as in IIa:

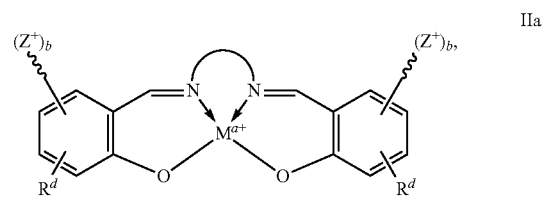

IIa where each of M, a, So, R$^d$, ⌒, and 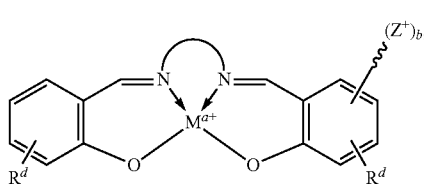(Z$^1$)$_b$ are as defined above and in the classes and subclasses herein.

In certain embodiments of metal complexes having formulae Ia or IIa above, at least one of the phenyl rings comprising the salicylaldehyde-derived portion of the metal complex is independently selected from the group consisting of:

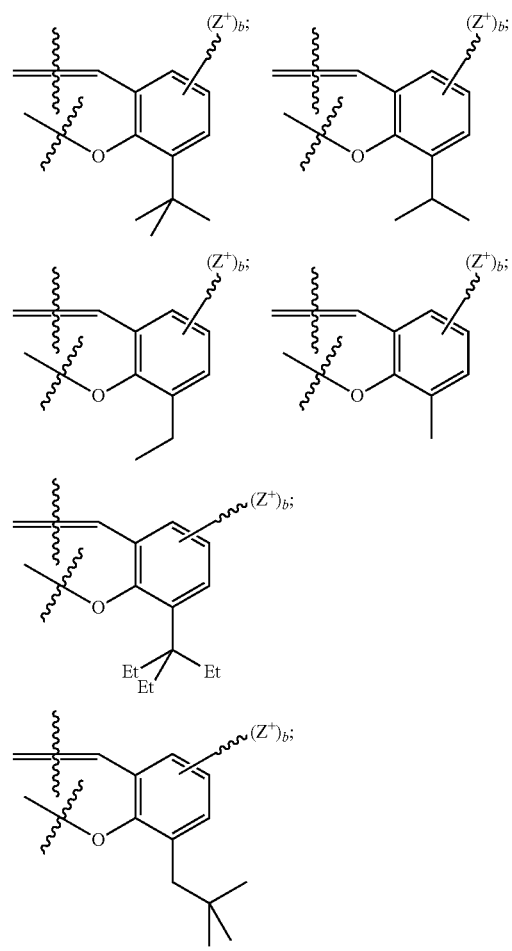

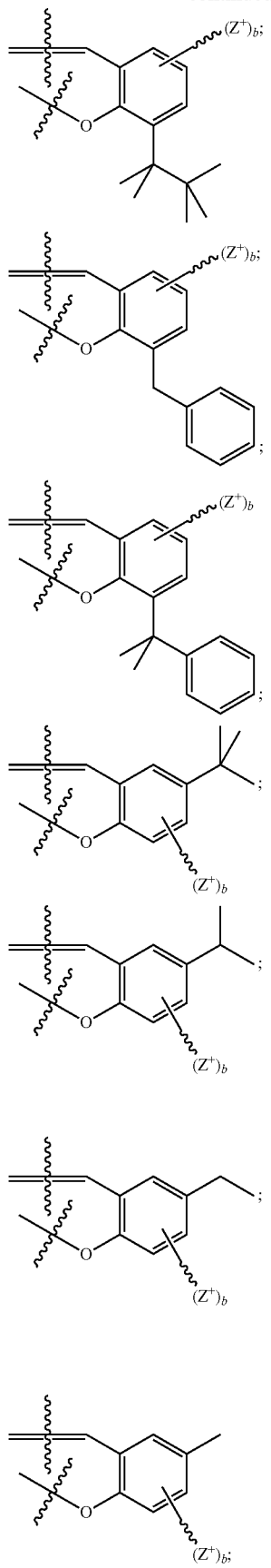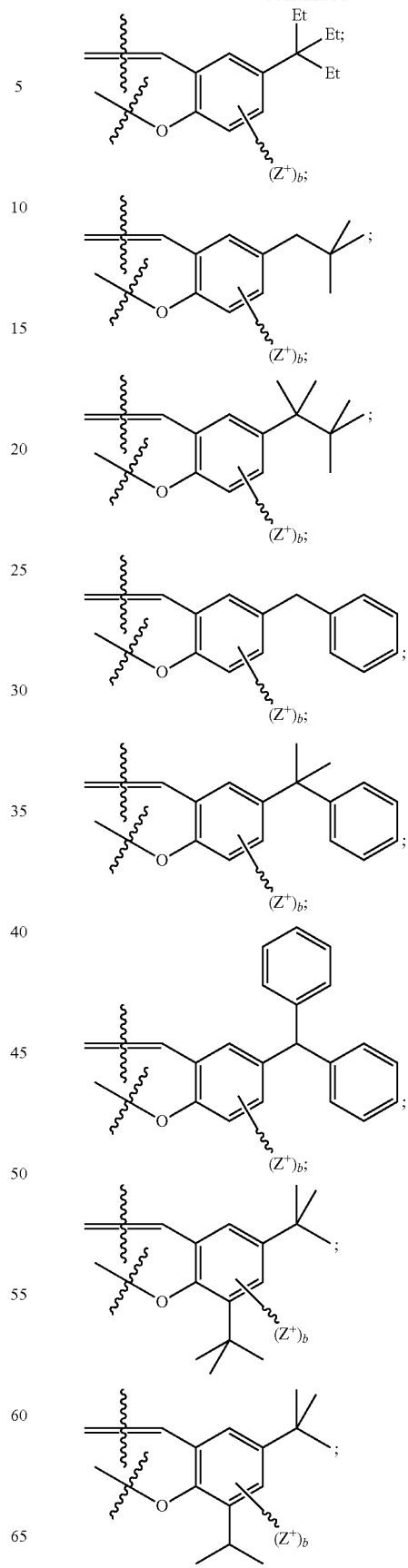

-continued

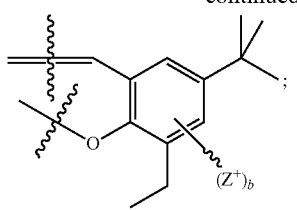

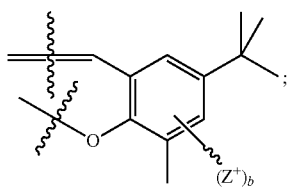

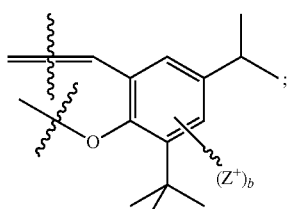

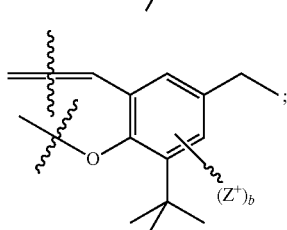

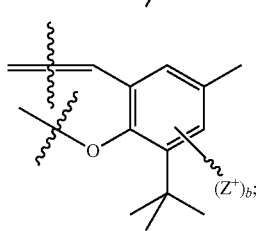

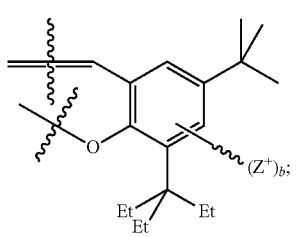

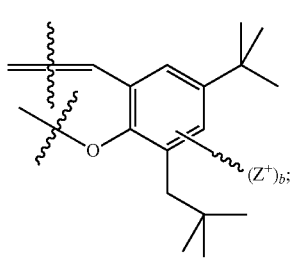

-continued

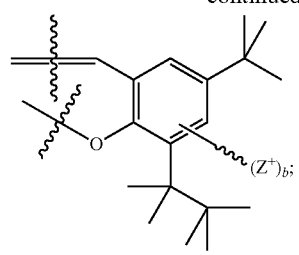

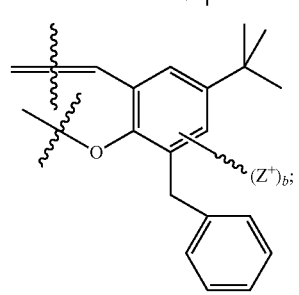

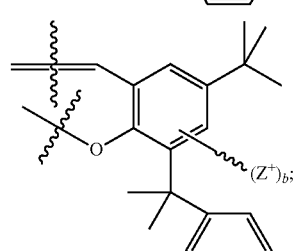

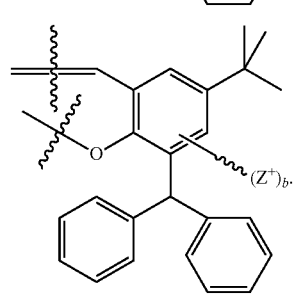

and

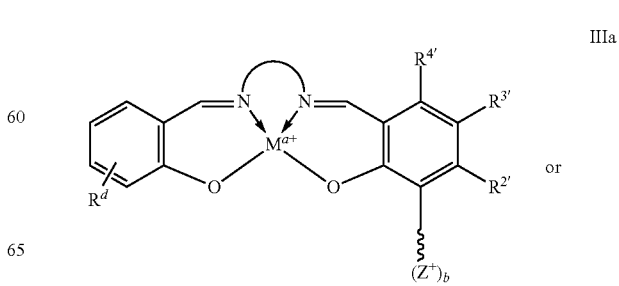

where $\text{---}\!\!\sim\!\!(Z^1)_b$ represents one or more independently-defined cationic functional moieties which may be bonded to any one or more of the unsubstituted positions of the salicylaldehyde-derived phenyl ring.

In certain embodiments, there is a cationic functional moiety tethered to the position ortho to the metal-bound oxygen substituent of one or both of the salicylaldehyde-derived phenyl rings of the salen ligand as in formulae IIIa and IIIb:

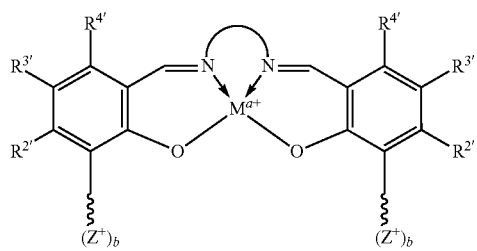

IIIb where each of M, a, $R^d$, ⌒, and ⌇⌇⌇$(Z^+)_b$ is as defined above, and in the classes and subclasses herein, and $R^{2'}$, $R^{3'}$, and $R^{4'}$, are independently at each occurrence selected from the group consisting of: hydrogen, halogen, —$NO_2$, —CN, —$SR^y$, —$S(O)R^y$, —$S(O)_2R^y$, —$NR^yC(O)R^y$, —$OC(O)R^y$, —$CO_2R^y$, —NCO, —$N_3$, —$OR^4$, —$OC(O)N(R^y)_2$, —$N(R^y)_2$, —$NR^yC(O)R^y$, —$NR^yC(O)OR^y$; $SiR_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, or sulfur; and 4- to 7-membered heterocyclic having 1-2 heteroatoms independently selected from the group consisting of nitrogen, oxygen, and sulfur, where two or more adjacent R groups can be taken together to form an optionally substituted saturated, partially unsaturated, or aromatic 5- to 12-membered ring containing 0 to 4 heteroatoms, where $R^y$ is as defined above In certain embodiments of metal complexes having formulae IIIa or IIIb, $R^{2'}$ and $R^{4'}$ are each hydrogen, and each $R^{3'}$ is, independently, —H, or optionally substituted $C_1$-$C_{20}$ aliphatic.

In certain embodiments of metal complexes IIIa and IIIb, at least one of the phenyl rings comprising the salicylaldehyde-derived portion of the metal complex is independently selected from the group consisting of:

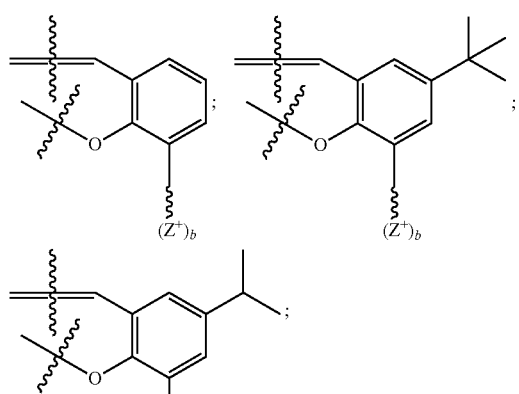

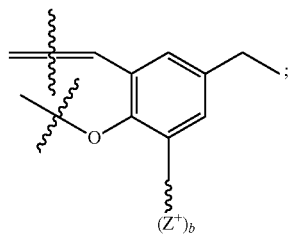

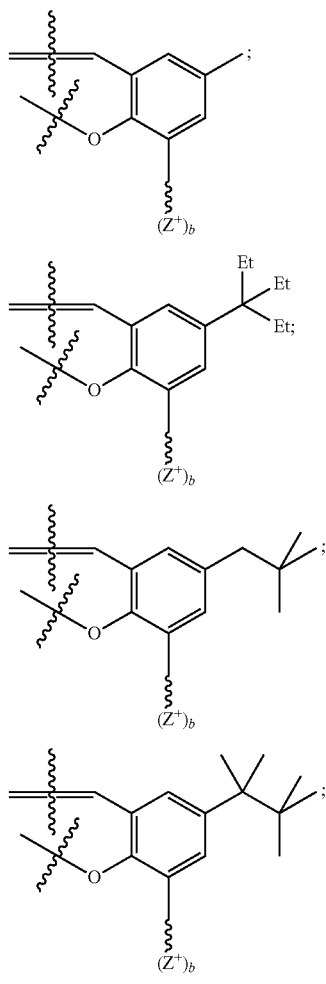

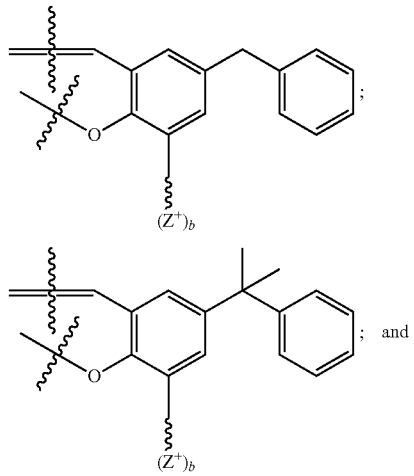

-continued

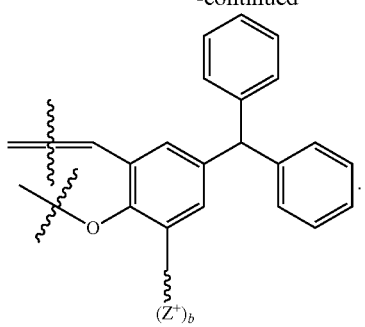

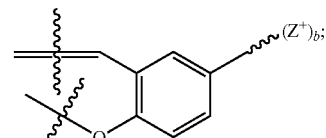

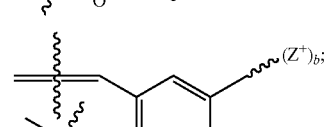

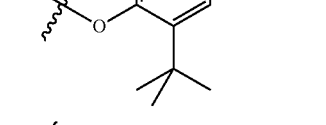

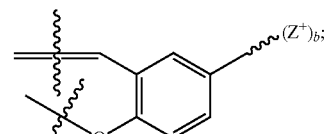

In other embodiments, there is a cationic functional moiety tethered to the position para to the phenolic oxygen of one or both of the salicylaldehyde-derived phenyl rings of the salen ligand as in structures IVa and IVb:

IVa

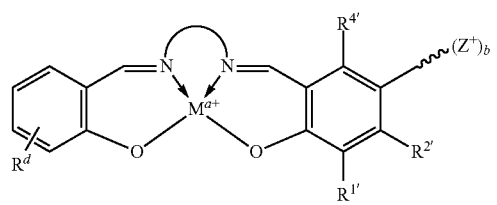

or

IVb

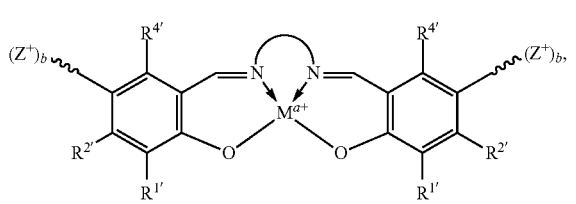

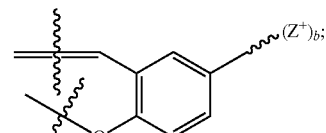

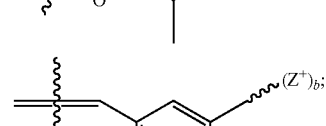

where each $R^{1'}$ is independently selected from the group consisting of: hydrogen, halogen, —$NO_2$, —CN, —$SR^y$, —S(O)$R^y$, —S(O)$_2R^y$, —$NR^yC(O)R^y$, —OC(O)$R^y$, —$CO_2R^y$, —NCO, —$N_3$, —$OR^y$, —OC(O)N($R^y$)$_2$, —N($R^y$)$_2$, —$NR^yC(O)R^y$, —$NR^yC(O)OR^y$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, or sulfur; and 4- to 7-membered heterocyclic having 1-2 heteroatoms independently selected from the group consisting of nitrogen, oxygen, and sulfur, where adjacent $R^{1'}$ and $R^{2'}$ groups can be taken together to form an optionally substituted saturated, partially unsaturated, or aromatic 5- to 12-membered ring containing 0 to 4 heteroatoms, In certain embodiments of metal complexes having formulae IVa or IVb, $R^{2'}$ and $R^{4'}$ are hydrogen, and each $R^{1'}$ is, independently, optionally substituted $C_1$-$C_{20}$ aliphatic.

In certain embodiments of metal complexes IVa and IVb, at least one of the phenyl rings comprising the salicylaldehyde-derived portion of the metal complex is independently selected from the group consisting of:

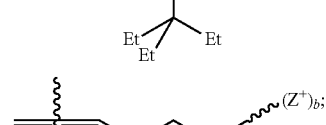

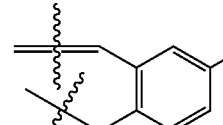

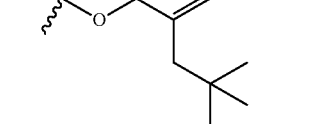

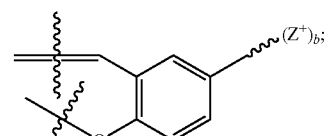

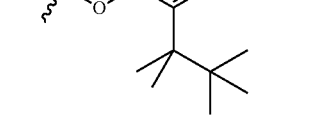

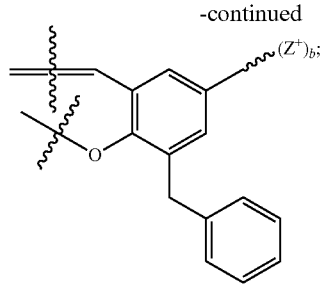

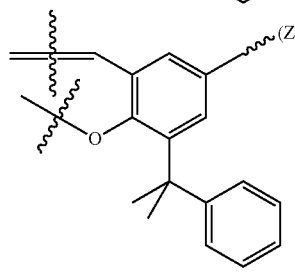

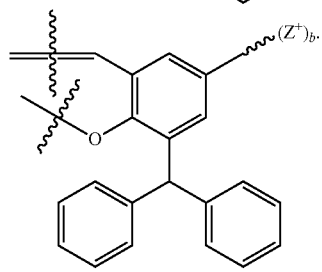

In still other embodiments, there is a cationic functional moiety tethered to the position para to the imine substituent of one or both of the salicylaldehyde-derived phenyl rings of the salen ligand as in formulae Va or Vb:

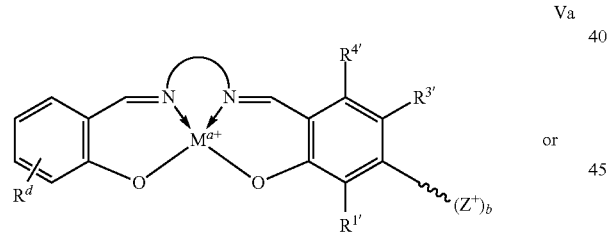

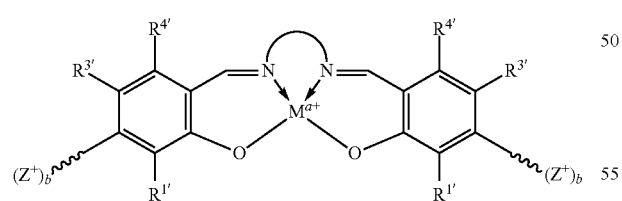

where M, a, $R^d$, $R^{1'}$, $R^{3'}$, $R^{4'}$, ⌒, and ⸺$(Z^+)_b$ are as defined above and in the classes and subclasses herein.

In certain embodiments of metal complexes having formulae Va or Vb, each $R^{4'}$ is hydrogen, and each $R^{1'}$ and $R^{3'}$ is, independently, hydrogen or optionally substituted $C_1$-$C_{20}$ aliphatic.

In certain embodiments of metal complexes Va and Vb, at least one of the phenyl rings comprising the salicylaldehyde-derived portion of the metal complex is independently selected from the group consisting of:

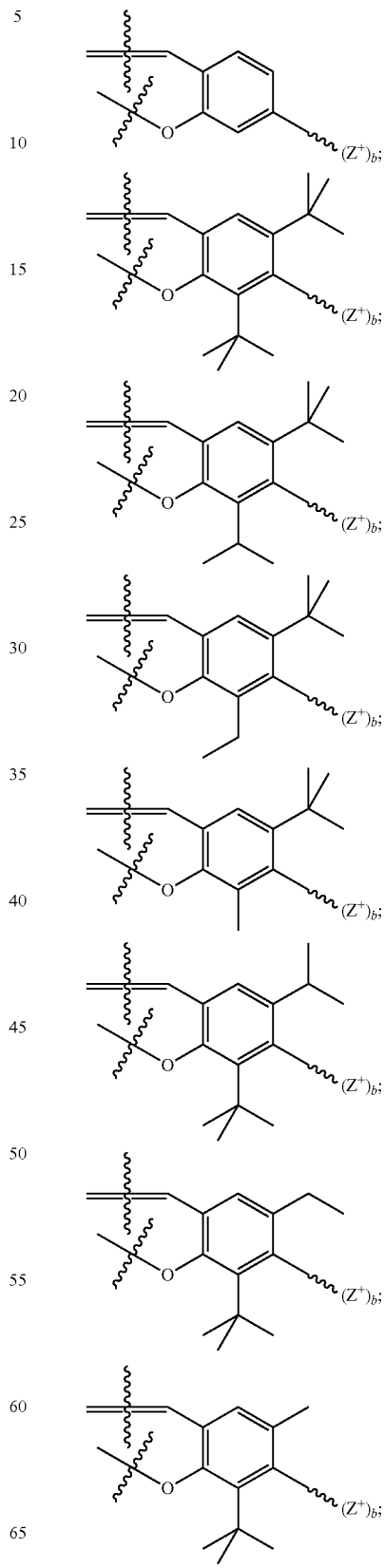

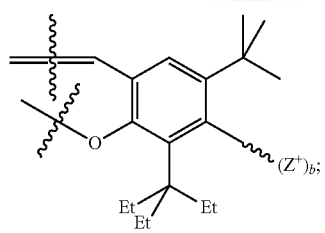
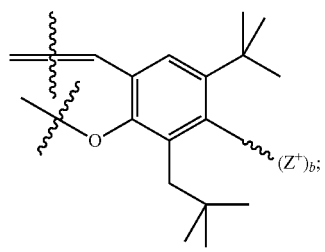
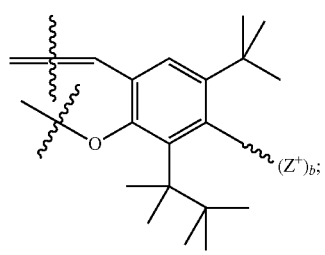
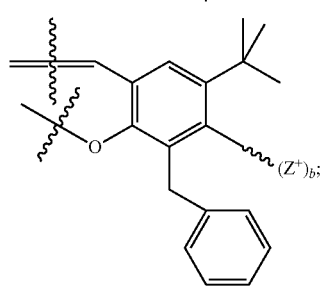
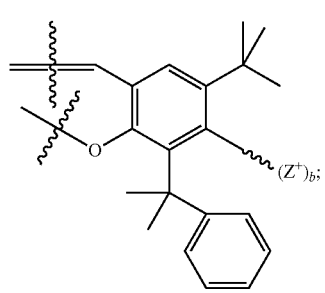
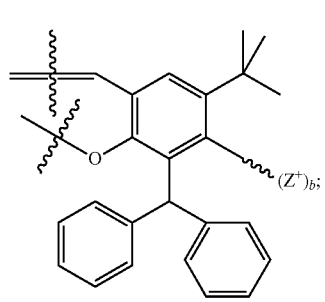
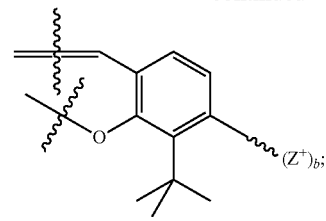
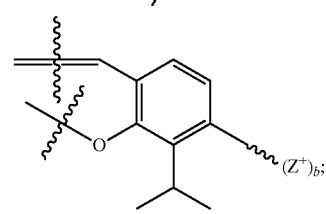
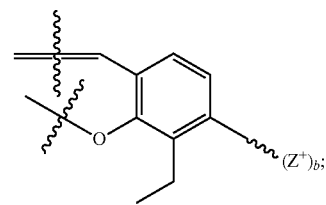
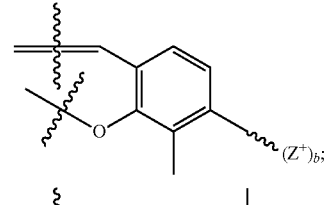
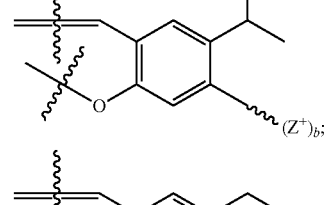
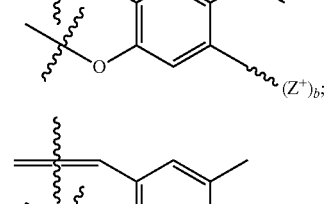
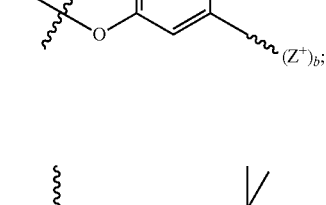
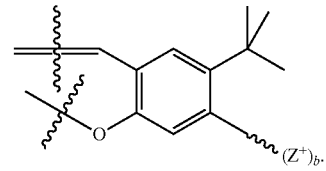
In still other embodiments, there is a cationic functional moiety tethered to the position para to the imine substituent of one or both of the salicylaldehyde-derived phenyl rings of the salen ligand as in formulae VIa and VIb:

VIa

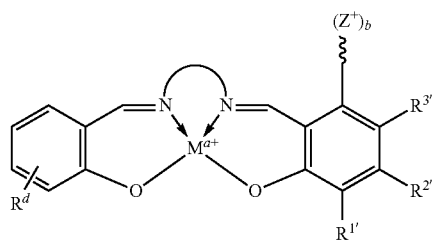

VIb

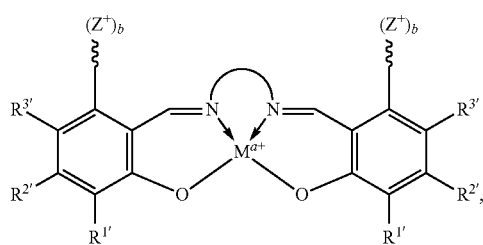

where M, a, $R^d$, $R^{1'}$, $R^{2'}$, $R^{3'}$, ⌒, and ―〜〜(Z⁺)ᵦ are as defined above and in the classes and subclasses herein.

In certain embodiments of metal complexes having formulae VIa or VIb, each $R^{2'}$ is hydrogen, and each $R^{1'}$ and $R^{3'}$ is, independently, hydrogen or optionally substituted $C_1$-$C_{20}$ aliphatic.

In certain embodiments of metal complexes VIa and VIb, at least one of the phenyl rings comprising the salicylaldehyde-derived portion of the metal complex is independently selected from the group consisting of:

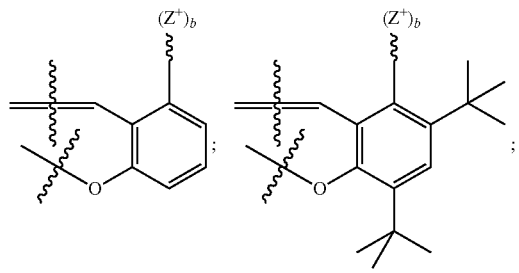

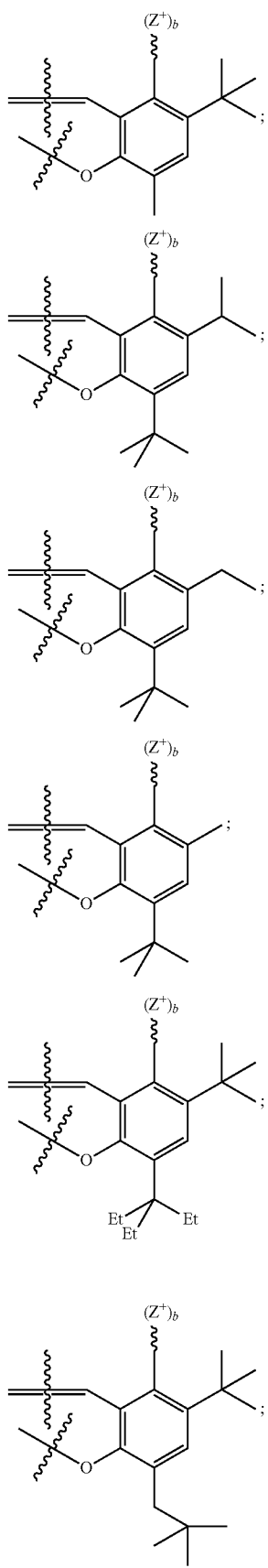

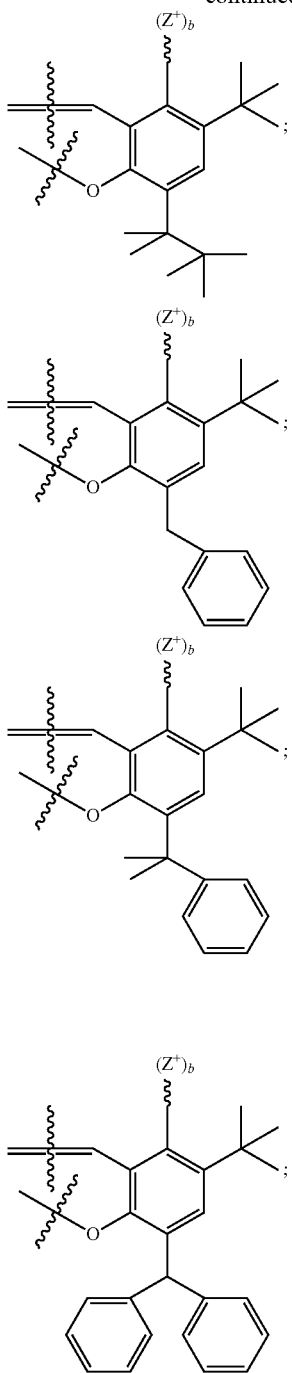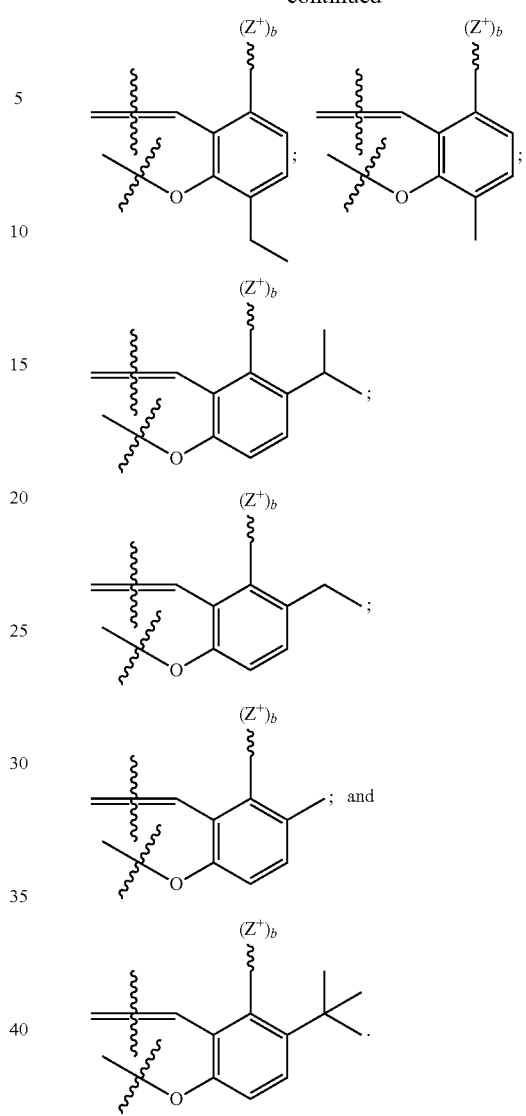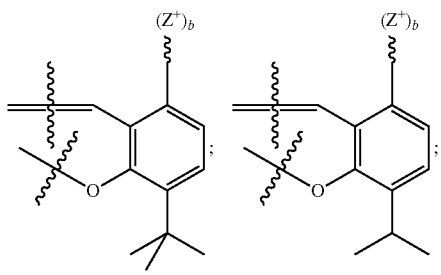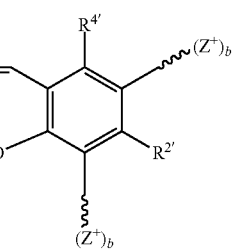
In still other embodiments, there are cationic functional moieties tethered to the positions ortho and para to the phenolic oxygen of one or both of the salicylaldehyde-derived phenyl rings of the salen ligand as in formulae VIIa and VIIb:

-continued

VIIb

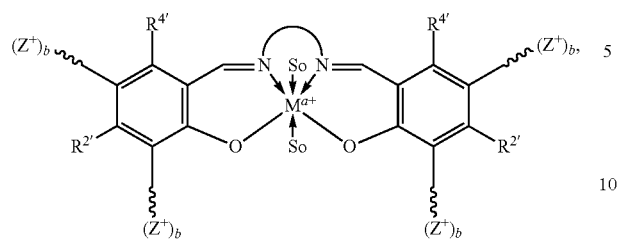

where each of M, a, $R^d$, $R^{2'}$, $R^{4'}$, ⌒, and ―∼∼$(Z^+)_b$, is as defined above and in the classes and subclasses herein.

In certain embodiments of compounds having formulae VIIa or VIIb, each $R^{2'}$ and $R^{4'}$ is, independently, hydrogen or optionally substituted $C_1$-$C_{20}$ aliphatic.

In certain embodiments of compounds having formulae VIIa or VIIb, each $R^{2'}$ and $R^{4'}$ is hydrogen.

In still other embodiments, there are cationic functional moieties tethered to the positions ortho and para to the imine substituent of one or both of the salicylaldehyde-derived phenyl rings of the salen ligand as in formulae VIIIa and VIIIb:

VIIIa

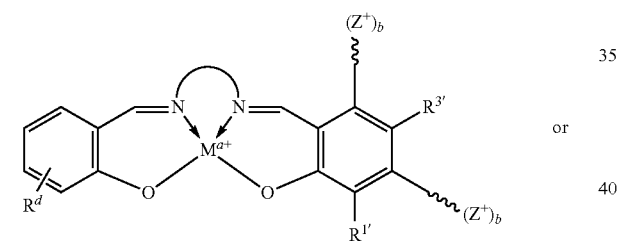

or

VIIIb

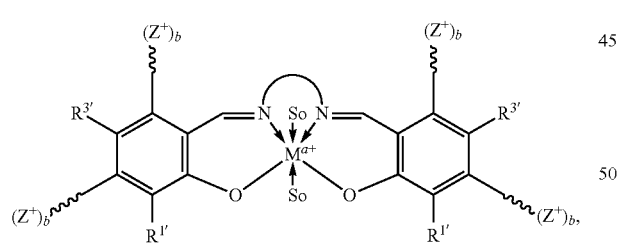

where each of M, a, $R^d$, $R^{1'}$, $R^{3'}$, ⌒, and ―∼∼$(Z^+)_b$ is as defined above and in the classes and subclasses herein.

In certain embodiments of metal complexes having formulae VIIIa or VIIIb, each $R^{1'}$ and $R^{3'}$ is, independently, optionally, hydrogen or substituted $C_1$-$C_{20}$ aliphatic.

In certain embodiments of the present invention, metal complexes of structures VIIIa or VIIIb above, at least one of the phenyl rings comprising the salicylaldehyde-derived portion of the catalyst is independently selected from the group consisting of:

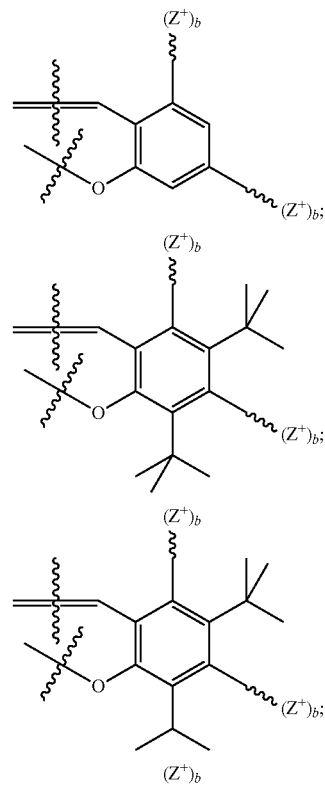

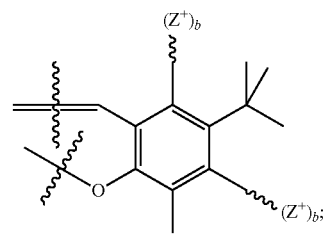

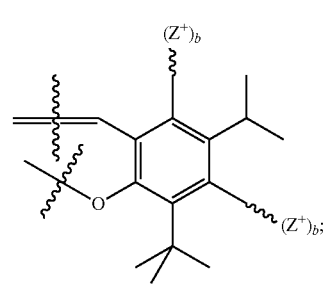

-continued
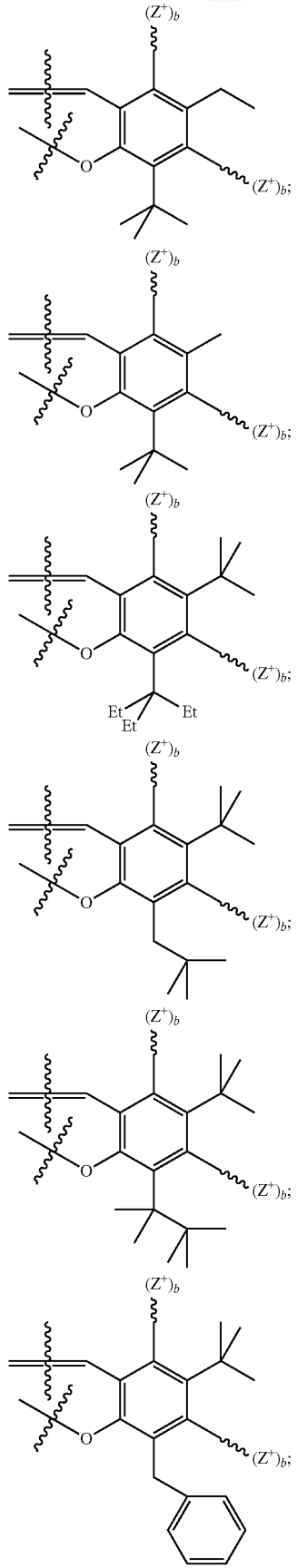
-continued
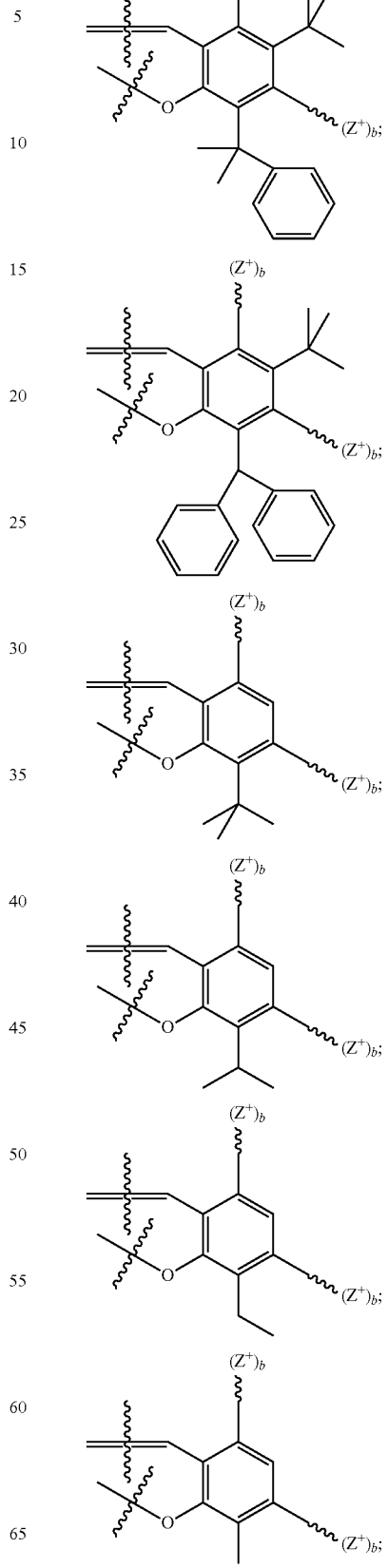

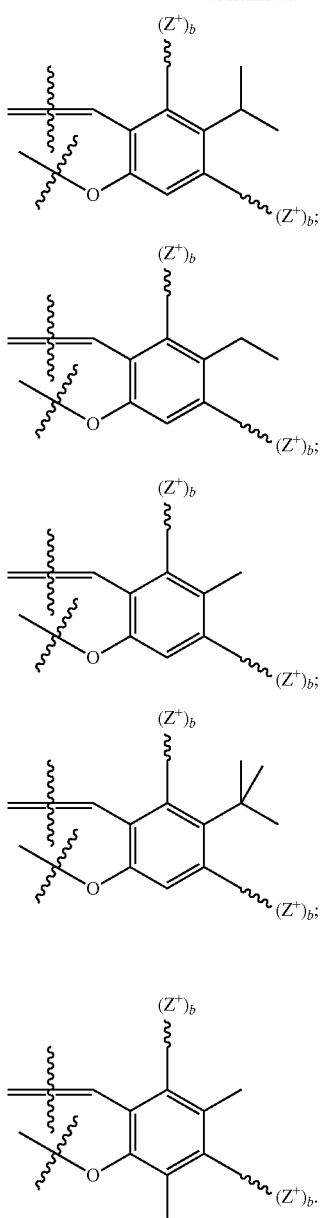

In yet other embodiments, there is a cationic functional moiety tethered to the imine carbon of the salen ligand as in formulae IXa and IXb:

IXa

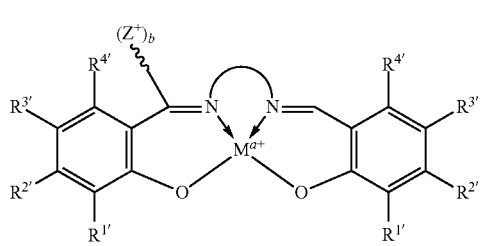

or

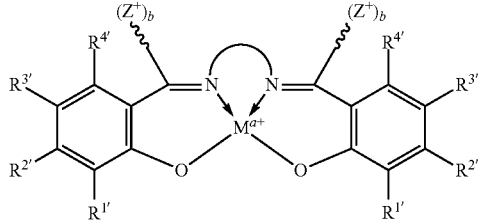

IXb where M, a, R, $R^1$, $R^2$, $R^3$, $R^4$, ⌢, and $\sim\!\!\sim\!\!(Z^+)_b$ are as defined above with the proviso that the atom of the cationic functional moiety attached to the salen ligand is a carbon atom.

In certain embodiments of compounds having formulae IXa or IXb, each $R^2$ and $R^4$ is hydrogen, and each $R^1$ and $R^3$ is, independently, hydrogen or optionally substituted $C_1$-$C_{20}$ aliphatic.

In certain embodiments of the present invention, catalysts of structures IXa or IXb above, at least one of the phenyl rings comprising the salicylaldehyde-derived portion of the metal complex is independently selected from the group consisting of:

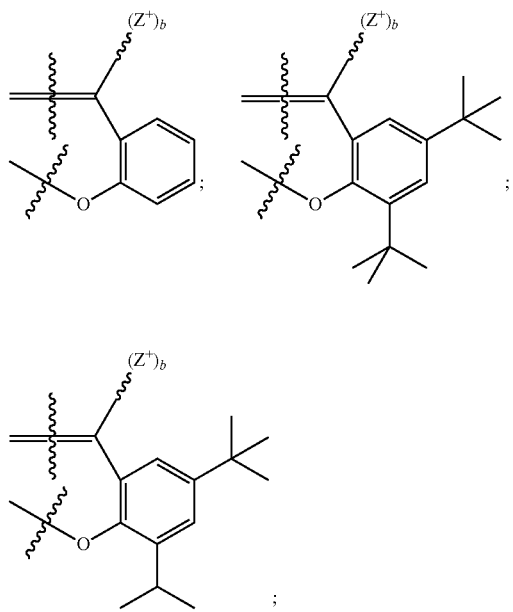

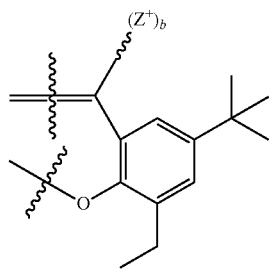

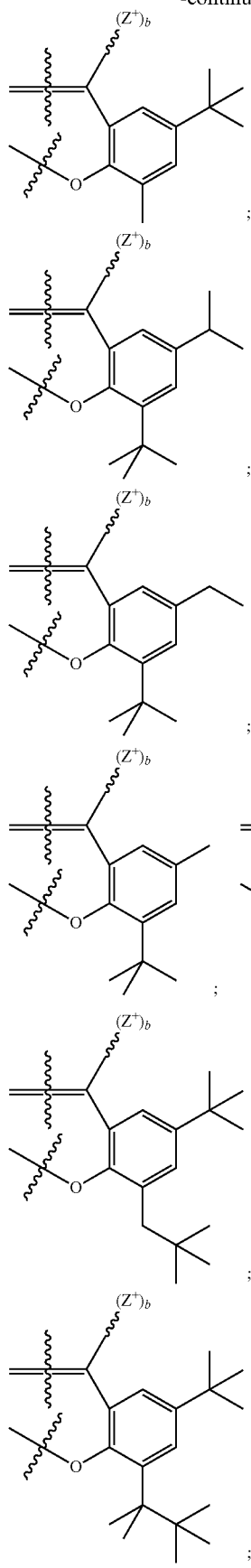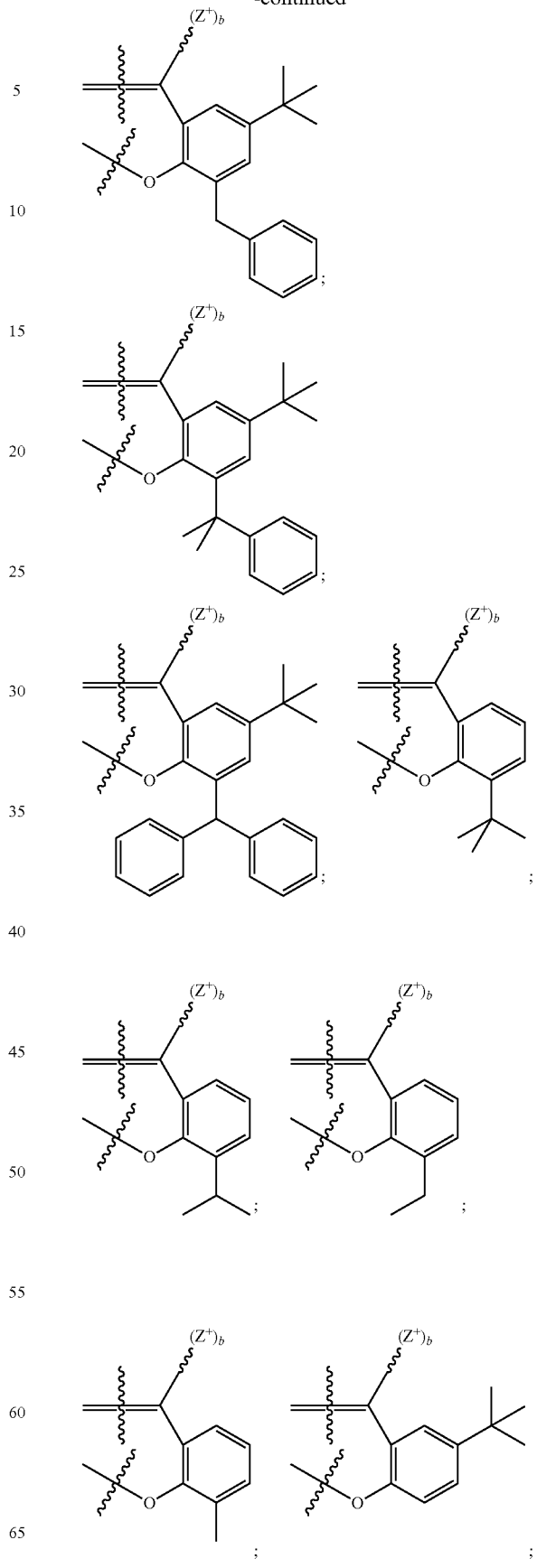

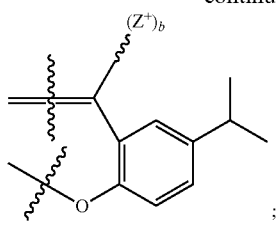

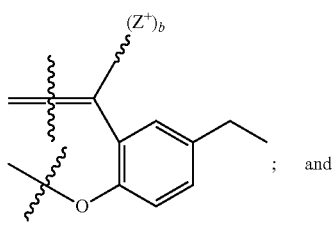

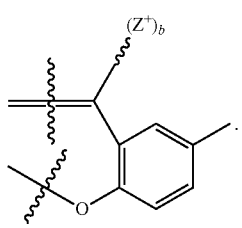

As shown above, the two phenyl rings derived from salicylaldehyde in the core salen structures need not be the same. Though not explicitly shown in formulae Ia through IXb above, it is to be understood that a metal complex may have a cationic functional moiety attached to different positions on each of the two rings, and such metal complexes are specifically encompassed within the scope of the present invention. Furthermore, cationic functional moieties can be present on multiple parts of the ligand, for instance cationic functional moieties can be present on the diamine bridge and on one or both phenyl rings in the same metal complex.

In certain embodiments, the salen ligand cores of metal complexes Ia through IXb above are selected from the group shown below wherein any available position may be independently substituted with one or more R-groups or one or more cationic functional moieties as described above.

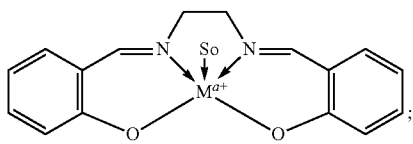

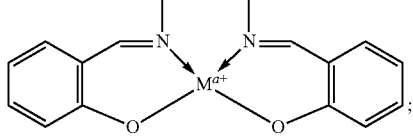

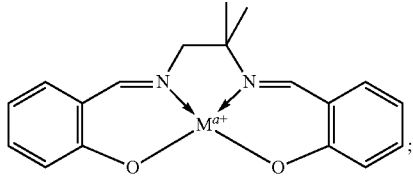

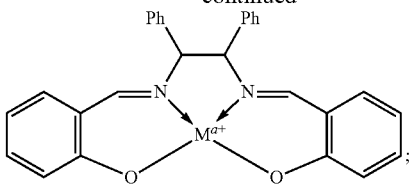

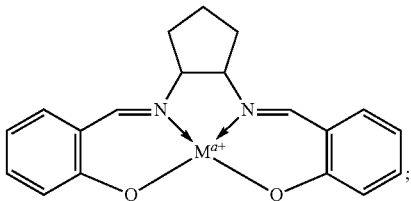

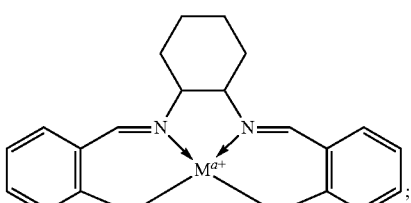

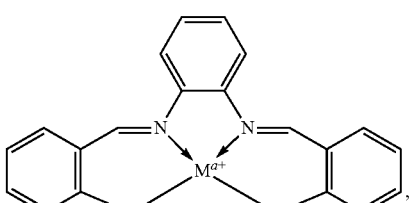

where M, a, R, ⌒, and ⸺(Z⁺)ᵦ are as defined above and in the classes and subclasses herein.

In another embodiment, at least one cationic functional moiety is tethered to the diamine-derived portion of the salen ligand, as shown in formula X:

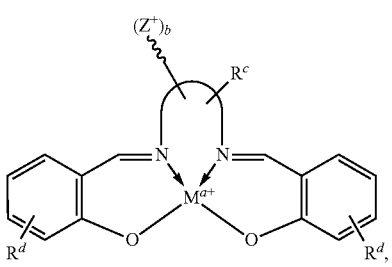

X where M, a, $R^d$, $R^c$, ⌒, and ⸺(Z⁺)ᵦ are as defined above and in the classes and subclasses herein.

In certain embodiments, salen ligands of formula X are selected from an optionally substituted moiety consisting of:

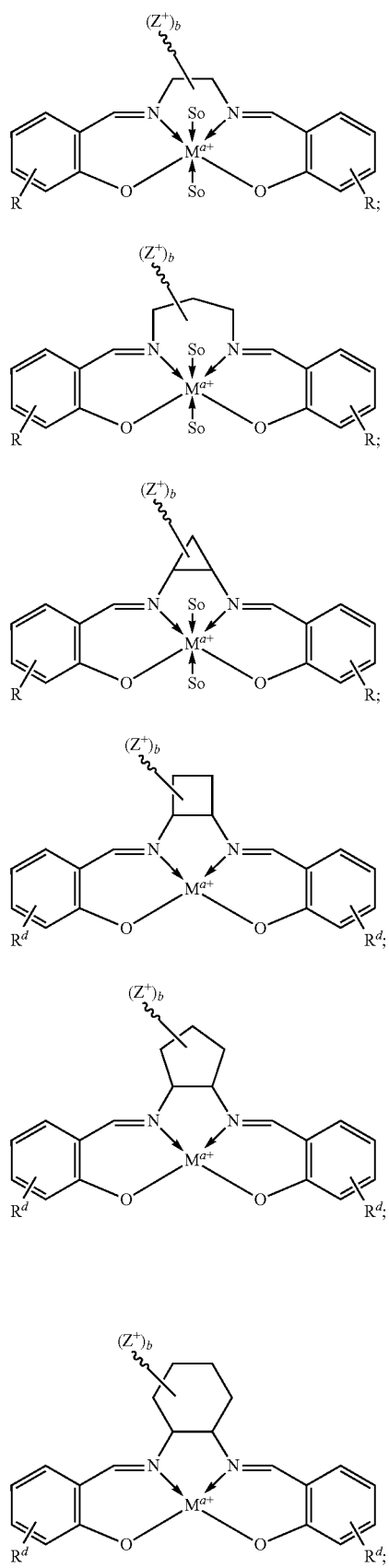
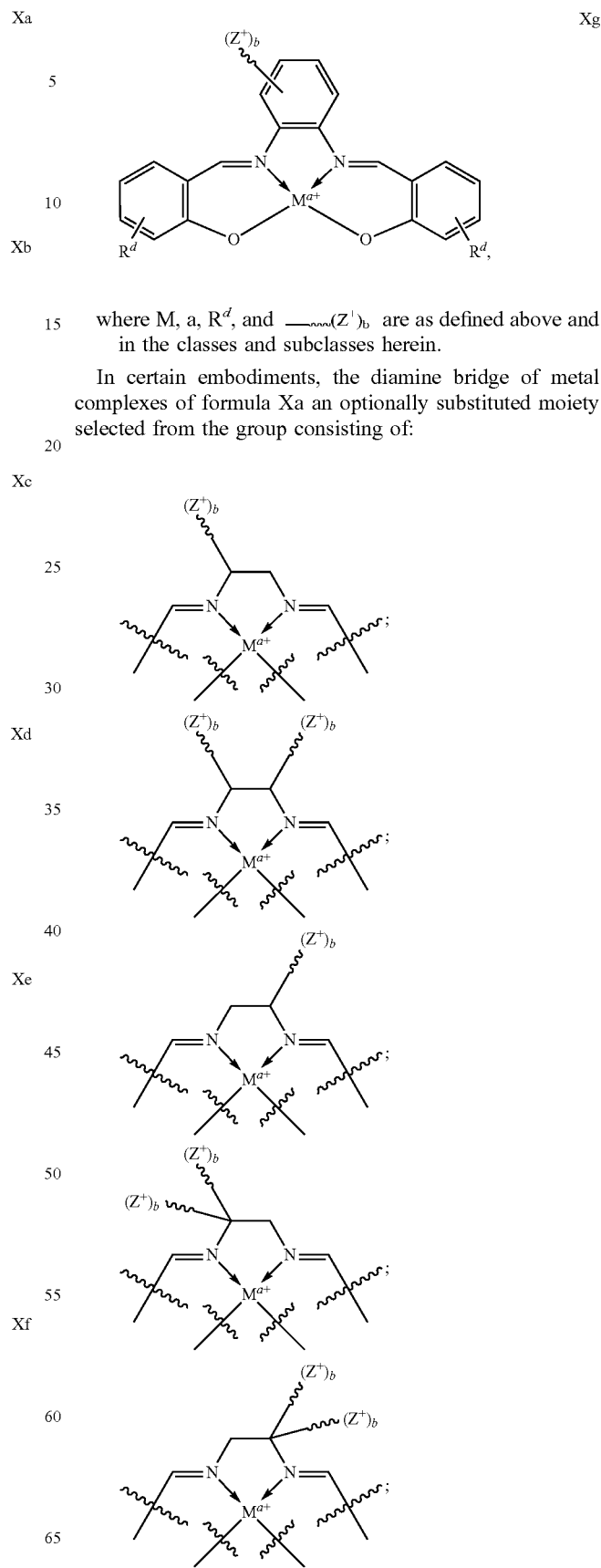
where M, a, $R^d$, and ⸺⁓⁓($Z'$)$_b$ are as defined above and in the classes and subclasses herein.
In certain embodiments, the diamine bridge of metal complexes of formula Xa an optionally substituted moiety selected from the group consisting of:

-continued

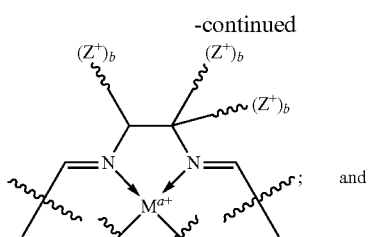

and

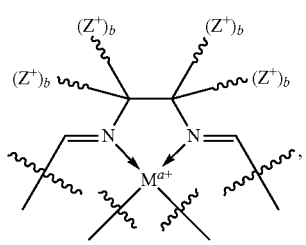

where each of M, a, and ⌇⌇(Z⁺)_b is as defined above and described in the classes and subclasses herein.

In certain embodiments, catalysts of the present invention comprise metal-tmtaa complexes. In certain embodiments, the moiety ⊕ has the structure:

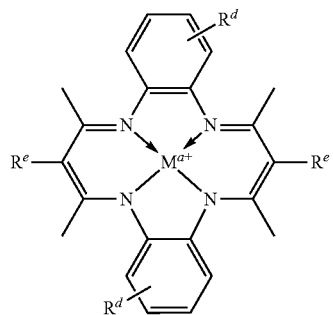

where M, a and $R^d$ are as defined above and in the classes and subclasses herein, and $R^e$ at each occurrence is independently a cationic functional moiety ⌇⌇(Z⁺)_b, hydrogen, halogen, —OR, —NR₂, —SR, —CN, —NO₂, —SO₂R, —SOR, —SO₂NR₂; —CNO, —NRSO₂R, —NCO, —N₃, —SiR₃; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, or sulfur; and 4- to 7-membered heterocyclic having 1-2 heteroatoms independently selected from the group consisting of nitrogen, oxygen, and sulfur.

In certain embodiments, the moiety ⊕ has the structure:

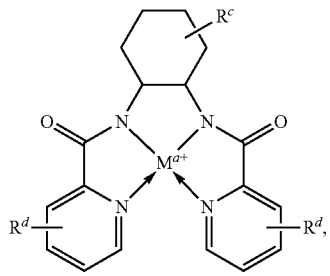

where each of M, a, $R^c$ and $R^d$ is as defined above and in the classes and subclasses herein.

In certain embodiments, at least one activating moiety is tethered to a diamine bridge of a ligand, as shown in formula III-a, III-b, and III-c:

(III-a)

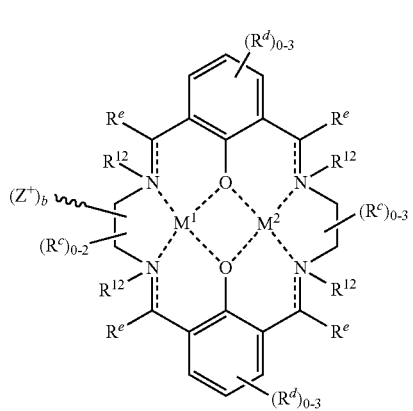

(III-b)

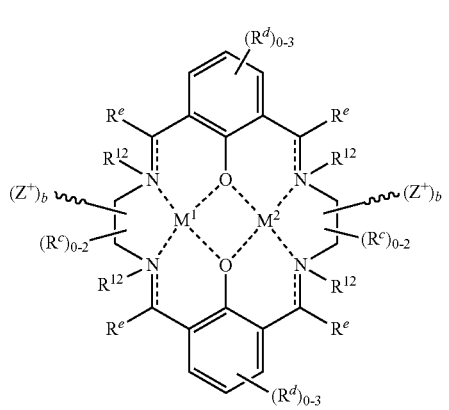

(III-c)

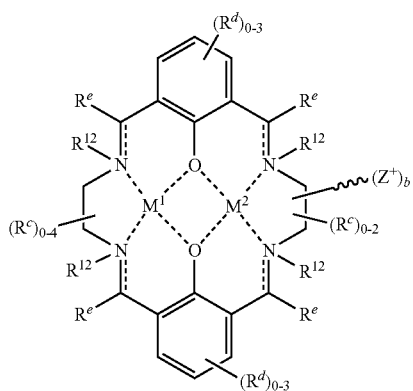

wherein each of $R^c$, $R^d$, $R^e$, Z, b, $M^1$, and $M^2$, is independently as defined above the described in classes and subclasses herein, and $R^{12}$ is optionally present, and if present is selected from the group consisting of: a ⁓$(Z^+)_b$ group; or an optionally substituted radical selected from the group consisting of $C_{1-20}$ aliphatic; $C_{1-20}$ heteroaliphatic; and phenyl.

In certain embodiments, at least one activating moiety is tethered to a diamine bridge of a ligand, as shown in formula IV-a, IV-b, and IV-c:

(IV-a)

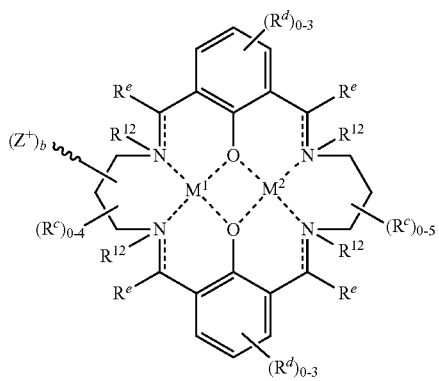

(IV-b)

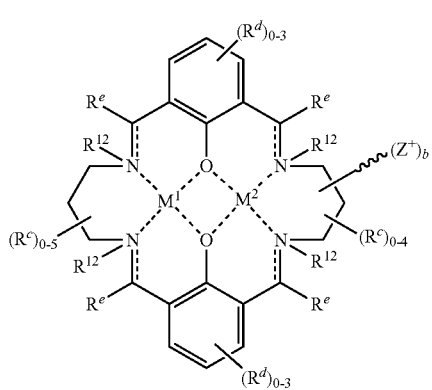

(IV-c)

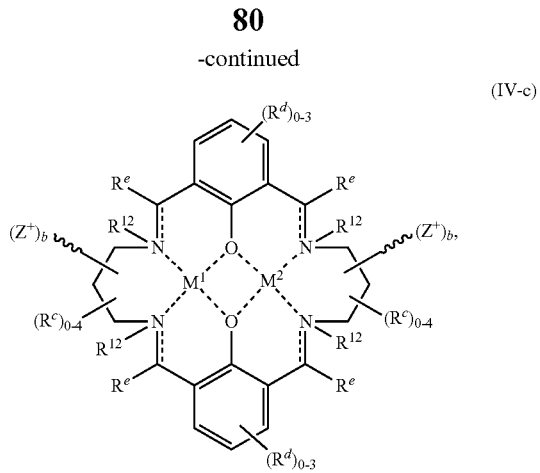

wherein each of $R^c$, $R^d$, $R^e$, Z, b, $M^1$, $M^2$, and $R^{12}$ is independently as defined above the described in classes and subclasses herein.

In certain embodiments, at least one activating moiety is tethered to a cyclic diamine bridge of a ligand, as shown in formula V-a, V-b, and V-c:

(V-a)

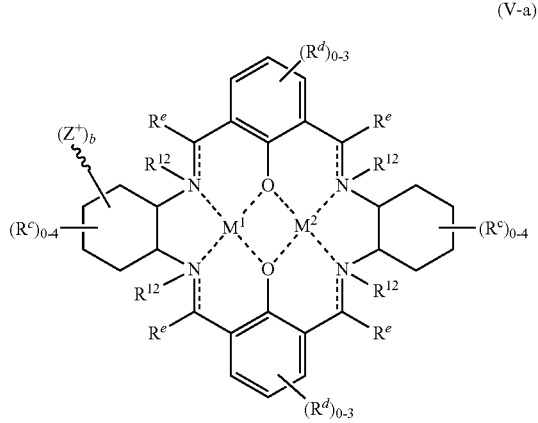

(V-b)

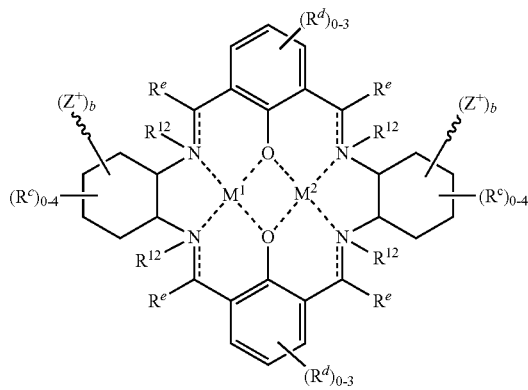

-continued (V-c)

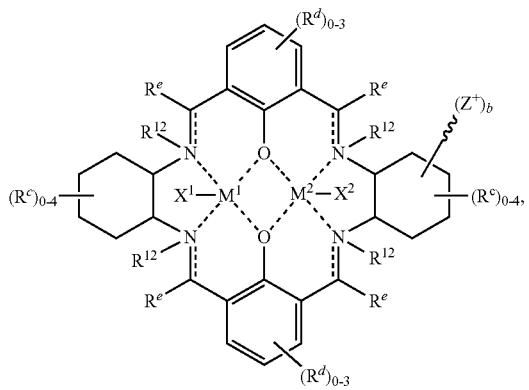

wherein each of $R^c$, $R^d$, $R^e$, Z, b, $M^1$, $M^2$, and $R^{12}$ is independently as defined above the described in classes and subclasses herein.

In certain embodiments, at least one activating moiety is tethered to a cyclic diamine bridge of a ligand, as shown in formula VI-a, VI-b, and VI-c:

(VI-a)

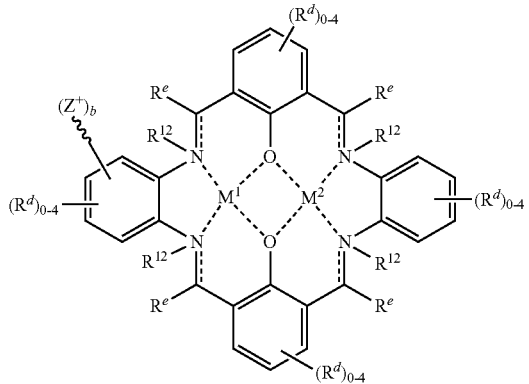

(VI-b)

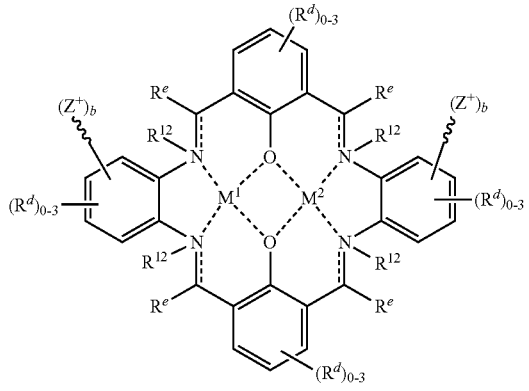

-continued (VI-c)

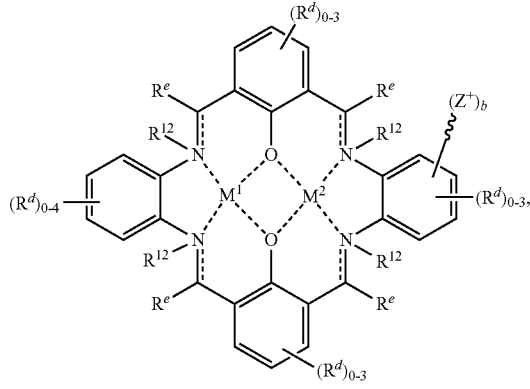

wherein each of $R^c$, $R^d$, $R^e$, Z, b, $M^1$, $M^2$, and $R^{12}$ is independently as defined above the described in classes and subclasses herein.

In certain embodiments, catalysts of the present invention comprise ligands capable of coordinating two metal atoms.

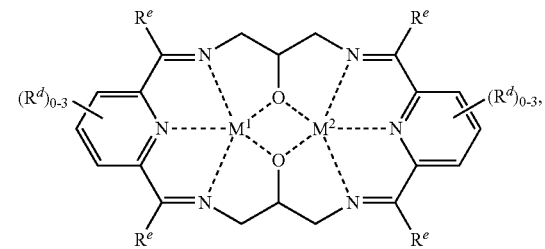

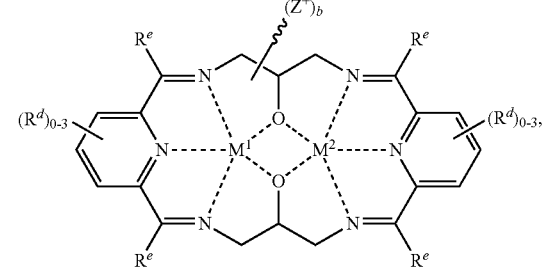

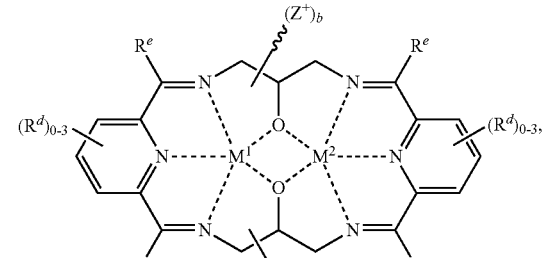

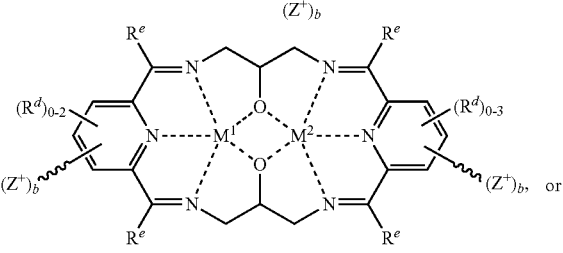

or

-continued

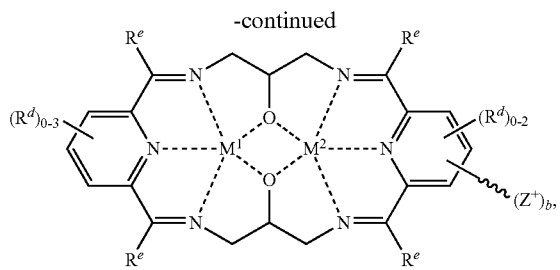

wherein each of $R^d$, $R^e$, $M^1$, $M^2$, and —ᴧᴧᴧ$(Z^+)_b$ is independently as defined above and described in classes and subclasses herein.

III. Metal Atoms

In certain embodiments, the metal atom M in any of the metal complexes described above and in the classes, subclasses and tables herein, is selected from the periodic table groups 2-13, inclusive. In certain embodiments, M is a transition metal selected from the periodic table groups 4, 6, 11, 12 and 13. In certain embodiments, M is aluminum, chromium, titanium, indium, gallium, zinc cobalt, or copper. In certain embodiments, M is aluminum. In other embodiments, M is chromium.

In certain embodiments, M has an oxidation state of +2. In certain embodiments, M is Zn(II), Cu(II), Mn(II), Co(II), Ru(II), Fe(II), Co(II), Rh(II), Ni(II), Pd(II) or Mg(II). In certain embodiments M is Zn(II). In certain embodiments M is Cu(II).

In certain embodiments, M has an oxidation state of +3. In certain embodiments, M is Al(III), Cr(III), Fe(III), Co(III), Ti(III) In(III), Ga(III) or Mn(III). In certain embodiments M is Al(III). In certain embodiments M is Cr(III).

In certain embodiments, M has an oxidation state of +4. In certain embodiments, M is Ti(IV) or Cr(IV).

In certain embodiments, $M^1$ and $M^2$ are each independently a metal atom selected from the periodic table groups 2-13, inclusive. In certain embodiments, M is a transition metal selected from the periodic table groups 4, 6, 11, 12 and 13. In certain embodiments, M is aluminum, chromium, titanium, indium, gallium, zinc cobalt, or copper. In certain embodiments, M is aluminum. In other embodiments, M is chromium. In certain embodiments, $M^1$ and $M^2$ are the same. In certain embodiments, $M^1$ and $M^2$ are the same metal, but have different oxidation states. In certain embodiments, $M^1$ and $M^2$ are different metals.

In certain embodiments, one or more of $M^1$ and $M^2$ has an oxidation state of +2. In certain embodiments, $M^1$ is Zn(II), Cu(II), Mn(II), Co(II), Ru(II), Fe(II), Co(II), Rh(II), Ni(II), Pd(II) or Mg(II). In certain embodiments $M^1$ is Zn(II). In certain embodiments $M^1$ is Cu(II). In certain embodiments, $M^2$ is Zn(II), Cu(II), Mn(II), Co(II), Ru(II), Fe(II), Co(II), Rh(II), Ni(II), Pd(II) or Mg(II). In certain embodiments $M^2$ is Zn(II). In certain embodiments $M^2$ is Cu(II).

In certain embodiments, one or more of $M^1$ and $M^2$ has an oxidation state of +3. In certain embodiments, $M^1$ is Al(III), Cr(III), Fe(III), Co(III), Ti(III) In(III), Ga(III) or Mn(III). In certain embodiments $M^1$ is Al(III). In certain embodiments $M^1$ is Cr(III). In certain embodiments, $M^2$ is Al(III), Cr(III), Fe(III), Co(III), Ti(III) In(III), Ga(III) or Mn(III). In certain embodiments $M^2$ is Al(III). In certain embodiments $M^2$ is Cr(III).

In certain embodiments, one or more of $M^1$ and $M^2$ has an oxidation state of +4. In certain embodiments, $M^1$ is Ti(IV) or Cr(IV). In certain embodiments, $M^2$ is Ti(IV) or Cr(IV).

In certain embodiments, one or more neutral two electron donors coordinate to M $M^1$ or $M^2$ and fill the coordination valence of the metal atom. In certain embodiments, the neutral two electron donor is a solvent molecule. In certain embodiments, the neutral two electron donor is an ether. In certain embodiments, the neutral two electron donor is tetrahydrofuran, diethyl ether, acetonitrile, carbon disulfide, or pyridine. In certain embodiments, the neutral two electron donor is tetrahydrofuran. In certain embodiments, the neutral two electron donor is an epoxide. In certain embodiments, the neutral two electron donor is an ester or a lactone.

IV. Metal Carbonyl Anions

In certain embodiments, the anionic metal carbonyl compound has the general formula $[Q_dM'_e(CO)_w]^{y-}$, where Q is any ligand and need not be present, M' is a metal atom, d is an integer between 0 and 8 inclusive, e is an integer between 1 and 6 inclusive, w is a number such as to provide the stable anionic metal carbonyl complex, and x is the charge of the anionic metal carbonyl compound. In certain embodiments, the anionic metal carbonyl has the general formula $[QM'(CO)_w]^{y-}$, where Q is any ligand and need not be present, M' is a metal atom, w is a number such as to provide the stable anionic metal carbonyl, and y is the charge of the anionic metal carbonyl.

In certain embodiments, the anionic metal carbonyl compounds include monoanionic carbonyl complexes of metals from groups 5, 7 or 9 of the periodic table and dianionic carbonyl complexes of metals from groups 4 or 8 of the periodic table. In some embodiments, the anionic metal carbonyl compound contains cobalt or manganese. In some embodiments, the anionic metal carbonyl compound contains rhodium. Suitable anionic metal carbonyl compounds include, but are not limited to: $[Co(CO)_4]^-$, $[Ti(CO)_6]^{2-}$ $[V(CO)_6]^-$ $[Rh(CO)_4]^-$, $[Fe(CO)_4]^{2-}$ $[Ru(CO)_4]^{2-}$, $[Os(CO)_4]^{2-}$ $[Cr_2(CO)_{10}]^{2-}$ $[Fe_2(CO)_8]^{2-}$ $[Tc(CO)_5]^-$ $[Re(CO)_5]^-$ and $[Mn(CO)_5]^-$. In certain embodiments, the anionic metal carbonyl is $[Co(CO)_4]^-$. In some cases, a mixture of two or more anionic metal carbonyl complexes may be present in the catalyst.

The term "such as to provide a stable anionic metal carbonyl for $[Q_dM'_e(CO)_w]^{y-}$ is used herein to mean that $[Q_dM'_e(CO)_w]^{y-}$ is a species characterizable by analytical means, e.g., NMR, IR, X-ray crystrallography, Raman spectroscopy and/or electron spin resonance (EPR) and isolable in catalyst form as the anion for a metal complex cation or a species formed in situ.

In certain embodiments, one or two of the CO ligands of any of the metal carbonyl compounds described above is replaced with a ligand Q. In certain embodiments, the ligand Q is present and represents a phosphine ligand. In certain embodiments, Q is present and represents a cyclopentadienyl (cp) ligand.

V. Carbonylation Catalysts

In certain embodiments, catalysts of the present invention include the combination of:

iv) one or more cationic functional moieties, where each cationic functional moiety comprising comprising the combination of a linker as defined in Section Ia above and 1 to 4 cationic functional groups as defined in Section Ib above;

v) one or more ligands as defined in Section II to which at least one cationic functional moiety is covalently tethered and the ligand(s) is/are coordinated to one or two metal atoms as described in Section III to form a metal complex; and vi) at least one anionic metal carbonyl species associated with a cation present on the metal complex.

In certain embodiments, catalysts of the present invention include a complex chosen from Catalyst Table 1:
CATALYST TABLE 1
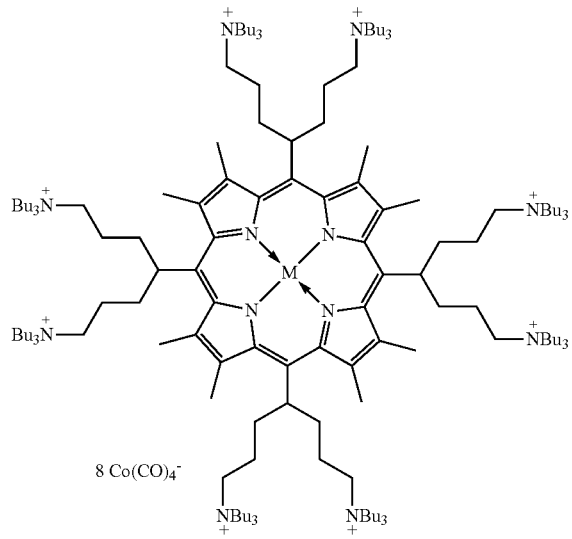
8 Co(CO)$_4^-$
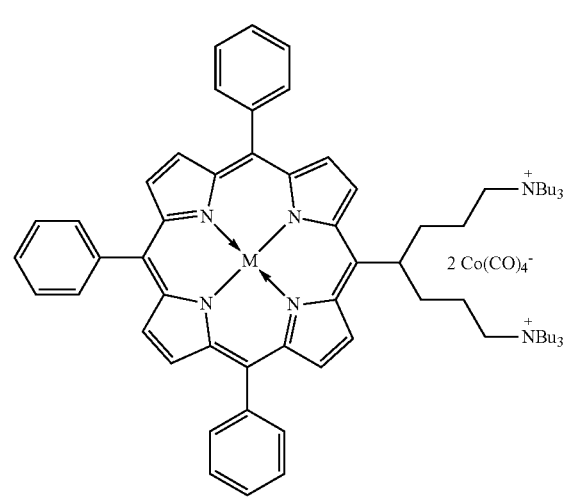
2 Co(CO)$_4^-$
CATALYST TABLE 1-continued
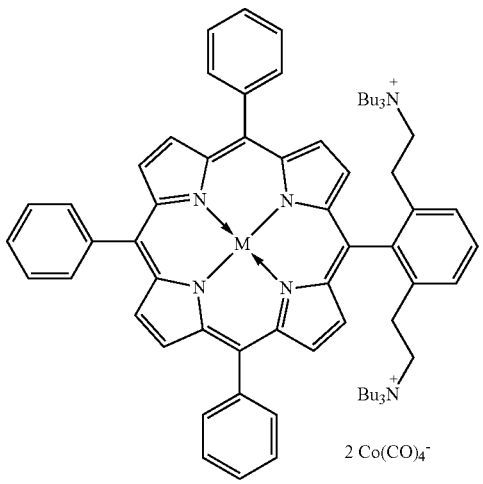
2 Co(CO)$_4^-$
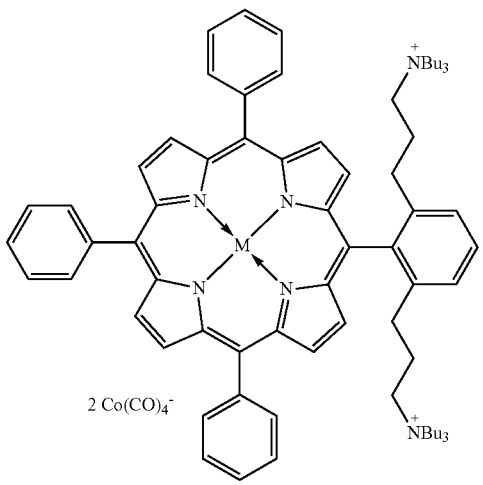
2 Co(CO)$_4^-$
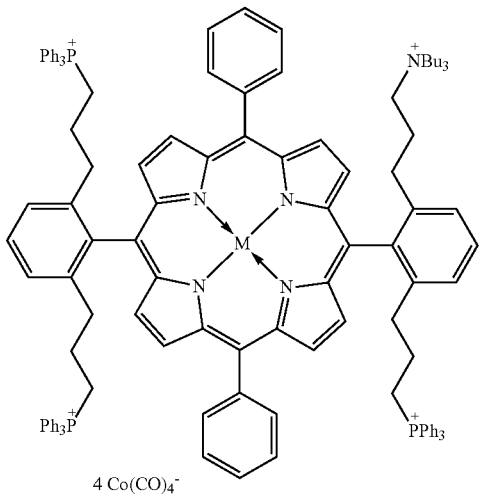
4 Co(CO)$_4^-$ CATALYST TABLE 1-continued
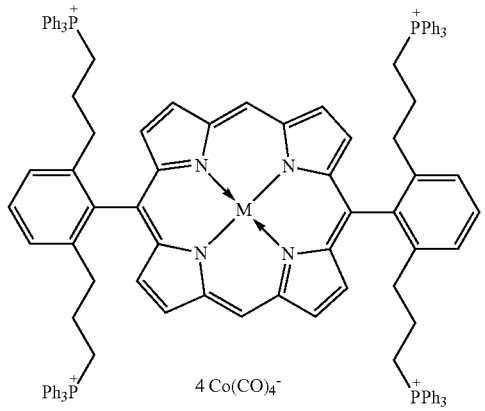
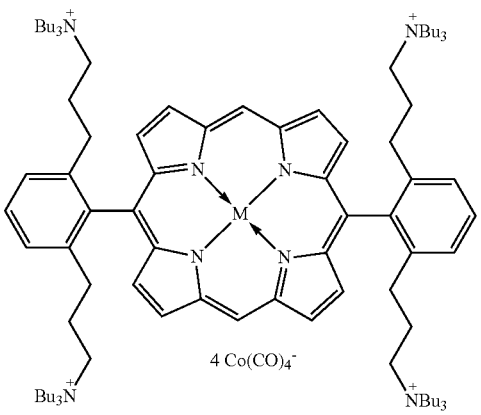
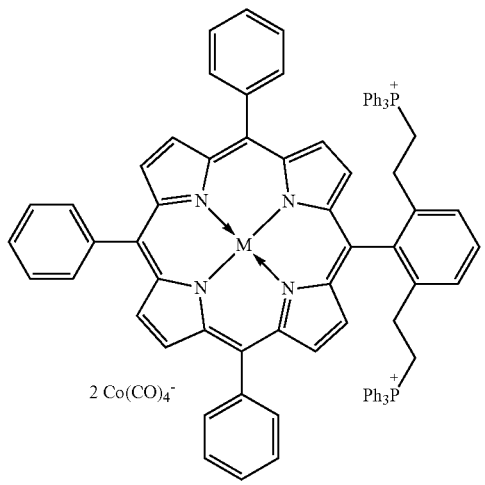
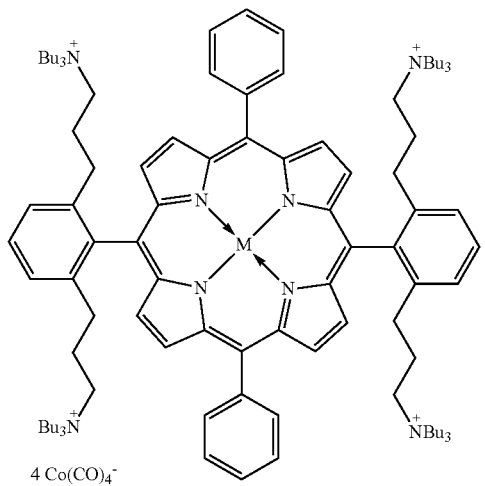
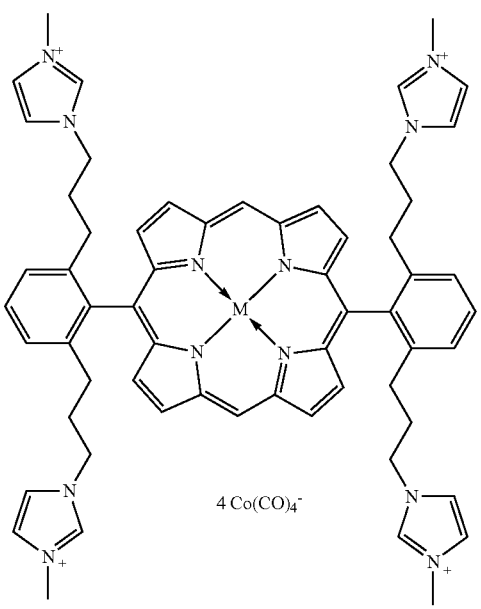

89
CATALYST TABLE 1-continued
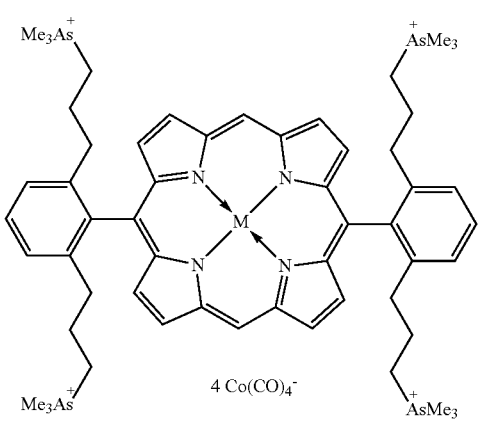
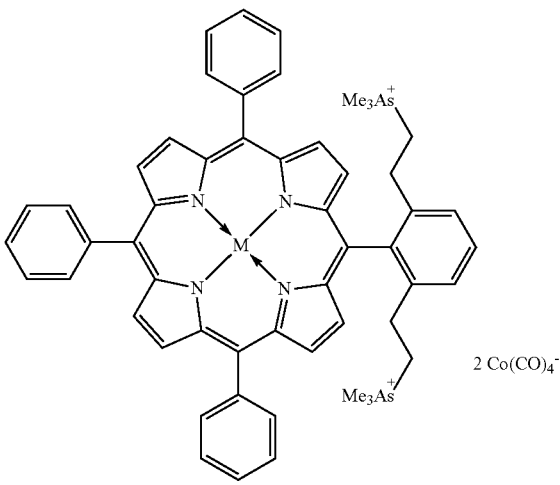
90
CATALYST TABLE 1-continued
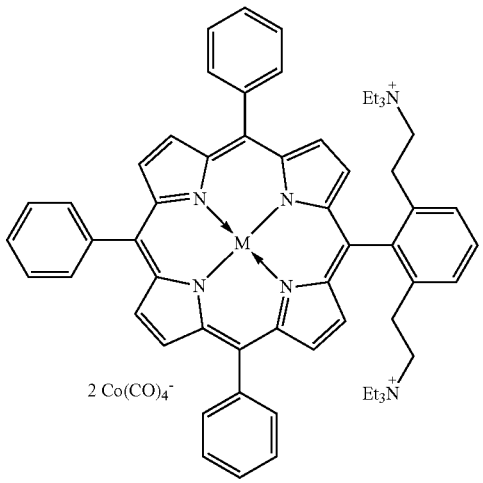
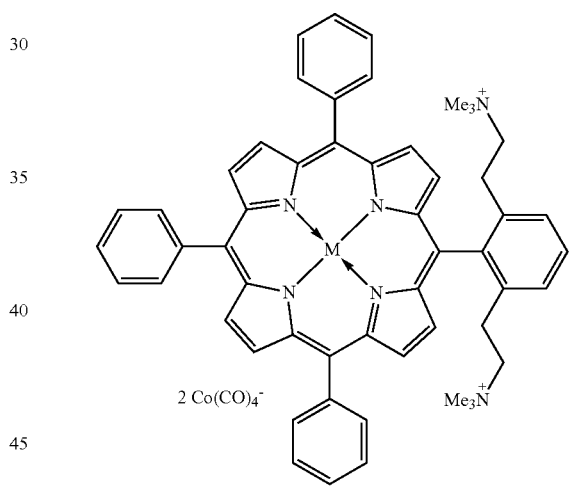
In certain embodiments, catalysts of the present invention include a complex chosen from Catalyst Table 2:
CATALYST TABLE 2
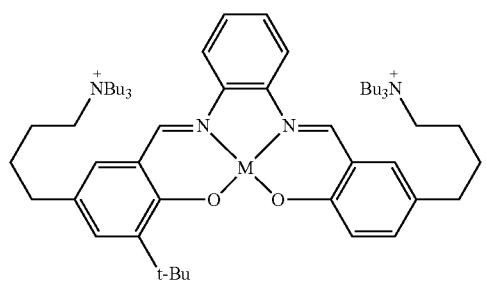

CATALYST TABLE 2-continued
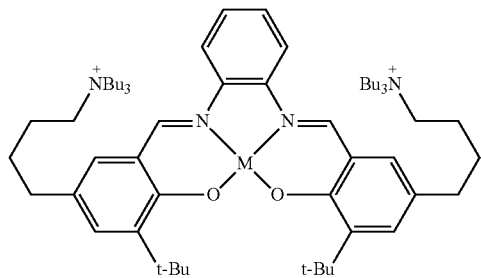
2 Co(CO)$_4^-$
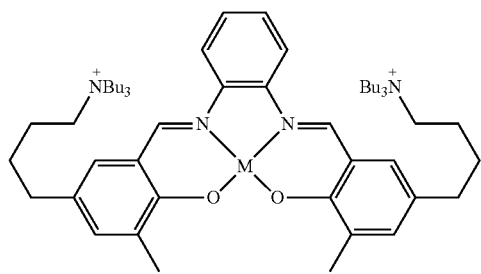
2 Co(CO)$_4^-$
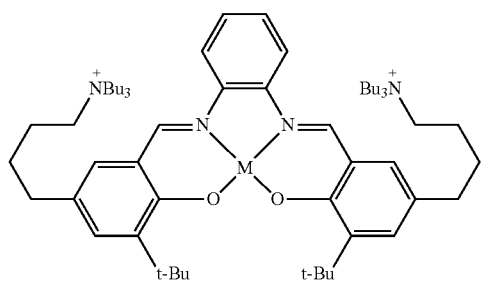
2 Co(CO)$_4^-$
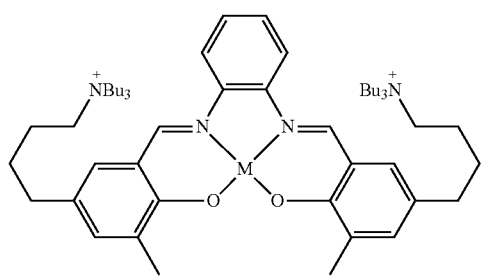
2 Co(CO)$_4^-$
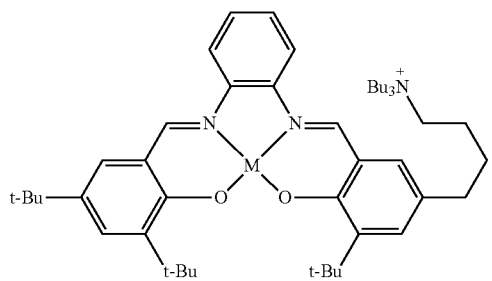
Co(CO)$_4^-$ CATALYST TABLE 2-continued
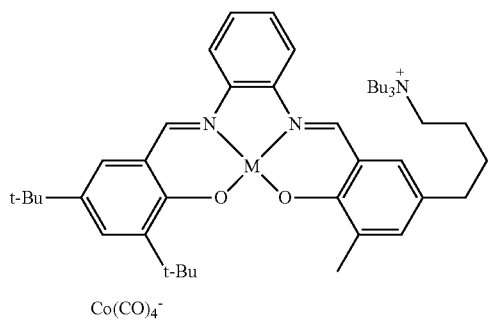
Co(CO)$_4^-$
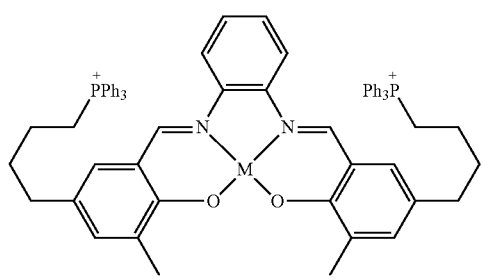
2 Co(CO)$_4^-$
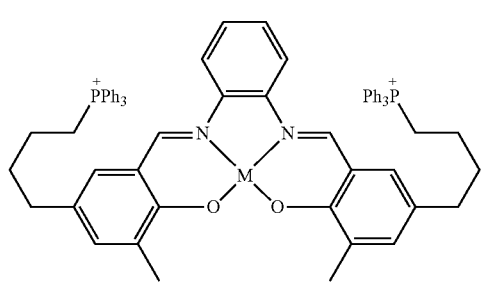
2 Co(CO)$_4^-$
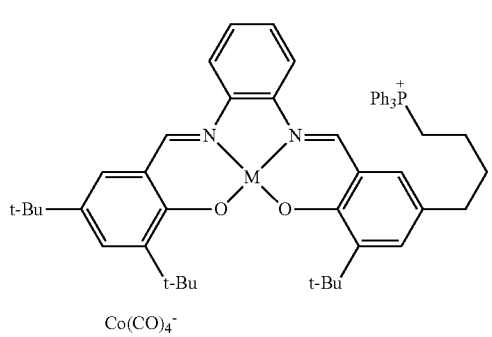
Co(CO)$_4^-$
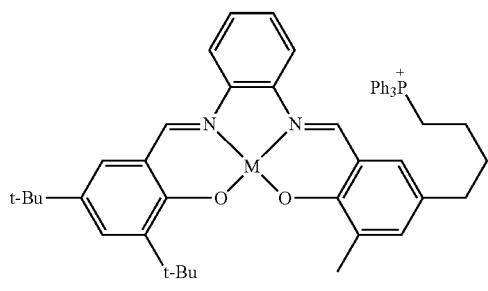
Co(CO)$_4^-$ CATALYST TABLE 2-continued
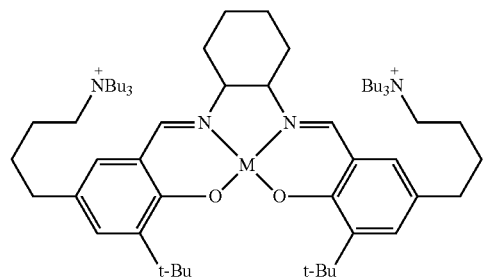
2 Co(CO)$_4^-$
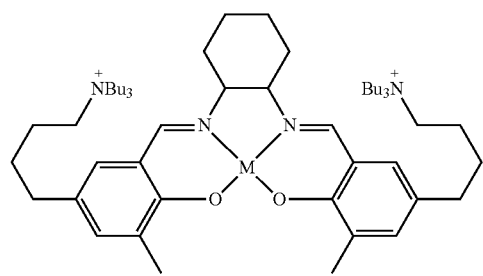
2 Co(CO)$_4^-$
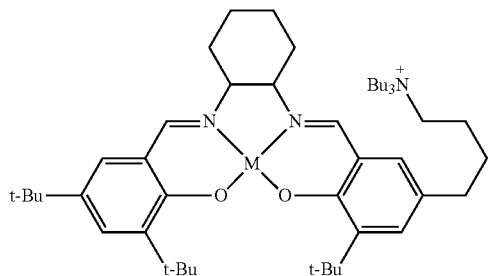
Co(CO)$_4^-$
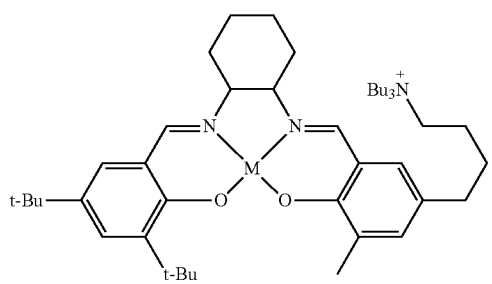
Co(CO)$_4^-$
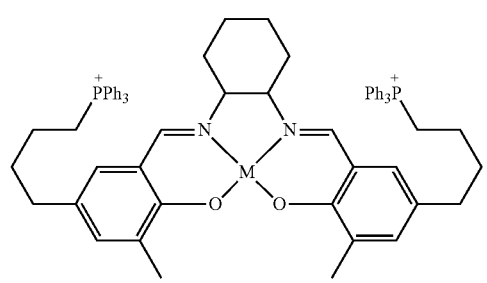
2 Co(CO)$_4^-$ CATALYST TABLE 2-continued
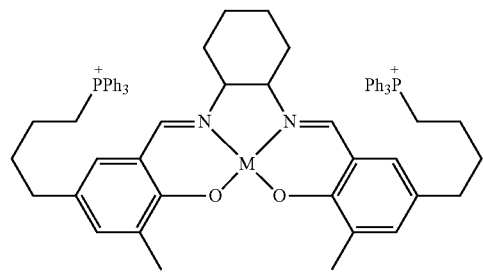
2 Co(CO)$_4^-$
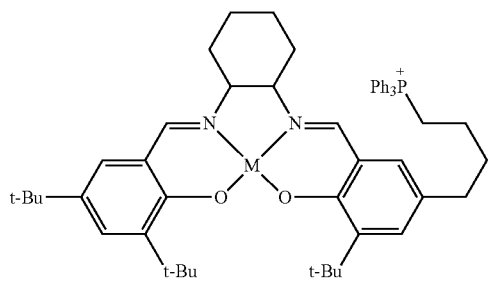
Co(CO)$_4^-$
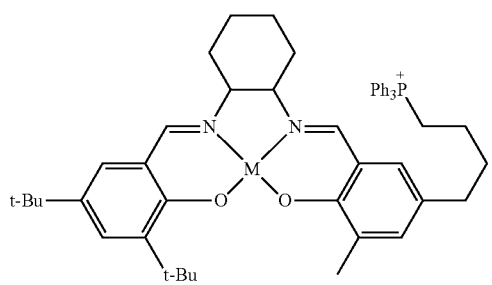
Co(CO)$_4^-$
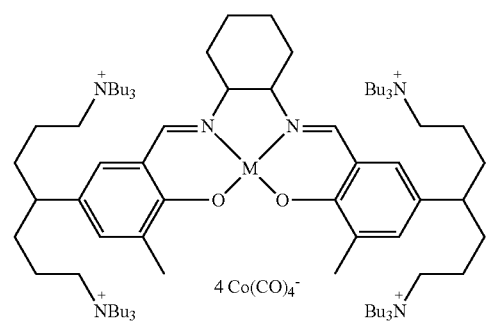
4 Co(CO)$_4^-$
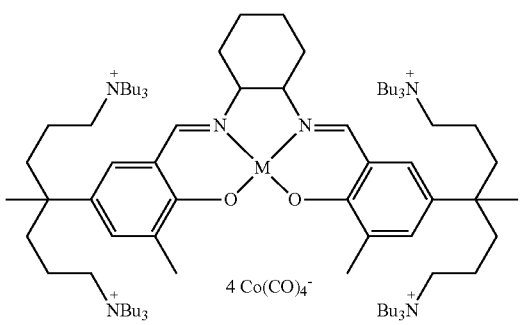
4 Co(CO)$_4^-$ CATALYST TABLE 2-continued
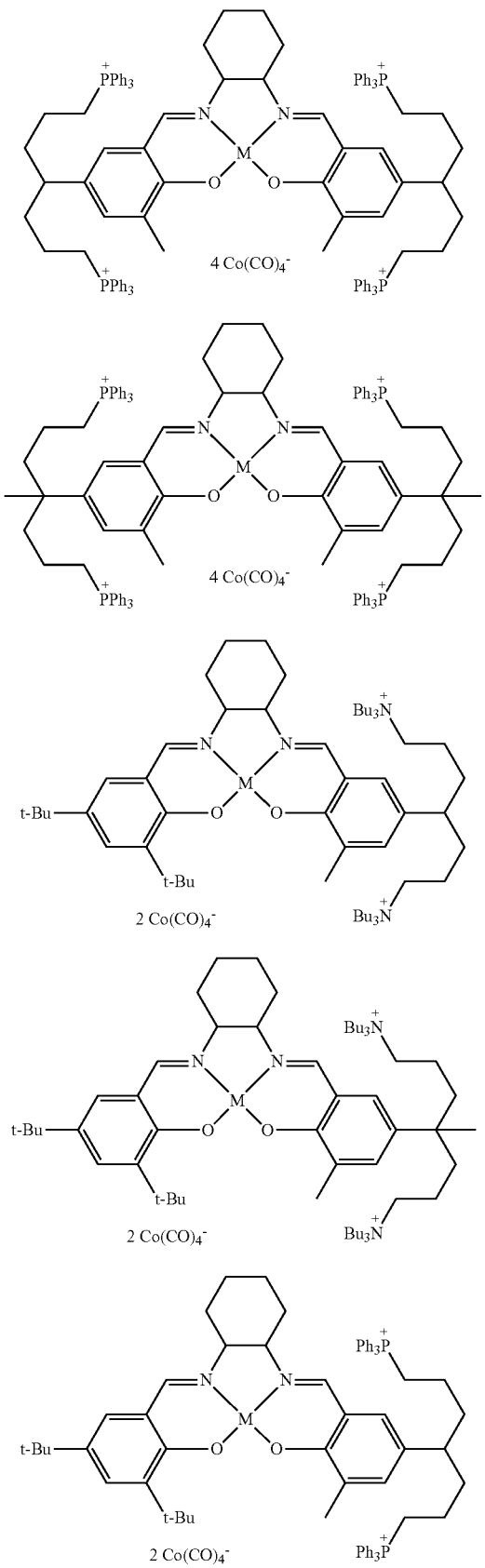

CATALYST TABLE 2-continued
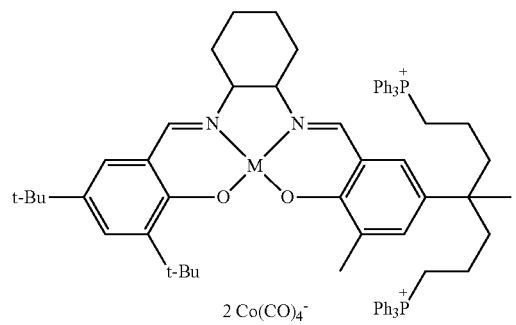
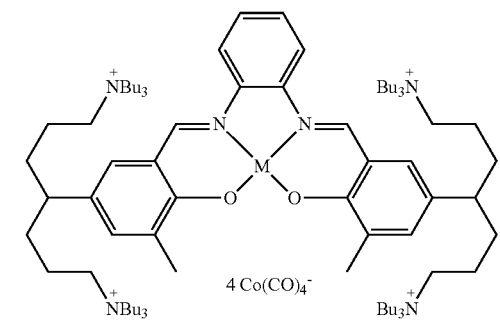
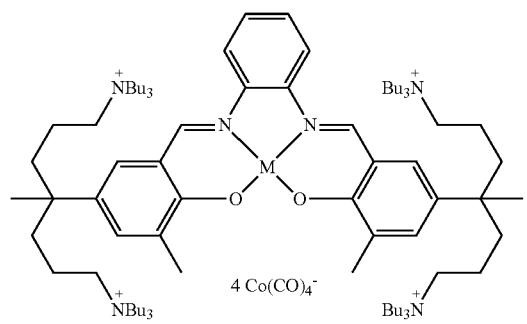
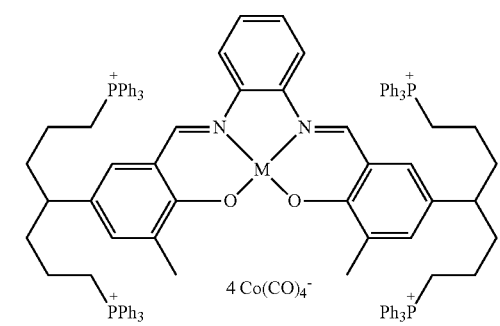
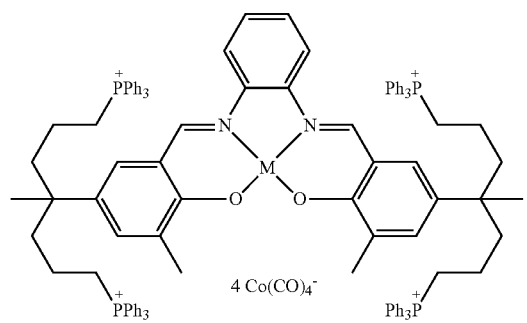

CATALYST TABLE 2-continued
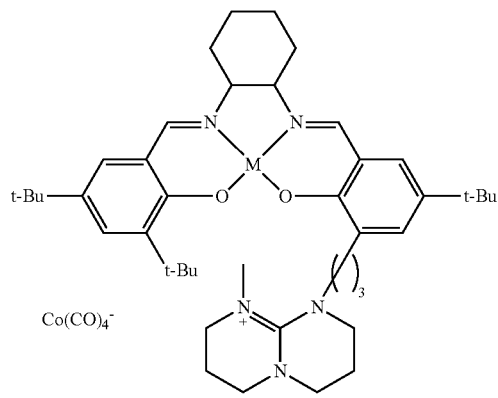
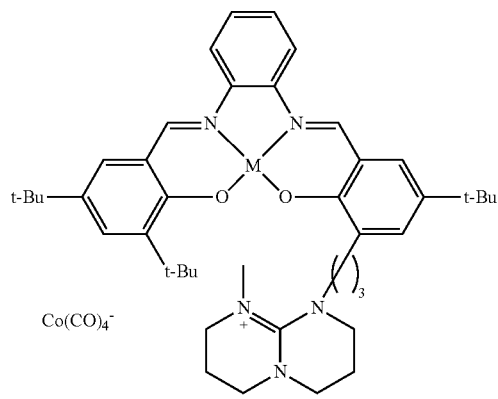
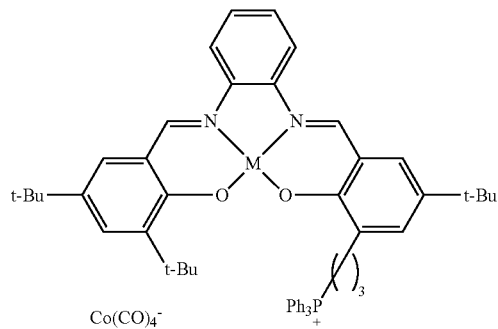
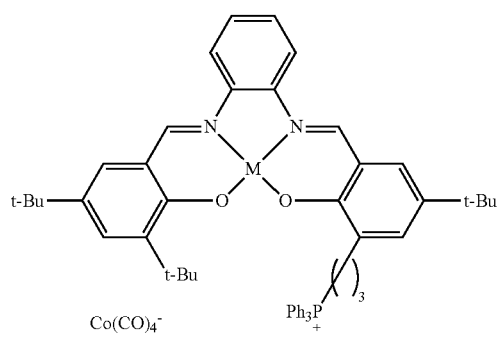

CATALYST TABLE 2-continued
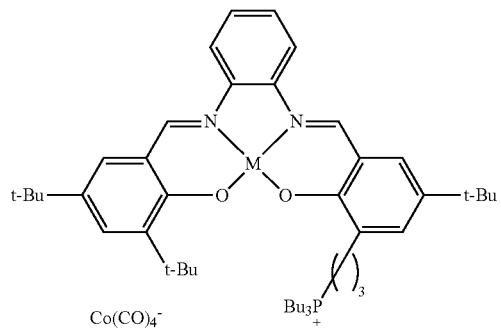
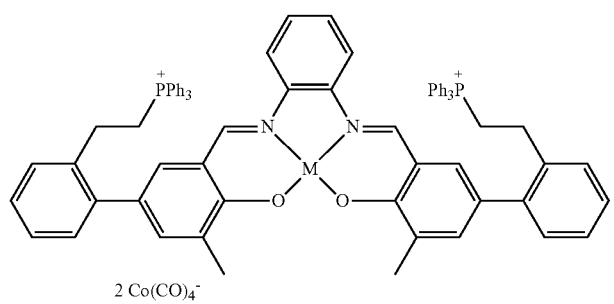
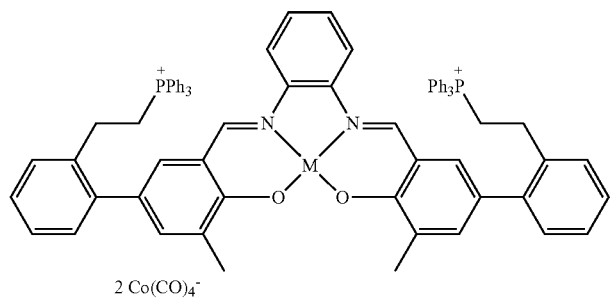
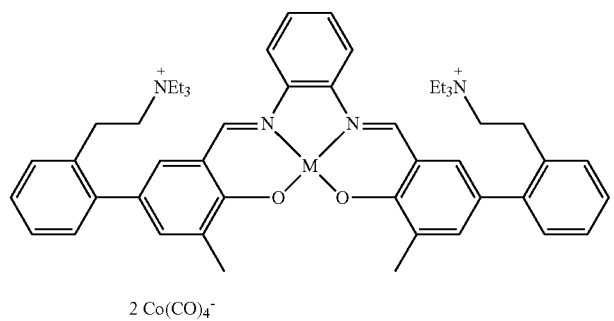
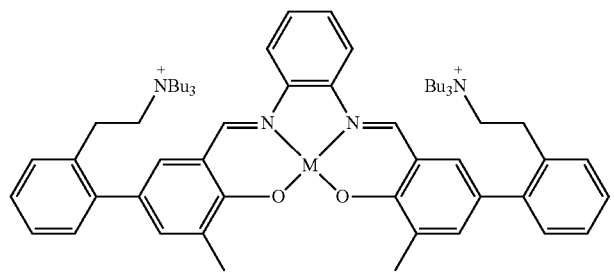

CATALYST TABLE 2-continued
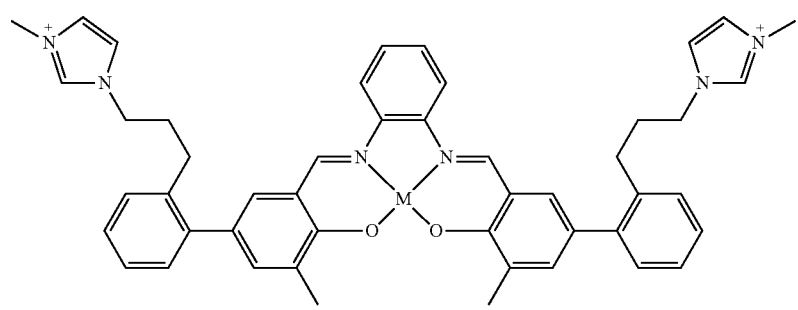
2 Co(CO)$_4^-$
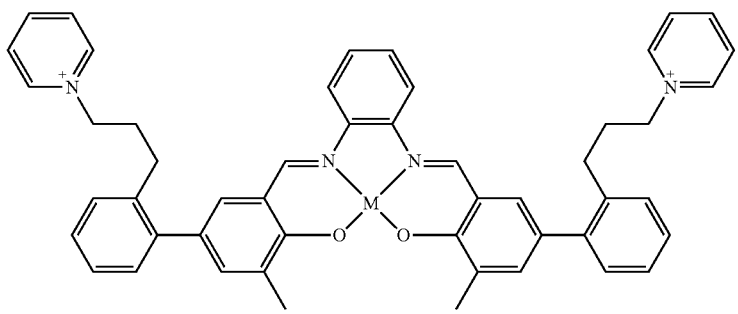
2 Co(CO)$_4^-$
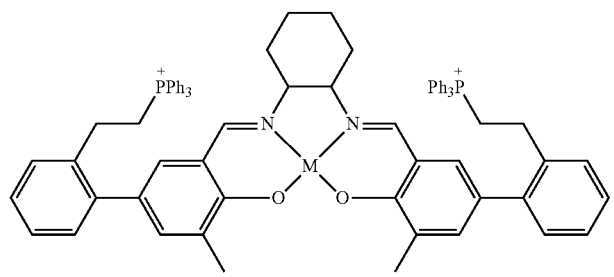
2 Co(CO)$_4^-$
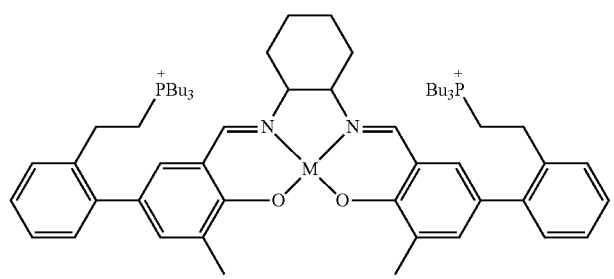
2 Co(CO)$_4^-$ CATALYST TABLE 2-continued
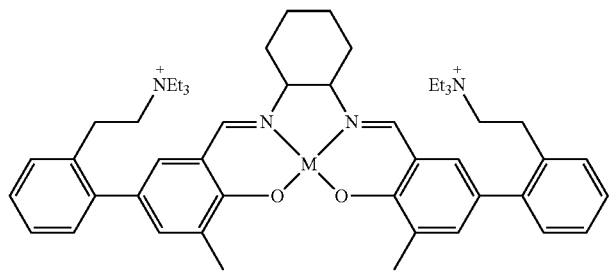
2 Co(CO)$_4^-$
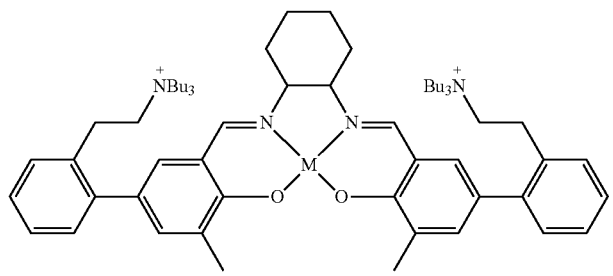
2 Co(CO)$_4^-$
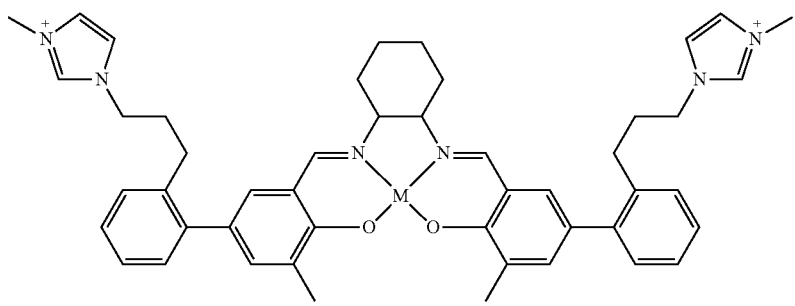
2 Co(CO)$_4^-$
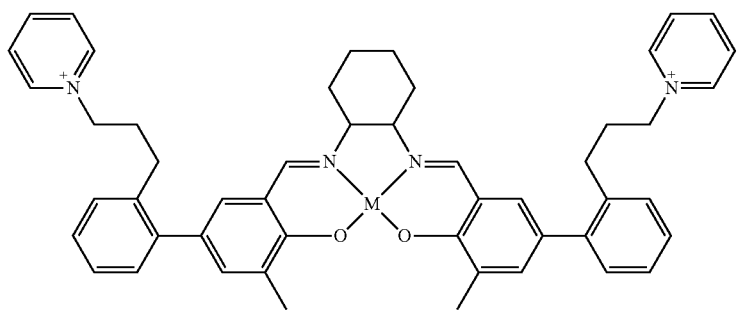
2 Co(CO)$_4^-$ In certain embodiments, catalysts of the present invention include a complex chosen from Catalyst Table 3:
CATALYST TABLE 3
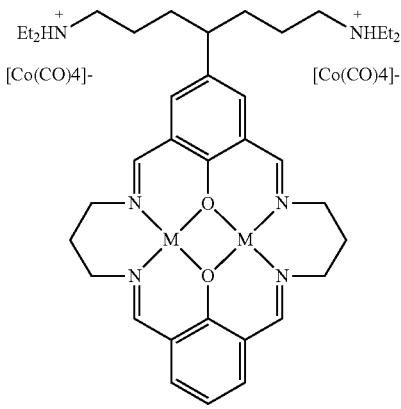
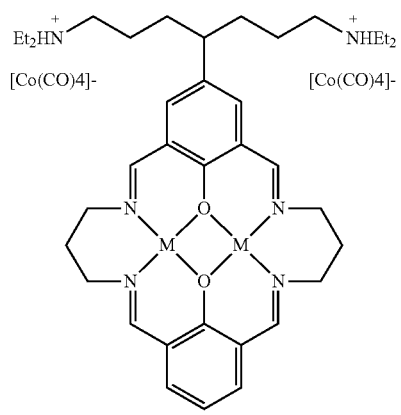
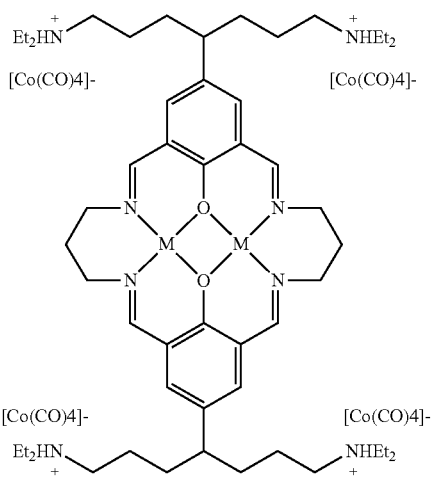
CATALYST TABLE 3-continued
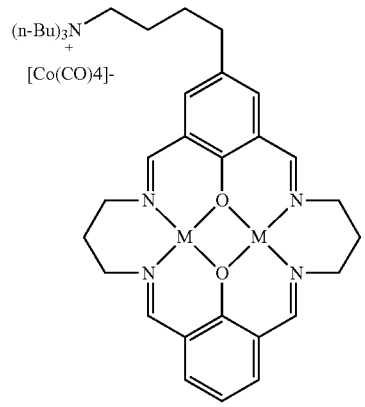
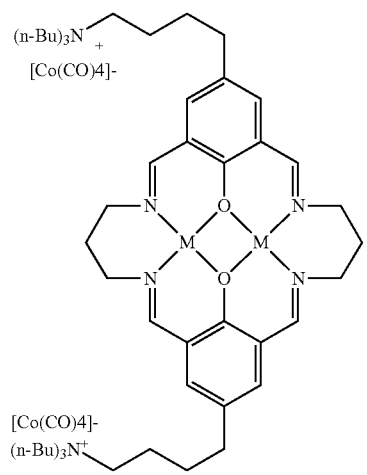
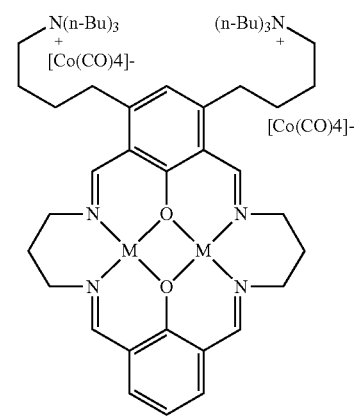

CATALYST TABLE 3-continued
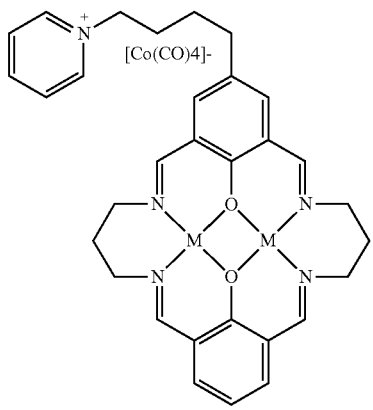
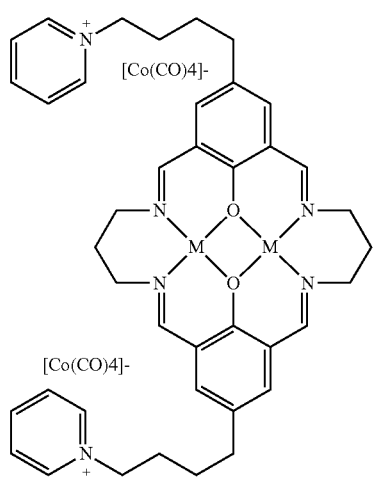
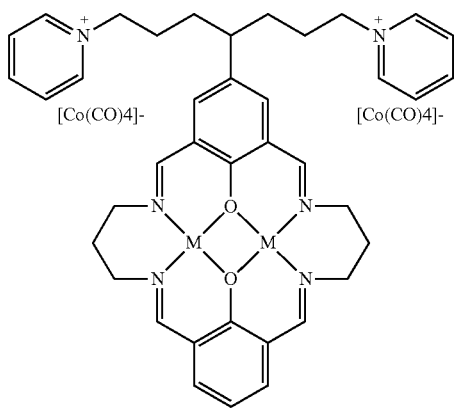
CATALYST TABLE 3-continued
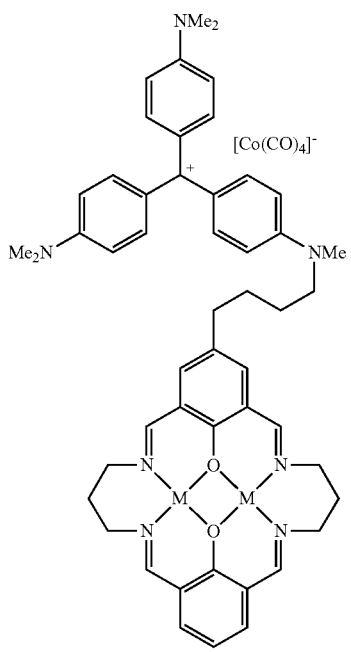
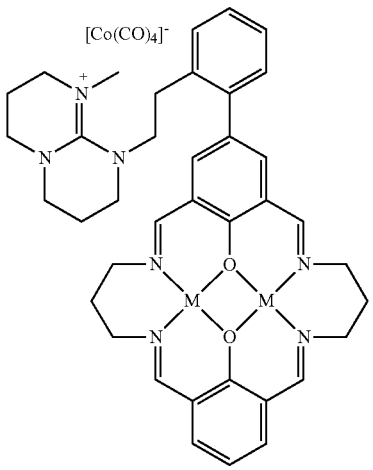
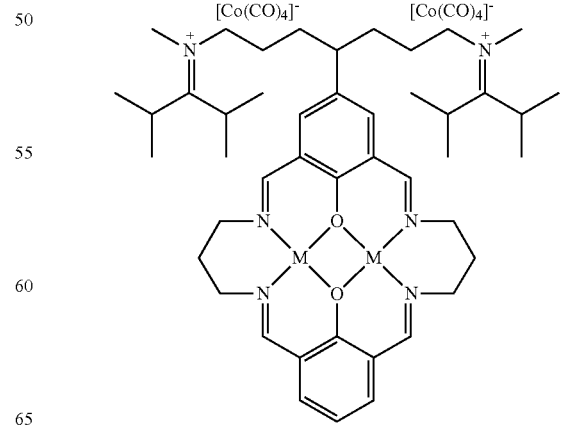

CATALYST TABLE 3-continued
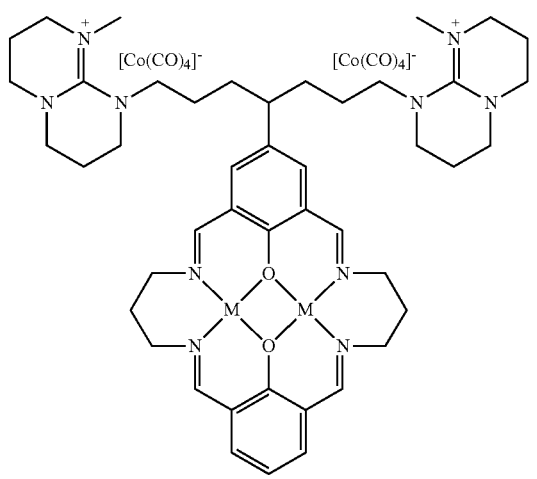
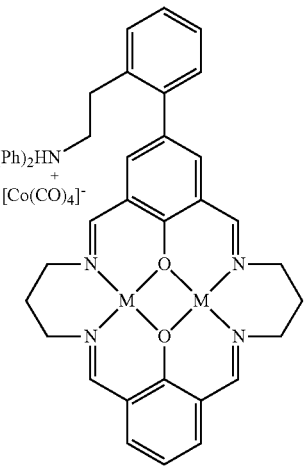
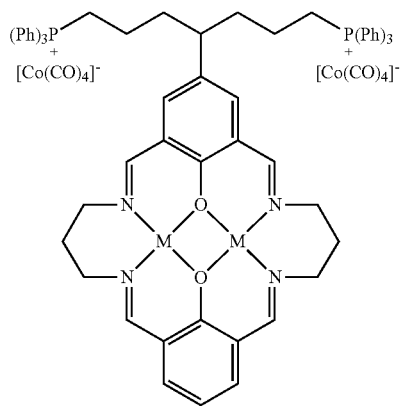
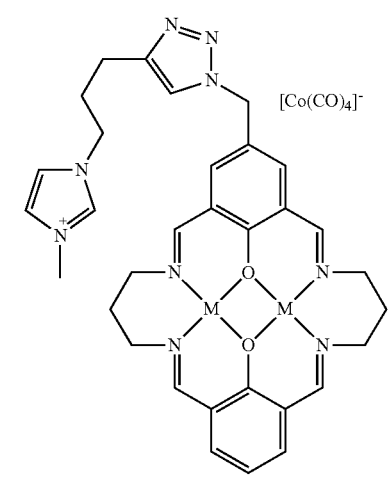
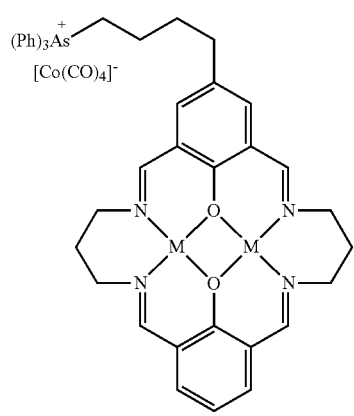
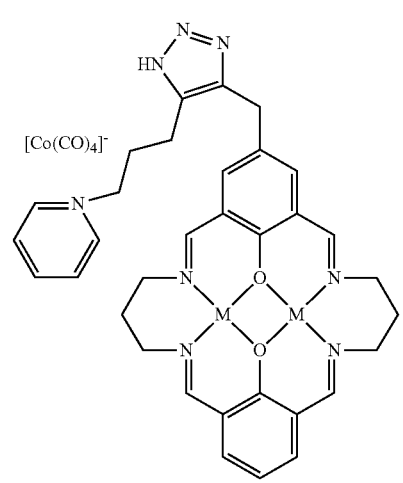

CATALYST TABLE 3-continued
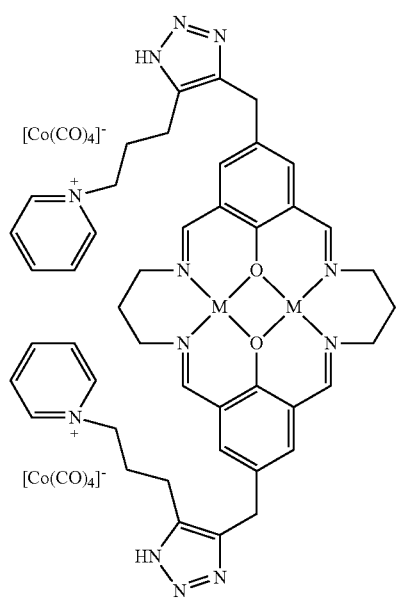
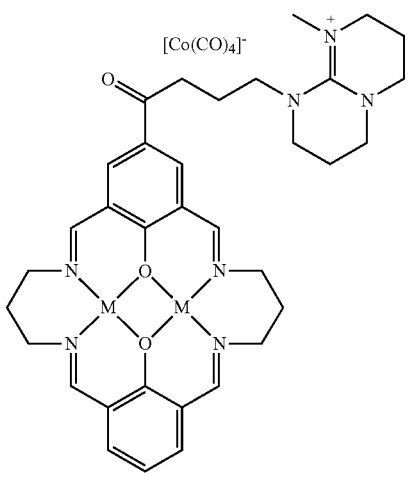
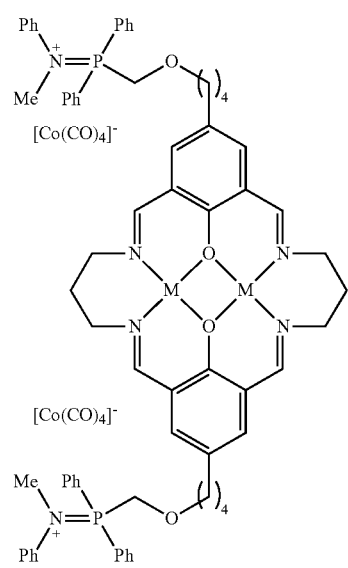
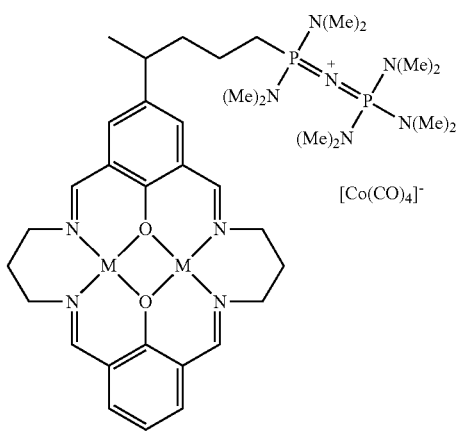
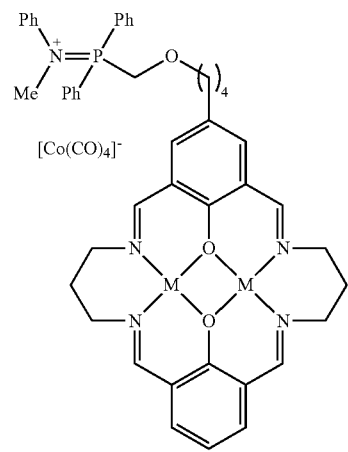
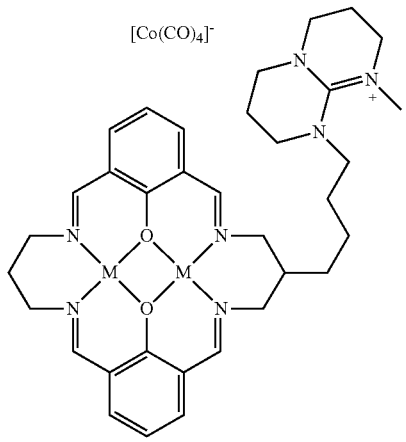

CATALYST TABLE 3-continued
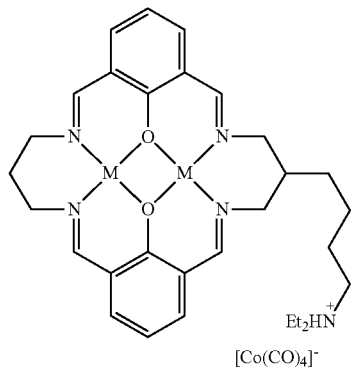
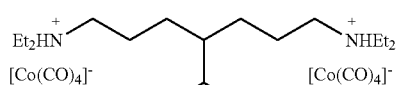
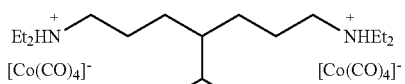
CATALYST TABLE 3-continued
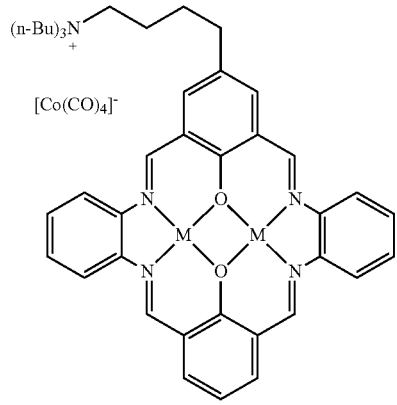
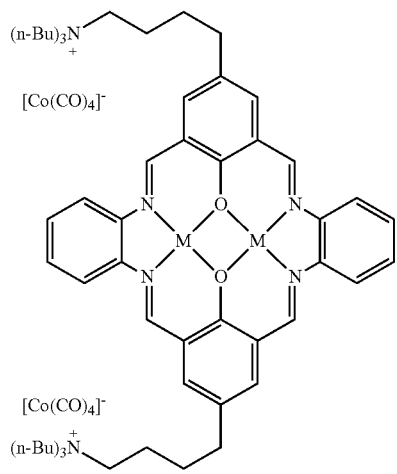
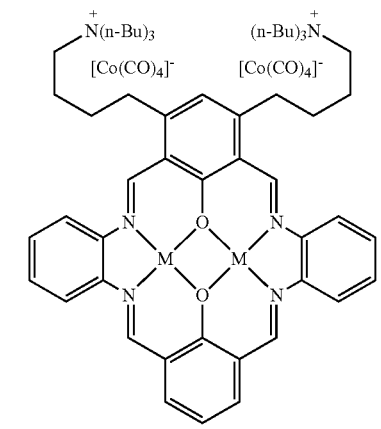

CATALYST TABLE 3-continued
121
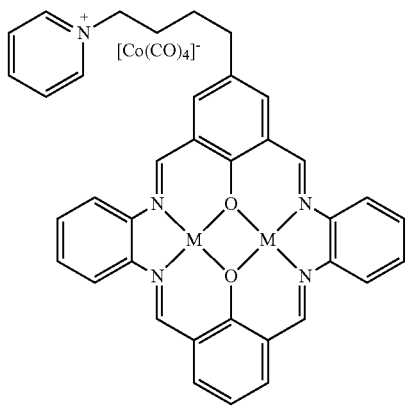
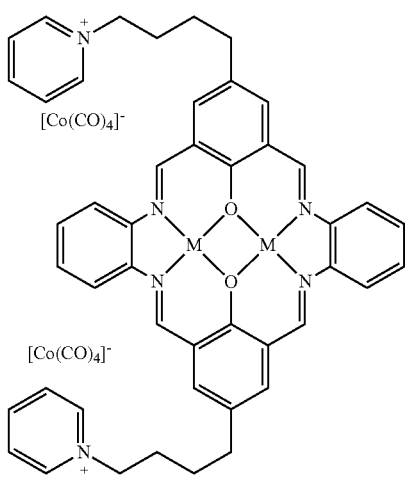
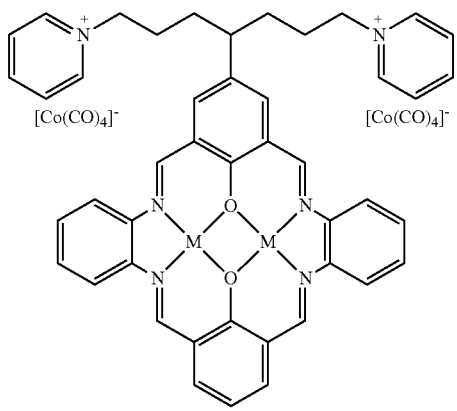
CATALYST TABLE 3-continued
122
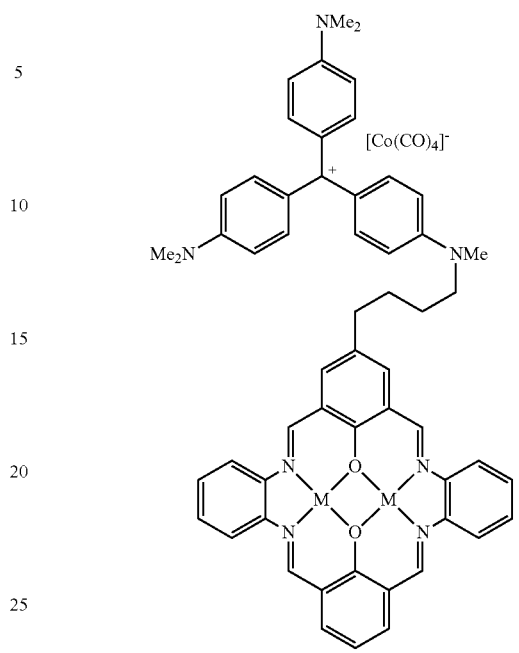
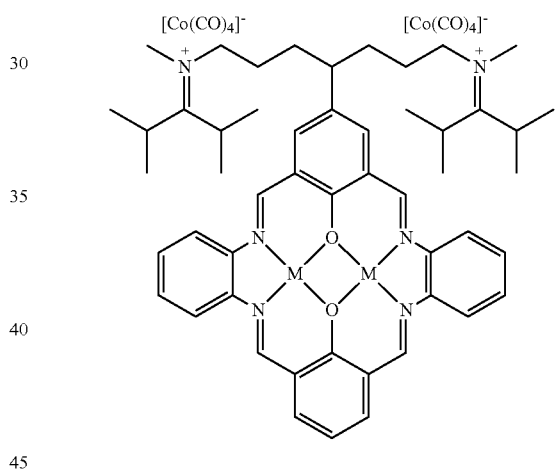
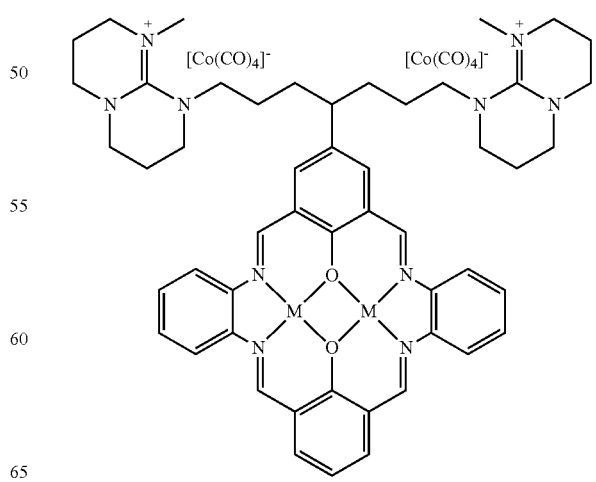

CATALYST TABLE 3-continued
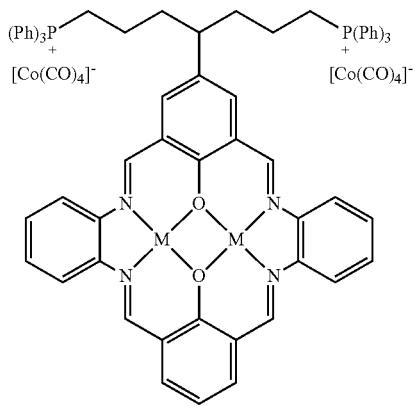
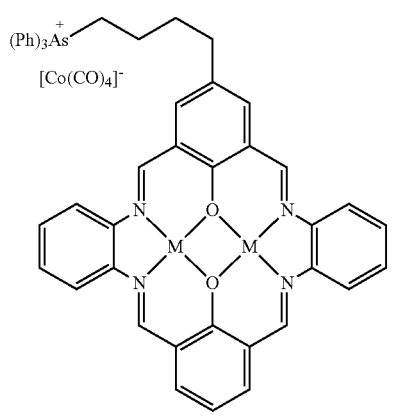
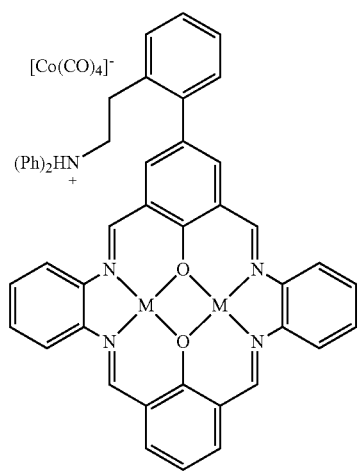
CATALYST TABLE 3-continued
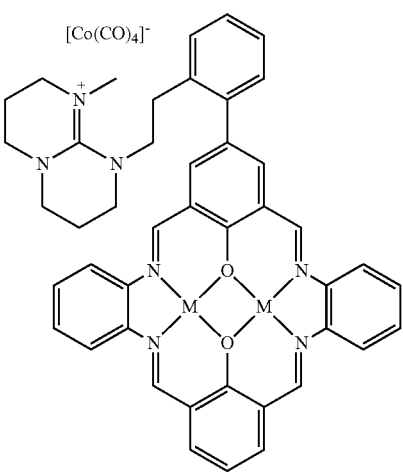
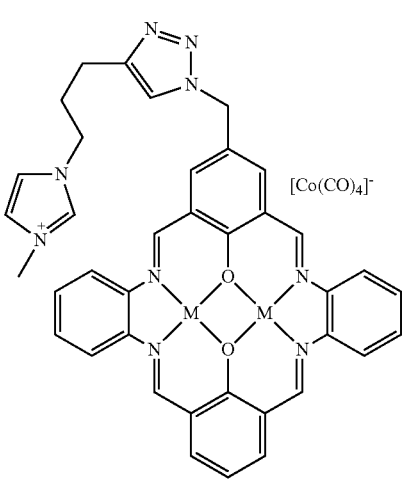
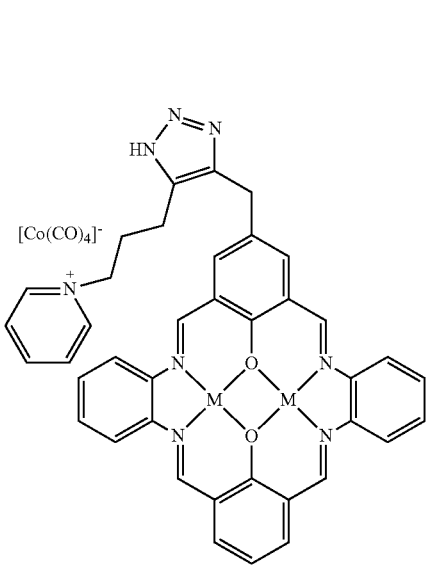

CATALYST TABLE 3-continued
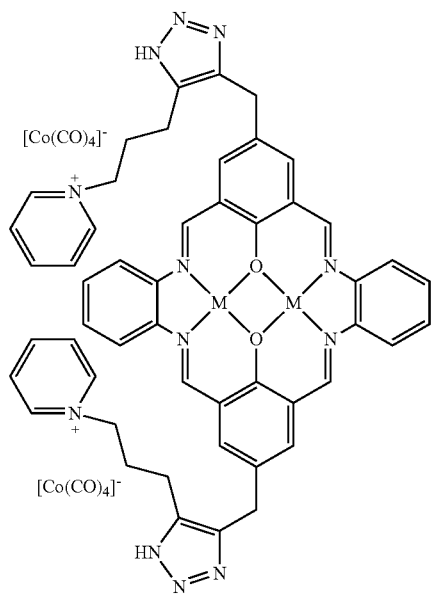
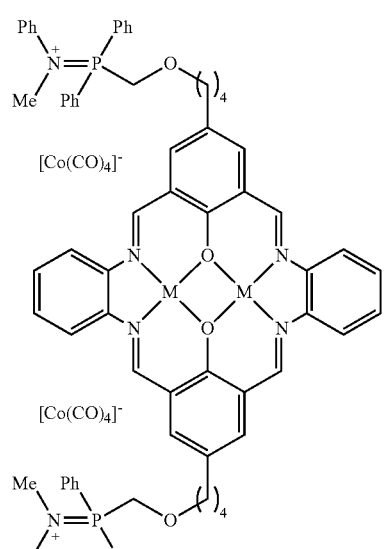
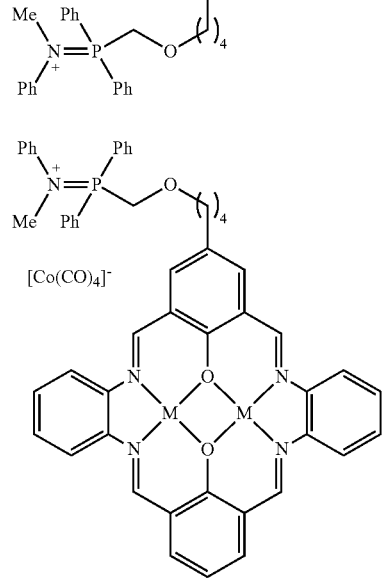
CATALYST TABLE 3-continued
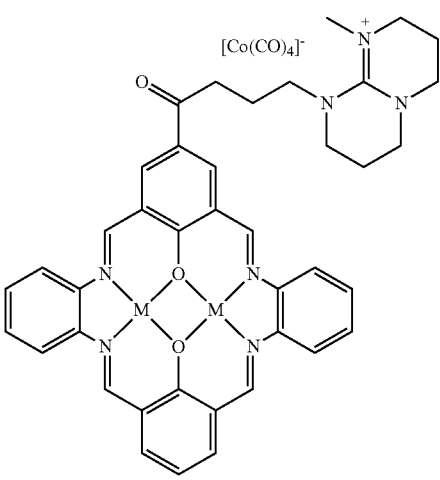
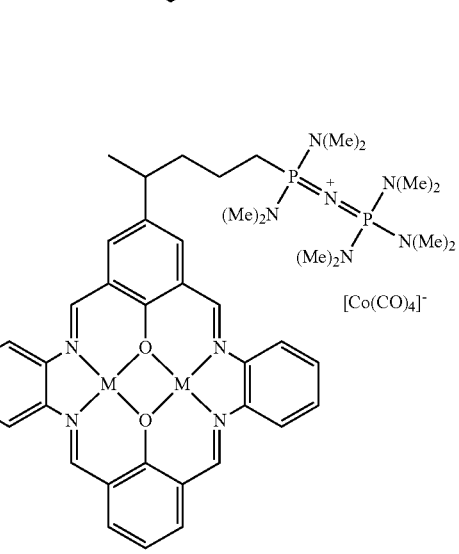
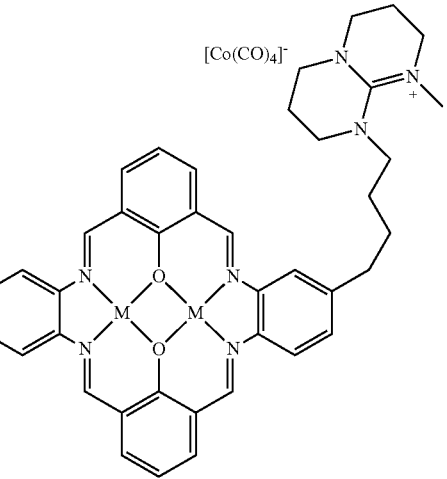

| 127 | 128 |
|---|---|
| CATALYST TABLE 3-continued | CATALYST TABLE 3-continued |
| 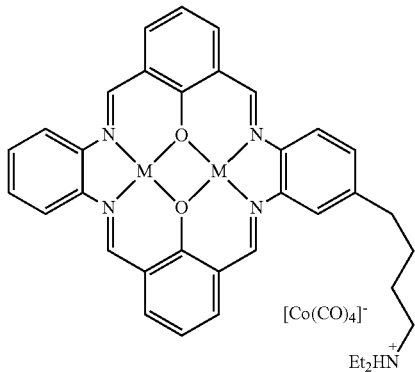 | 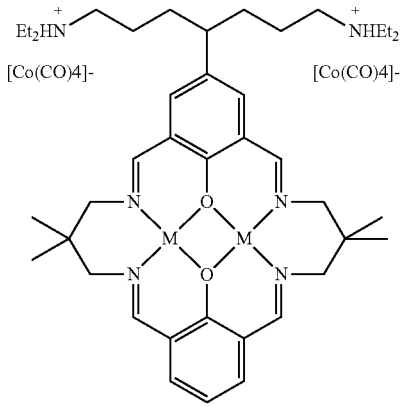 |
| 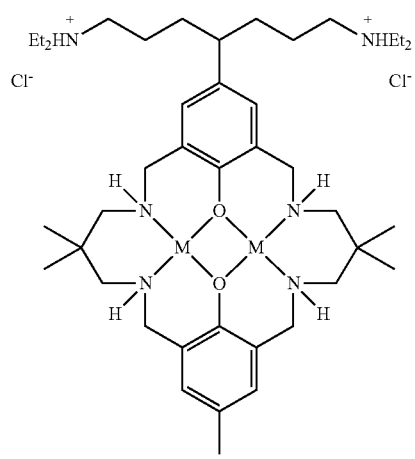 | 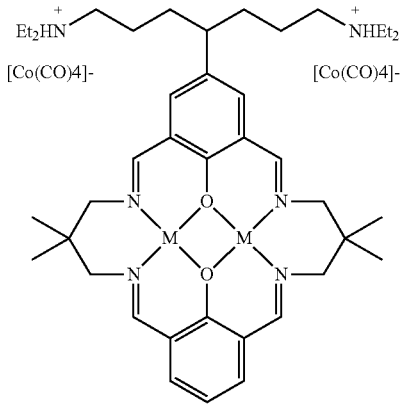 |
| 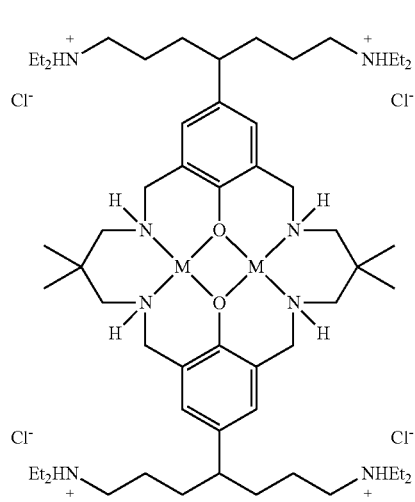 | 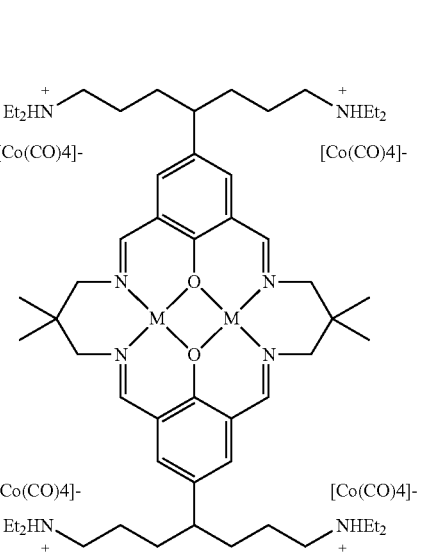 |

CATALYST TABLE 3-continued
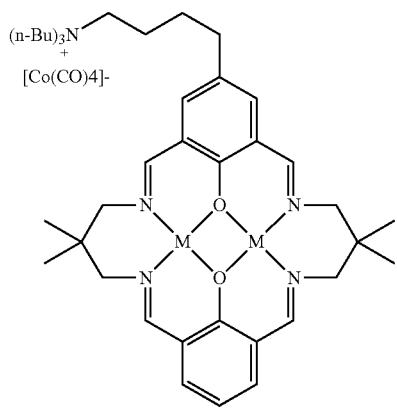
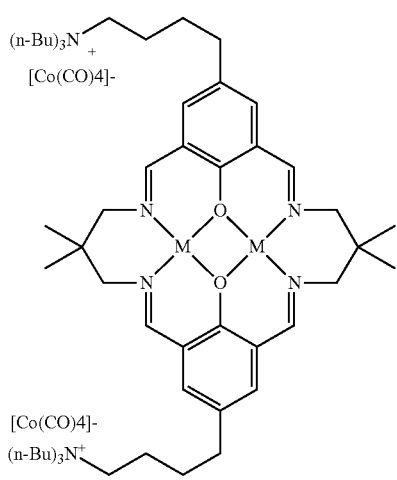
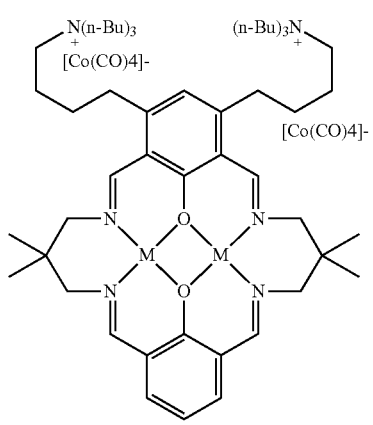
CATALYST TABLE 3-continued
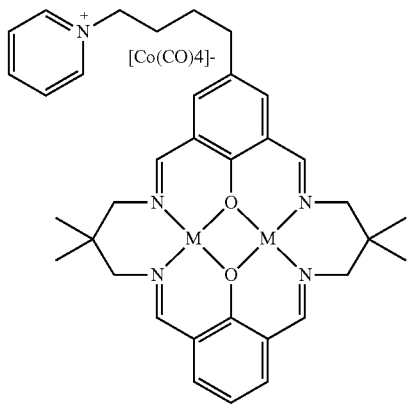
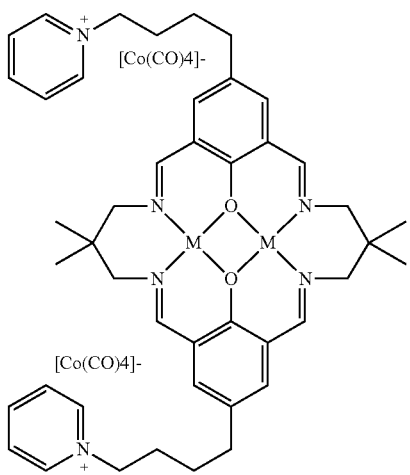
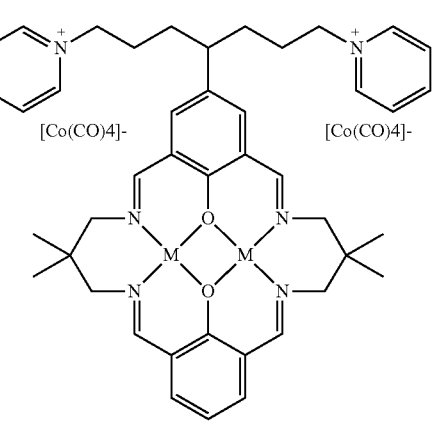

CATALYST TABLE 3-continued
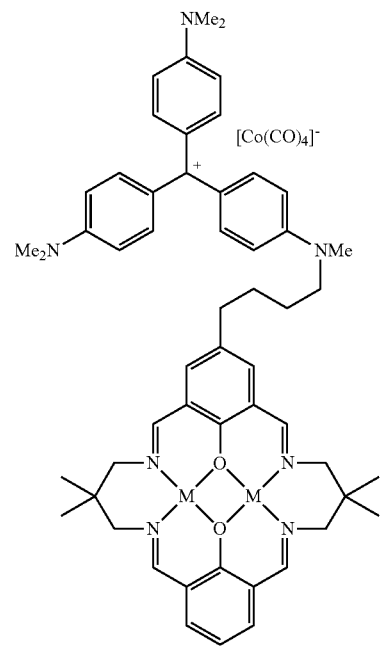
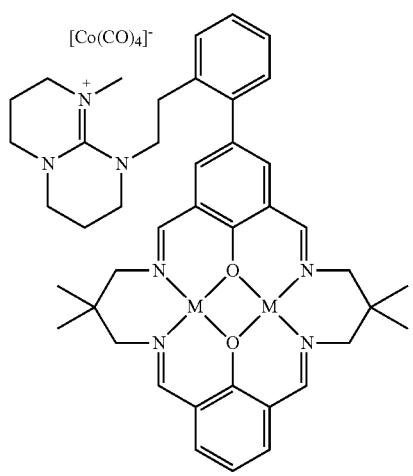
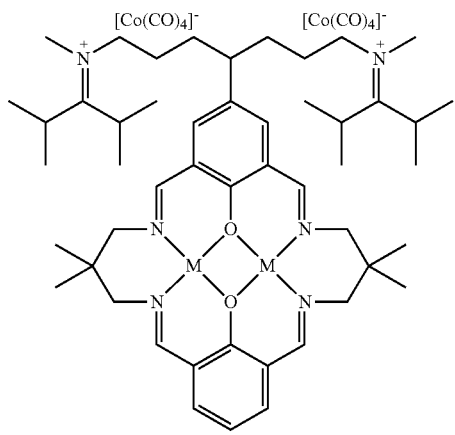
CATALYST TABLE 3-continued
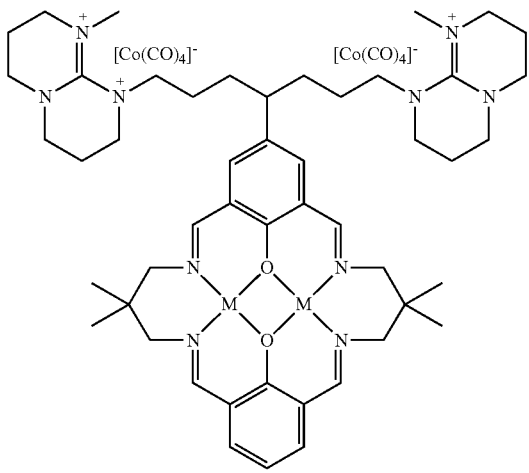
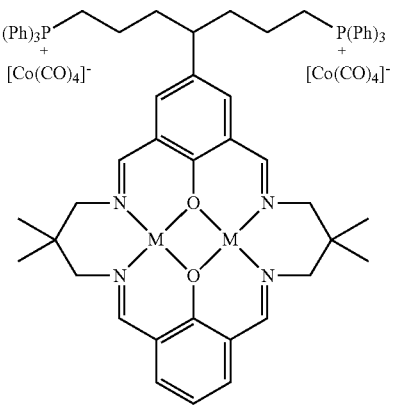
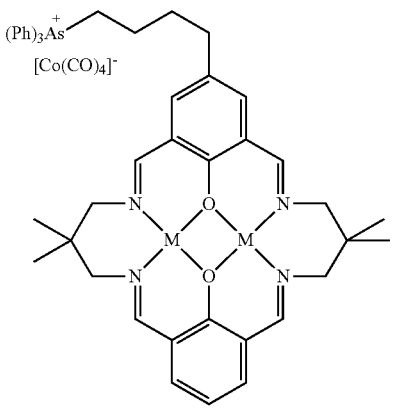

133
CATALYST TABLE 3-continued
134
CATALYST TABLE 3-continued
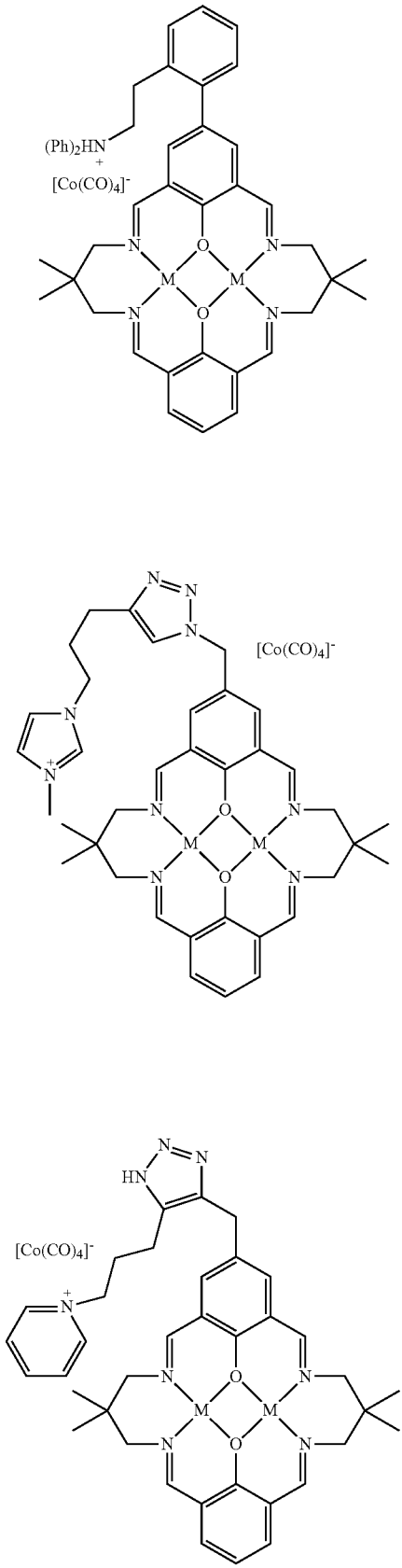
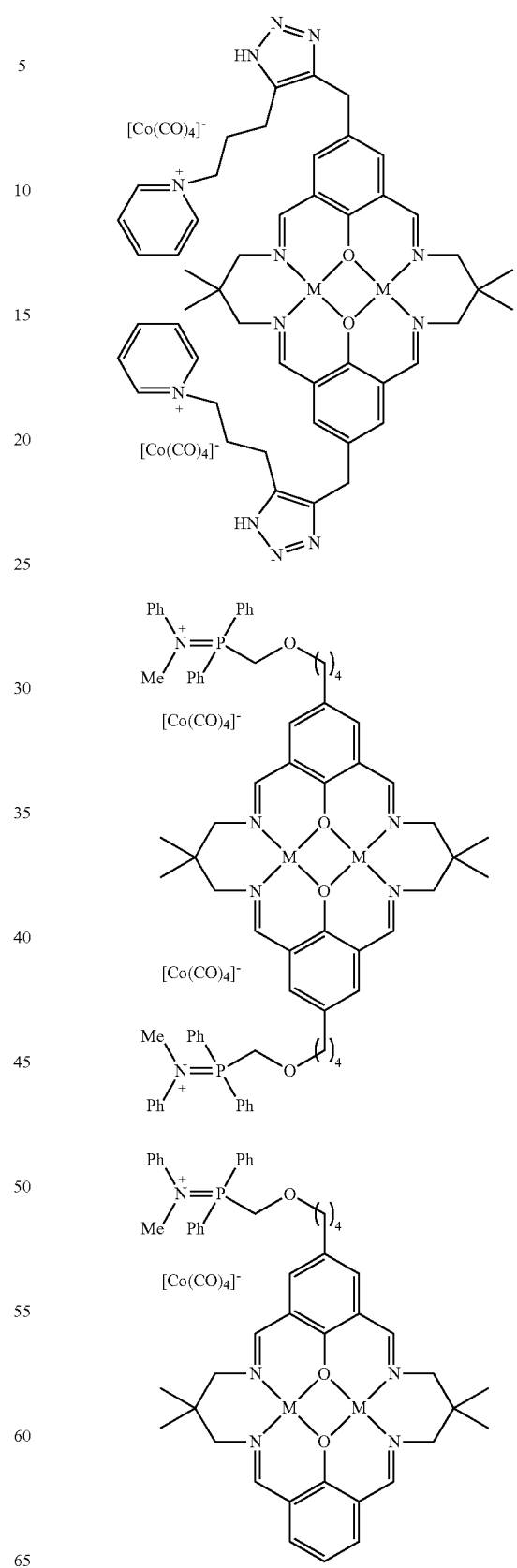

CATALYST TABLE 3-continued
135
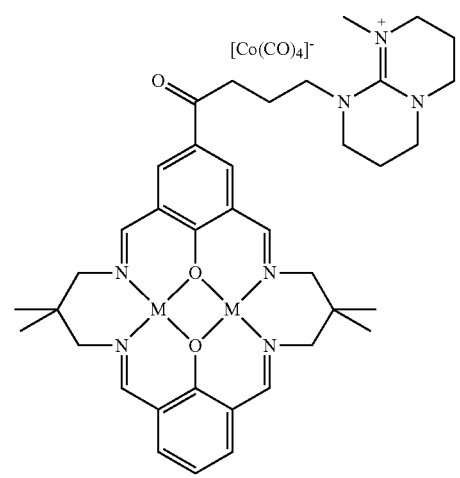
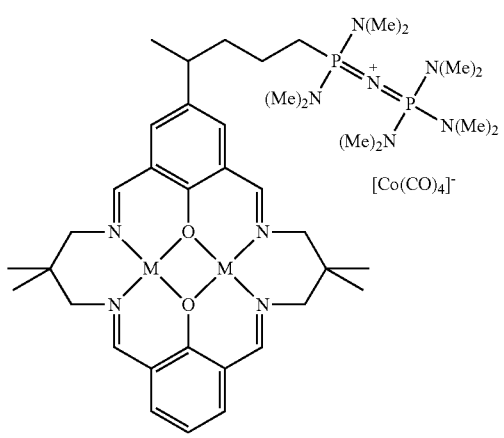
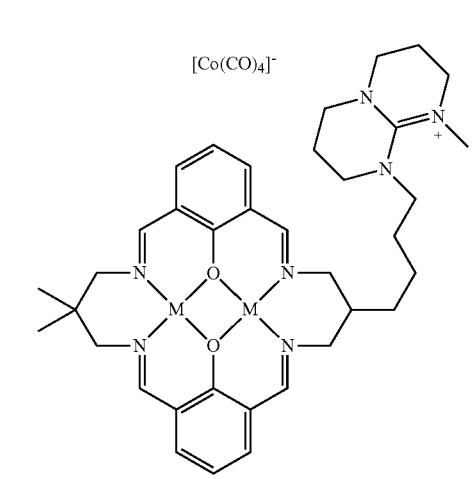
CATALYST TABLE 3-continued
136
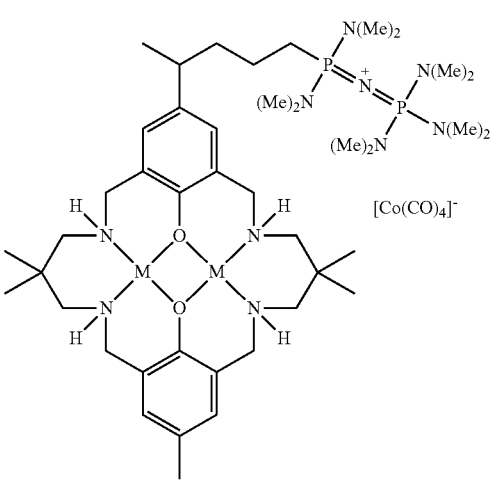
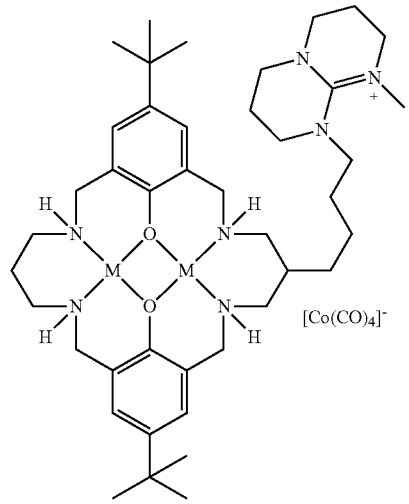
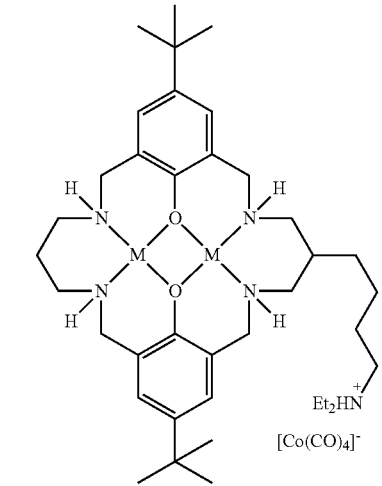

CATALYST TABLE 3-continued
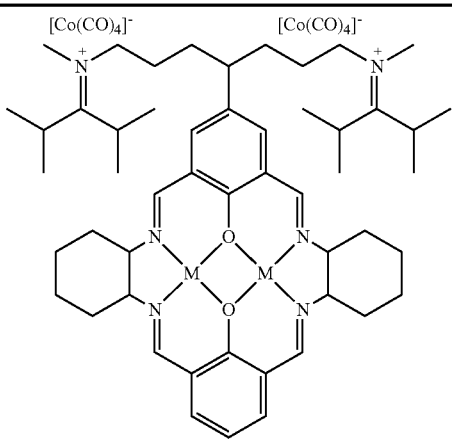
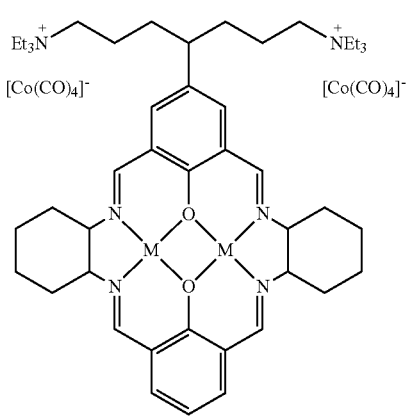
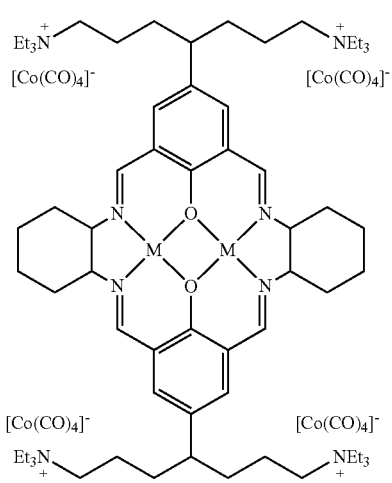
CATALYST TABLE 3-continued
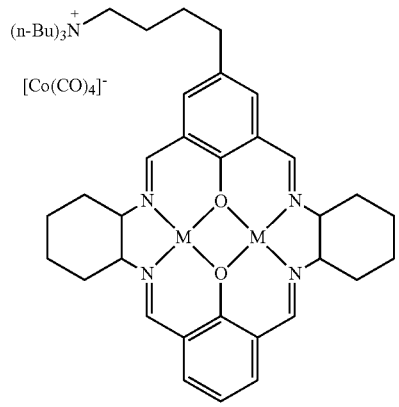
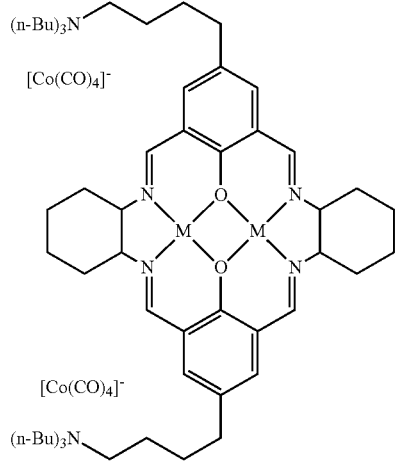
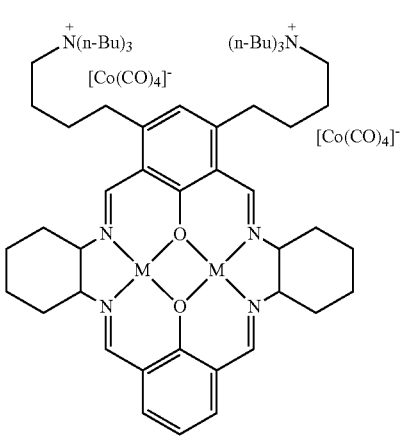

CATALYST TABLE 3-continued
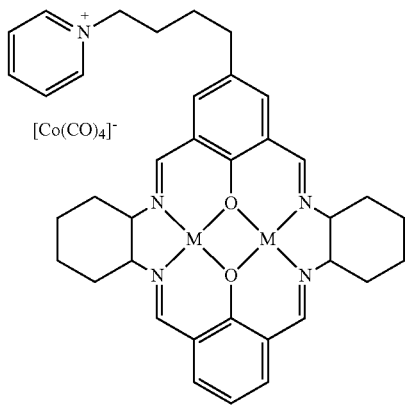
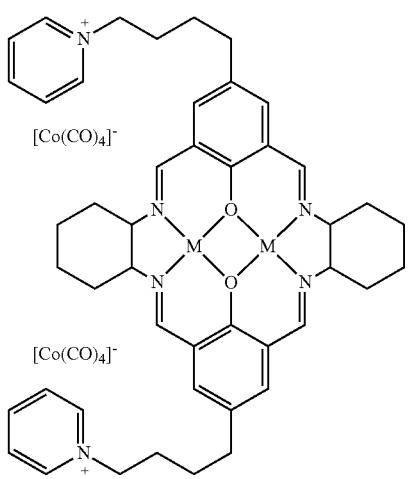
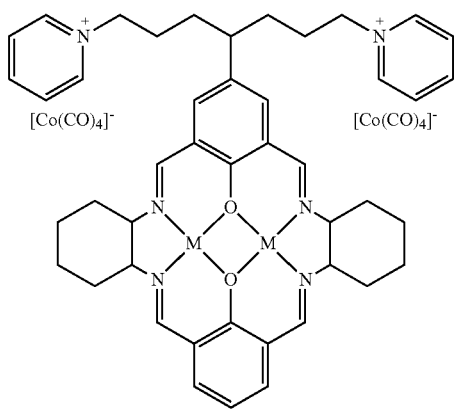
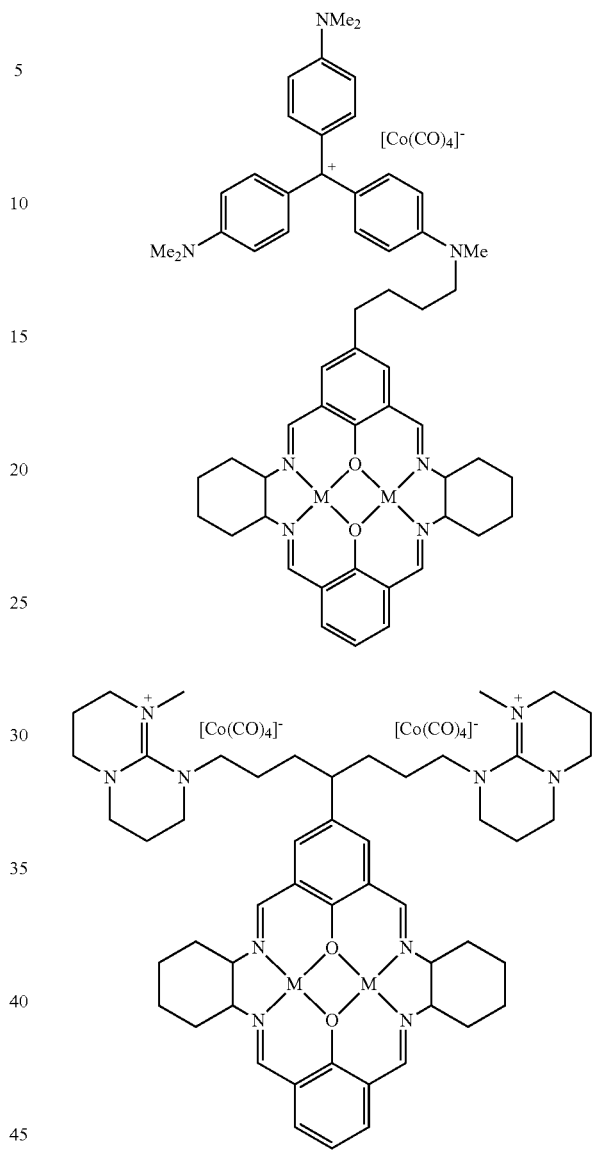
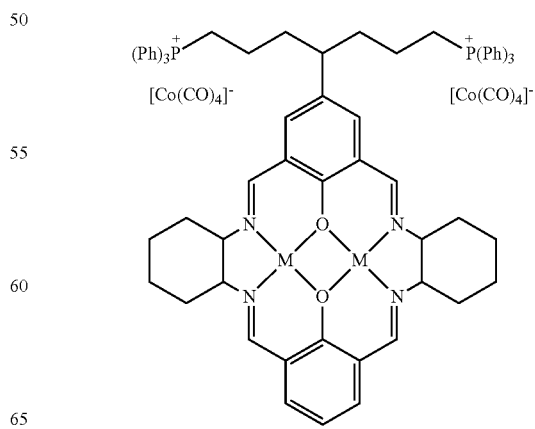

CATALYST TABLE 3-continued
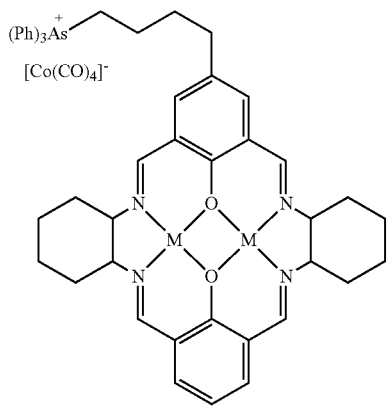
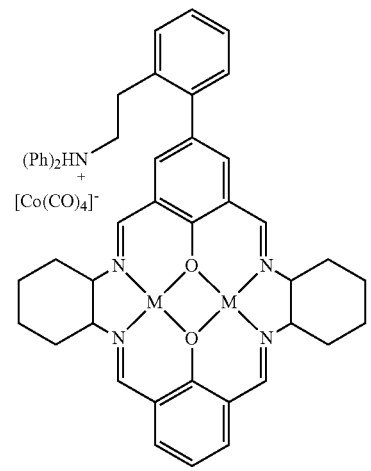
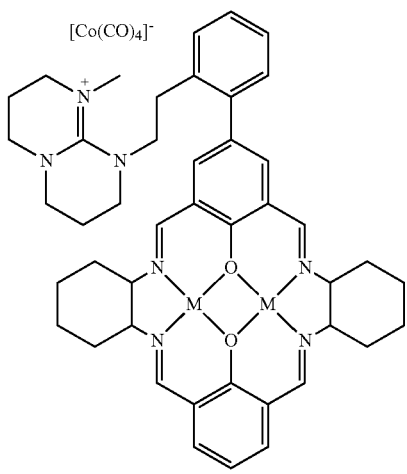
CATALYST TABLE 3-continued
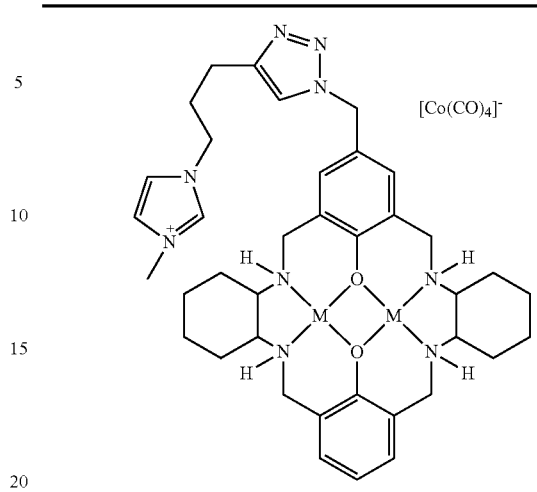
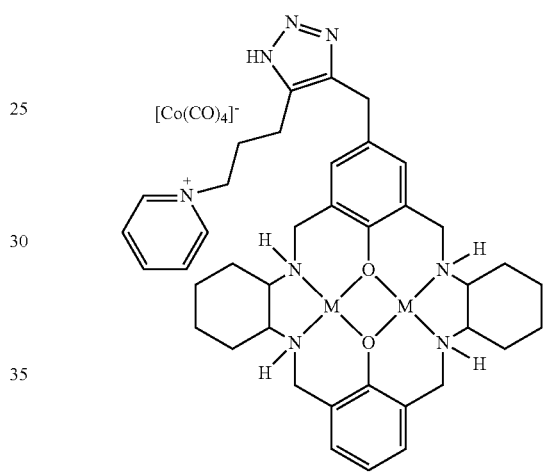
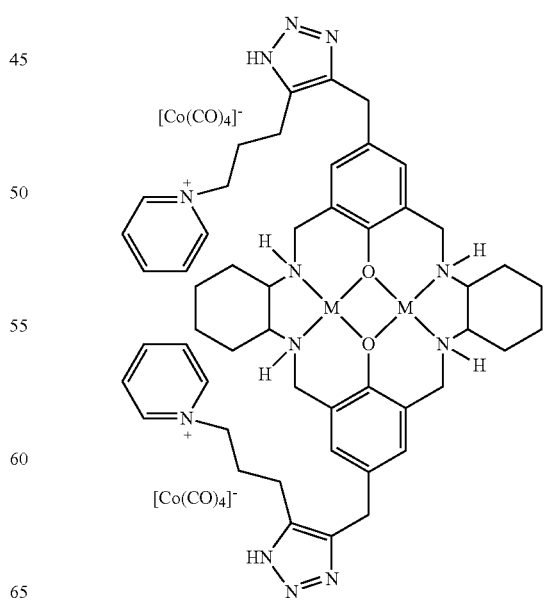

143
CATALYST TABLE 3-continued
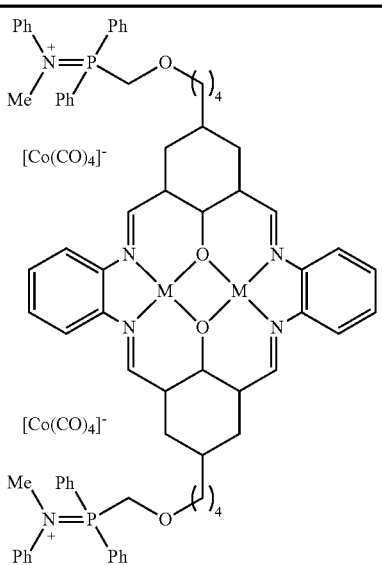
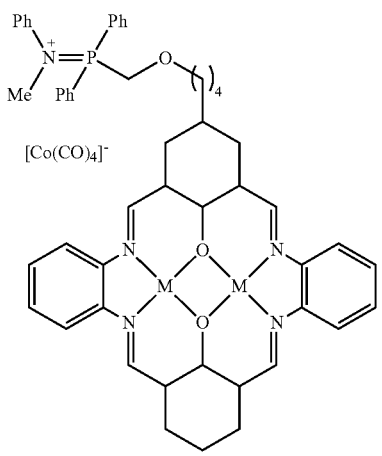
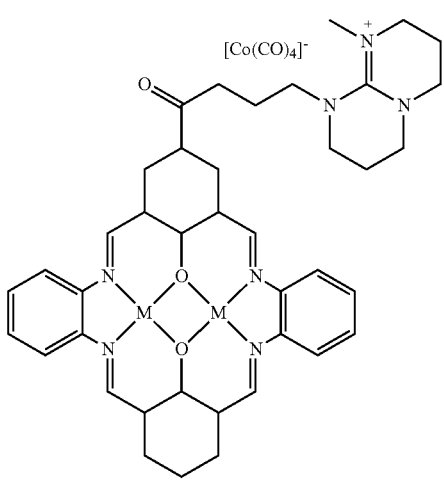
144
CATALYST TABLE 3-continued
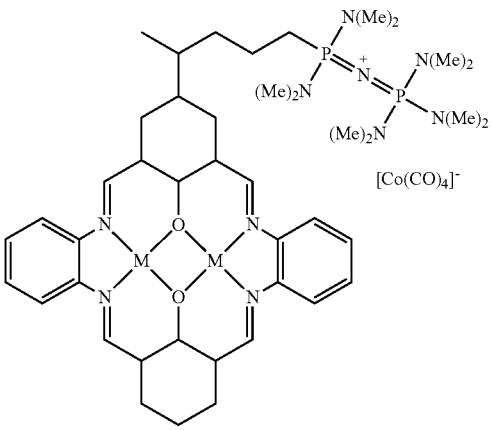
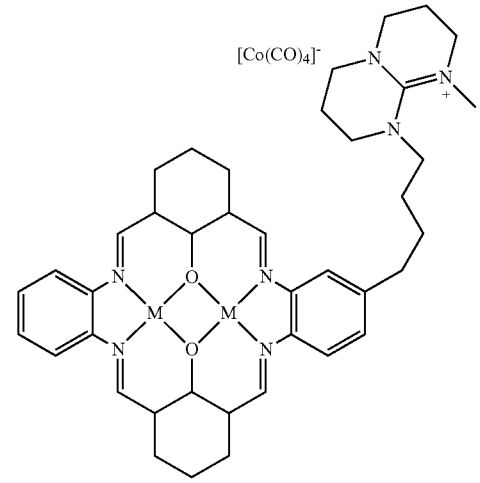
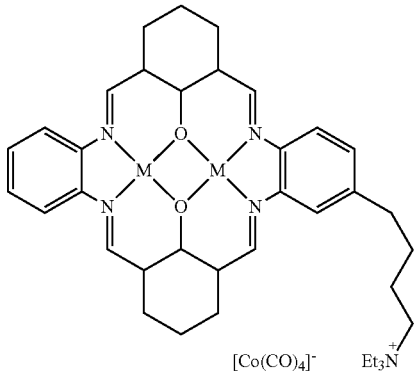

CATALYST TABLE 3-continued
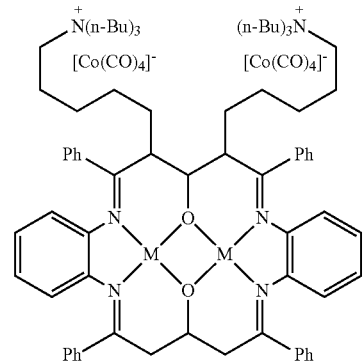
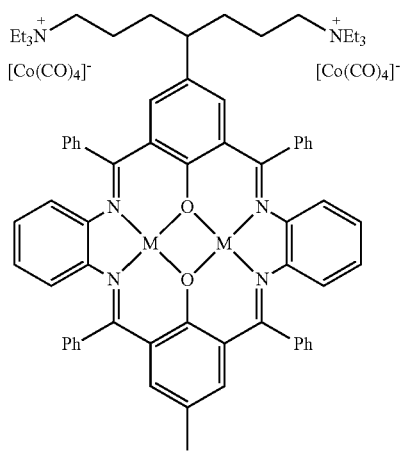
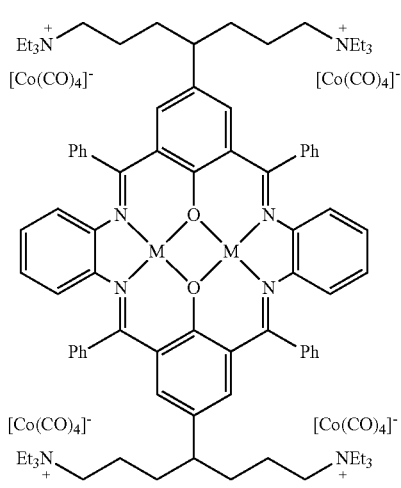
CATALYST TABLE 3-continued
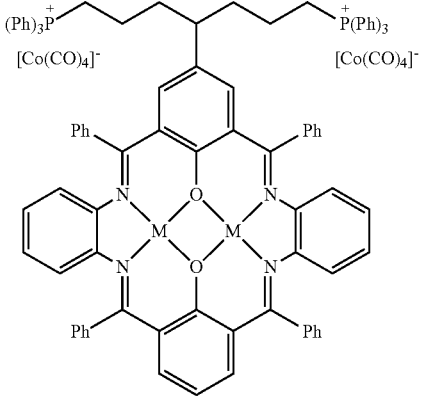
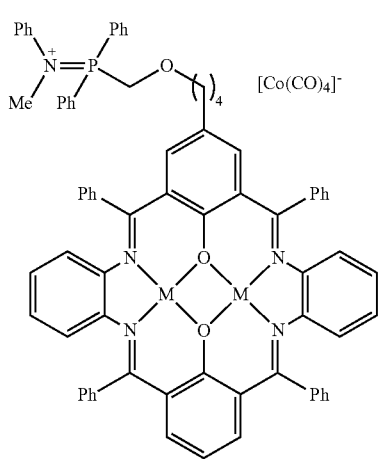
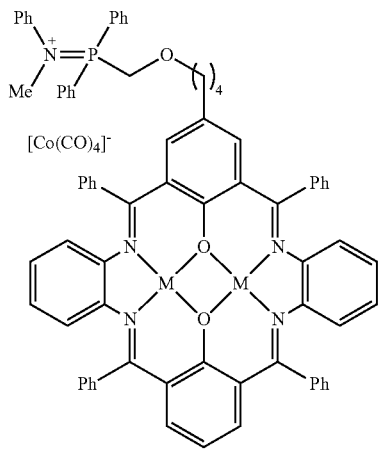

147
CATALYST TABLE 3-continued
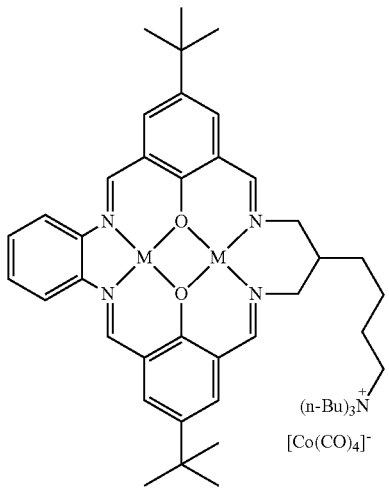
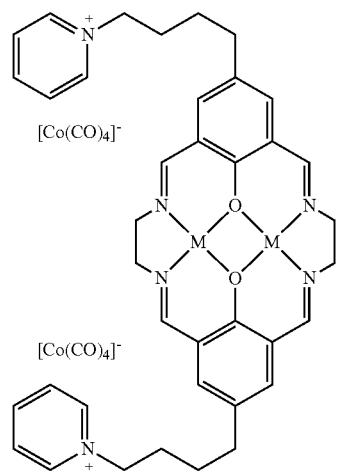
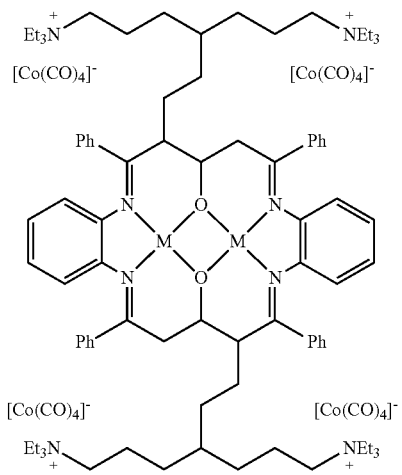
148
CATALYST TABLE 3-continued
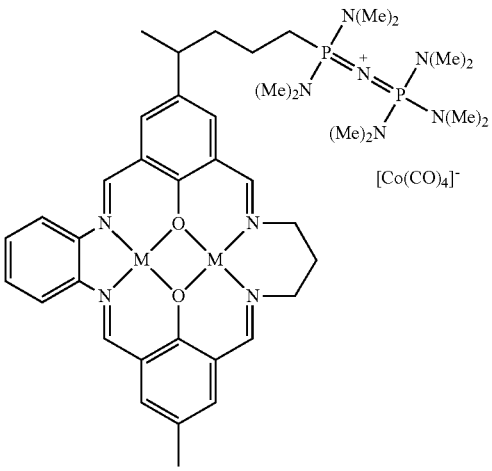
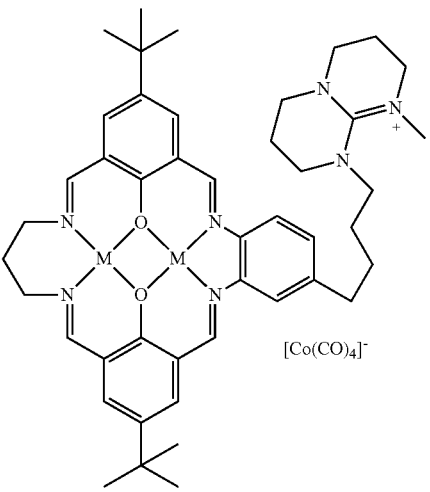

149
CATALYST TABLE 3-continued
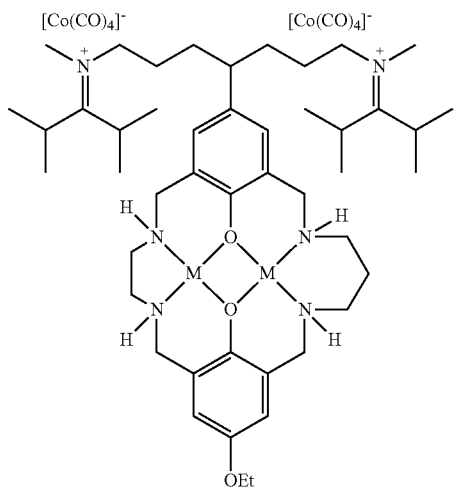
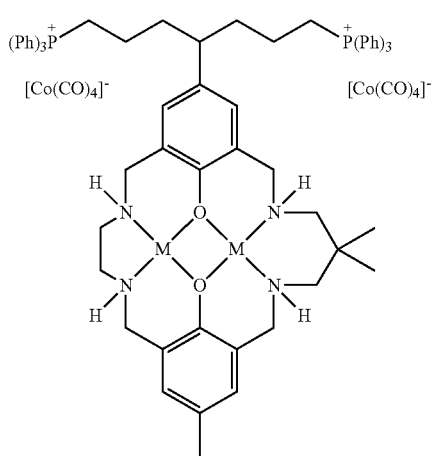
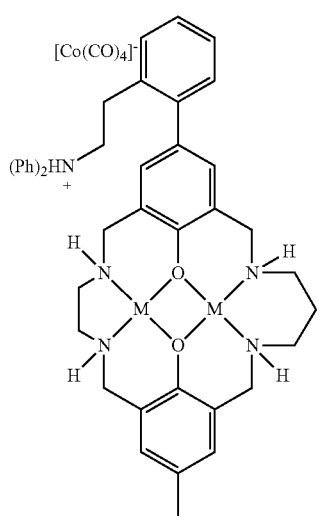
150
CATALYST TABLE 3-continued
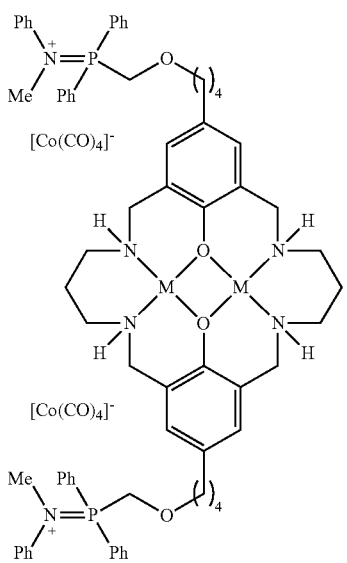
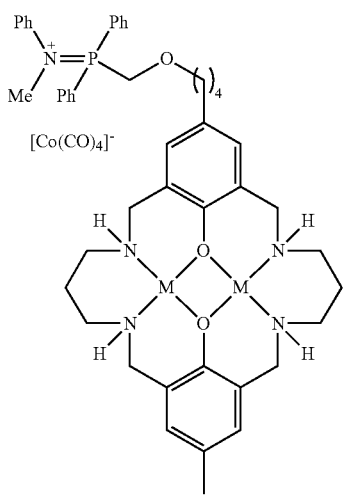
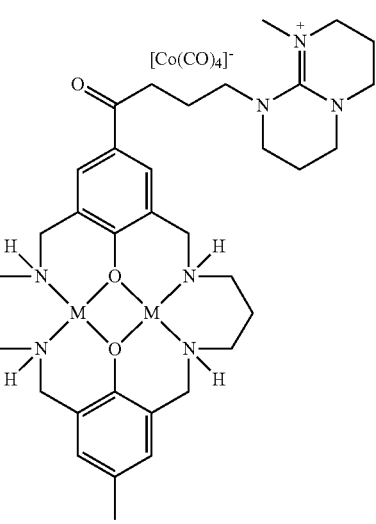
In certain embodiments, each occurrence of M in any compound of Catalyst Tables 1-3 comprises a moiety:

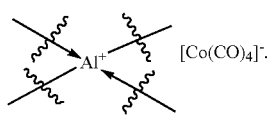

In certain embodiments, each occurrence of M in any compound of Catalyst Tables 1-3 comprises a moiety:

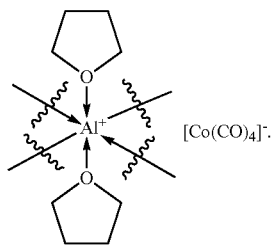

In certain embodiments, each occurrence of M in any compound of Catalyst Tables 1-3 comprises a moiety:

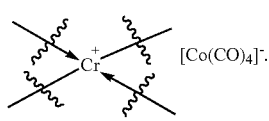

In certain embodiments, each occurrence of M in any compound of Catalyst Tables 1-3 comprises a moiety:

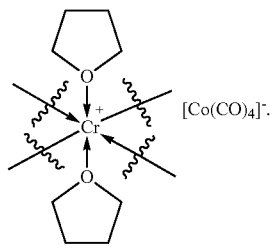

In certain embodiments, the tetracarbonyl cobaltate anions shown associated with any of the compounds in Catalyst Tables 1-3 are replaced by $[Rh(CO)_4]^-$. In certain embodiments, the tetracarbonyl cobaltate anions shown associated with any of the compounds in Catalyst Tables 1-3 are replaced by $[Fe(CO)_5]^{2-}$. In certain embodiments, the tetracarbonyl cobaltate anions shown associated with any of the compounds in Catalyst Tables 1-3 are replaced by $[Mn(CO)_5]^-$.

In certain embodiments, catalysts of the present invention are selected from the group consisting of:

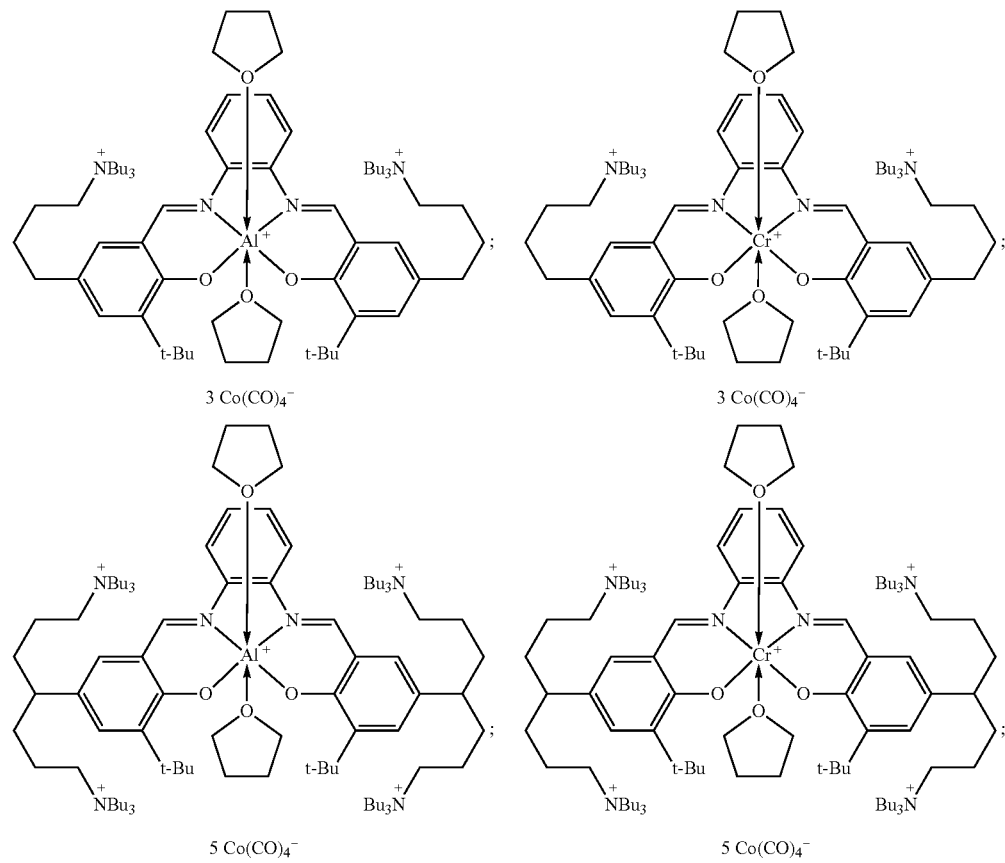

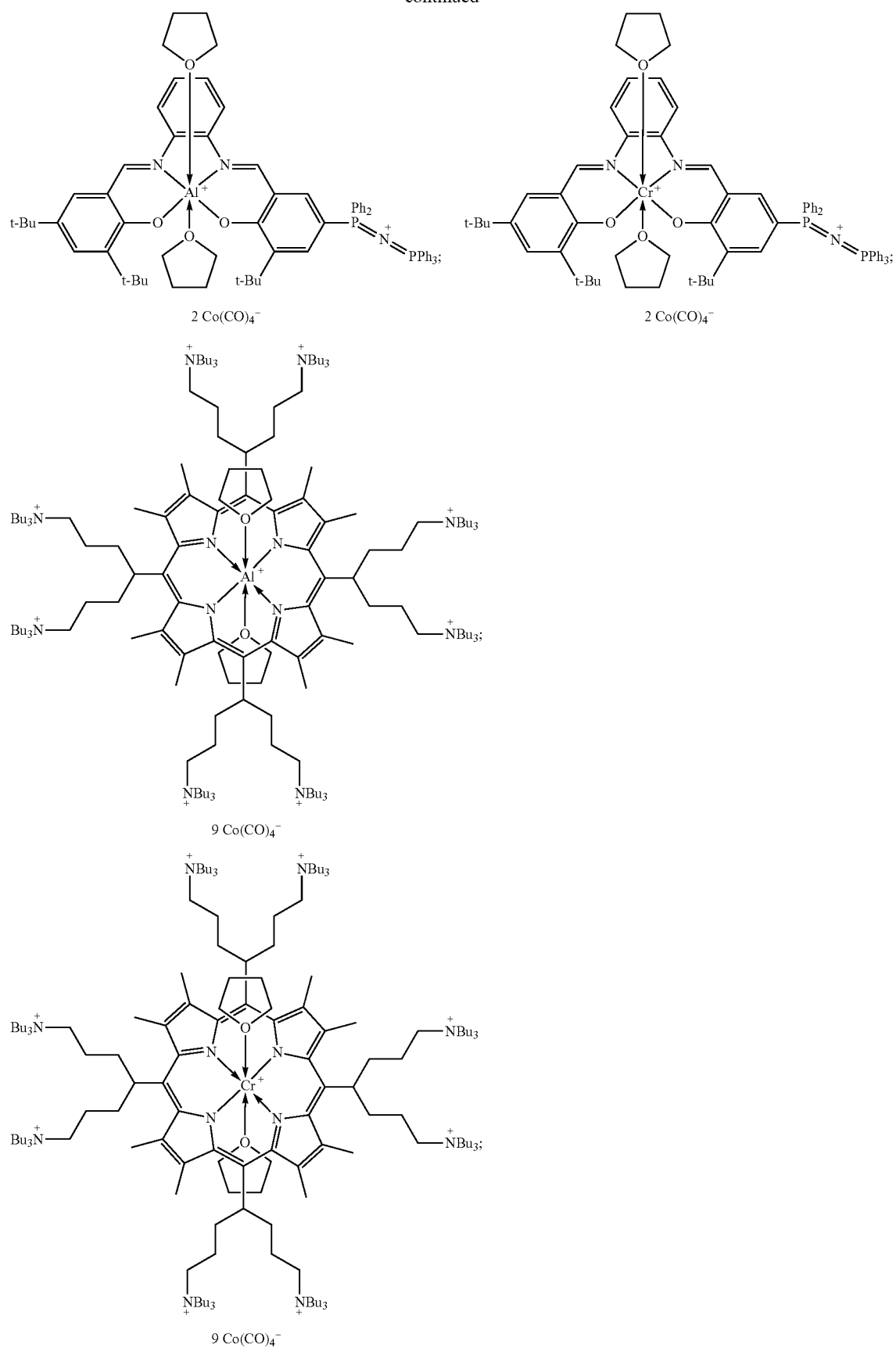

-continued
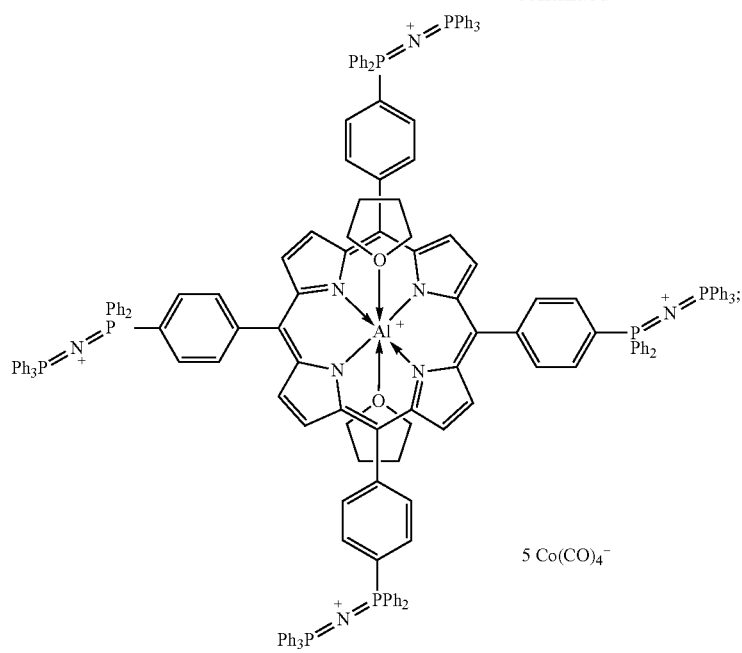
5 Co(CO)$_4^-$
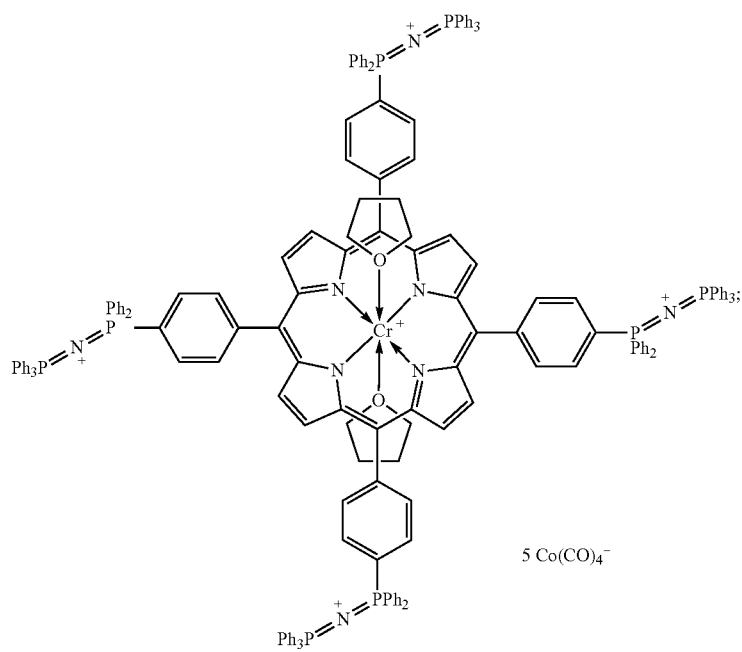
5 Co(CO)$_4^-$

-continued

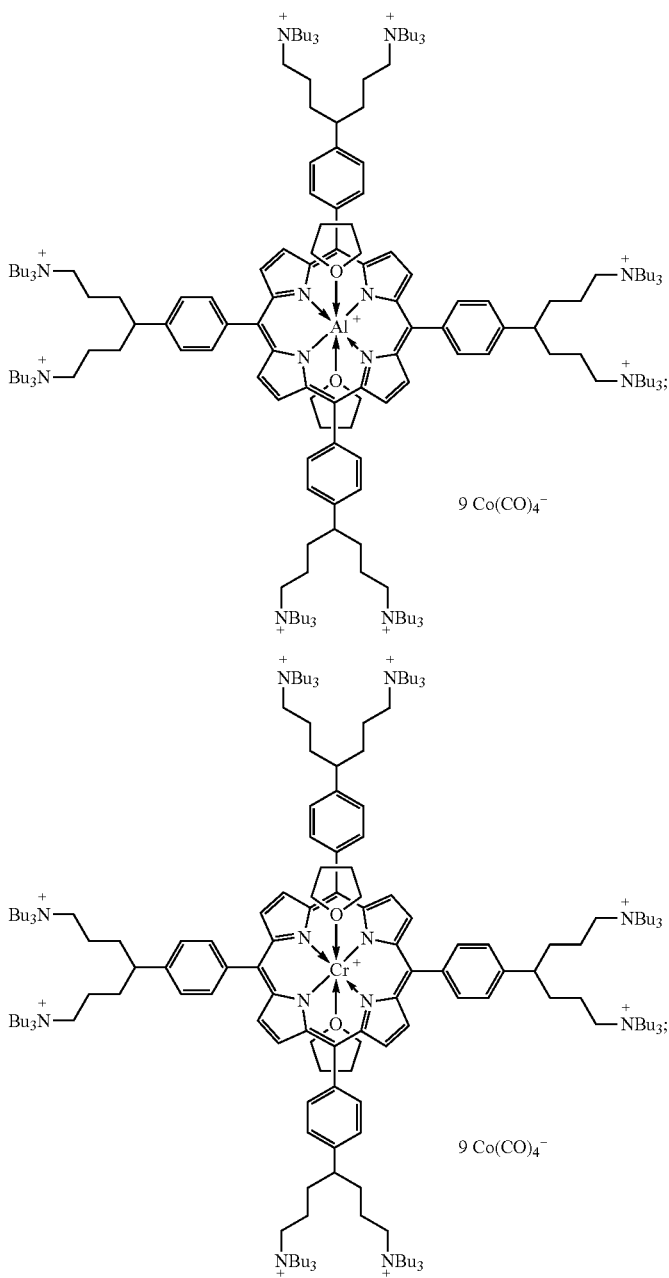

9 Co(CO)$_4^-$

9 Co(CO)$_4^-$

VI. Carbonylation Methods

In another aspect, the present invention provides methods of carbonylating heterocycles using the catalysts disclosed hereinabove. In certain embodiments, the invention encompasses a method comprising the steps:

a) providing a compound having formula:

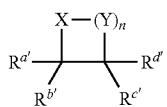

(1)

wherein:
R$^{a'}$ is hydrogen or an optionally substituted group selected from the group consisting of C$_{1-30}$ aliphatic; C$_{1-30}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, or sulfur; and 4- to 7-membered heterocyclic having 1-3 heteroatoms independently selected from the group consisting of nitrogen, oxygen, and sulfur;

each of R$^{b'}$, R$^{c'}$, and R$^{d'}$ is independently hydrogen or an optionally substituted group selected from the group consisting of C$_{1-12}$ aliphatic; C$_{1-12}$heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, or sulfur; and 4- to 7-membered heterocyclic having 1-3 heteroatoms independently selected from the group consisting of nitrogen, oxygen, and sulfur;

wherein any of ($R^{b1}$ and $R^{c1}$), ($R^{c1}$ and $R^{d1}$), and ($R^{a1}$ and $R^{b1}$) can be taken together with their intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally substituted $C_5$-$C_{10}$ heteroaryl;

X is selected from the group consisting of O, S an $NR^{c1}$ where $R^{c1}$ is selected from the group consisting of hydrogen or an optionally substituted group selected from the group consisting of $C_{1-30}$ aliphatic; $C_{1-30}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, or sulfur; and 4- to 7-membered heterocyclic having 1-3 heteroatoms independently selected from the group consisting of nitrogen, oxygen, and sulfur;

n is 0 or 1; and

Y is C=O or $CH_2$;

b) contacting the compound having the formula (1) and carbon monoxide in the presence of any metal complex described above, to provide a product having formula:

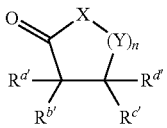
(2)

where $R^{a1}$, $R^{b1}$, $R^{c1}$, $R^{d1}$, and X, correspond to $R^{a1}$, $R^{b1}$, $R^{c1}$, $R^{d1}$, and X, in (1) including $R^{b1}$ and $R^{c1}$ forming a ring if that is the case for (1); and in the case where n for (1) is 0, n for (2) is 0 or 1, and in the case where n for (1) is 1, n for (2) is 1.

In certain embodiments of the carbonylation method described above, n for (1) is 0 so that the formula for (1) becomes:

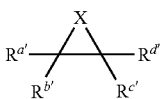
(3)

and the product has the formula:

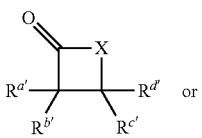
(4)

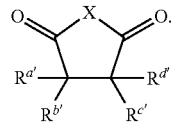
(5)

In certain embodiments of the carbonylation method described above, X for (3) is oxygen so that the formula for (3) becomes an epoxide:

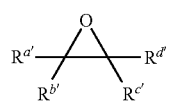
(6)

and the product has the formula:

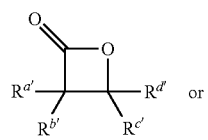
(7)

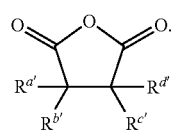
(8)

In certain embodiments, methods of the present invention comprise treating heterocycles where $R^{a1}$, $R^{b1}$, and $R^{c1}$ are —H, and $R^{d1}$ comprises an optionally substituted $C_{1-20}$ aliphatic group. In certain embodiments, methods of the present invention comprise treating heterocycles where $R^{a1}$, $R^{b1}$, $R^{c1}$, and $R^{c1}$ are all —H. In certain embodiments, methods of the present invention comprise treating heterocycles where $R^{a1}$, $R^{b1}$, and $R^{c1}$ are —H, and $R^{d1}$ comprises an optionally substituted $C_{1-6}$ aliphatic group. In certain embodiments, methods of the present invention comprise treating heterocycles where $R^{a1}$, $R^{b1}$, and $R^{c1}$ are —H, and $R^{d1}$ is methyl. In certain embodiments, methods of the present invention comprise treating heterocycles where $R^{a1}$, $R^{b1}$, and $R^{c1}$ are —H, and $R^{d1}$ is —$CH_2Cl$. In certain embodiments, methods of the present invention comprise treating heterocycles where $R^{a1}$, $R^{b1}$, and $R^{c1}$ are —H, and $R^{d1}$ is —$CH_2OR^y$, —$CH_2OC(O)R^y$, where $R^y$ is as defined above. In certain embodiments, methods of the present invention comprise treating heterocycles where $R^{a1}$, $R^{b1}$, and $R^{c1}$ are —H, and $R^{d1}$ is —$CH_2CH(R^c)OH$, where $R^c$ is as defined above and in the classes and subclasses herein.

In certain embodiments, methods of the present invention comprise the step of contacting ethylene oxide with carbon monoxide in the presence of any of the catalysts defined hereinabove or described in the classes, subclasses and Tables herein. In certain embodiments, the method comprises treating the ethylene oxide with carbon monoxide in the presence of the catalyst until a substantial portion of the ethylene oxide has been converted to beta propiolactone. In certain embodiments, the method comprises treating the ethylene oxide with carbon monoxide in the presence of the catalyst until a substantial portion of the ethylene oxide has been converted to succinic anhydride.

In certain embodiments, methods of the present invention comprise the step of contacting propylene oxide with carbon monoxide in the presence of any of the catalysts defined hereinabove or described in the classes, subclasses and Tables herein. In certain embodiments, the method comprises treating the propylene oxide with carbon monoxide in the presence of the catalyst until a substantial portion of the propylene oxide has been converted to beta butyrolactone. In certain embodiments, the method comprises treating the ethylene oxide with carbon monoxide in the presence of the catalyst until a substantial portion of the propylene oxide has been converted to methyl succinic anhydride.

In another embodiment, the present invention encompasses methods of making copolymers of epoxides and CO by contacting an epoxide with CO in the presence of any of the catalysts defined hereinabove or described in the classes, subclasses and Tables herein. In certain embodiments, such processes conform to the scheme:

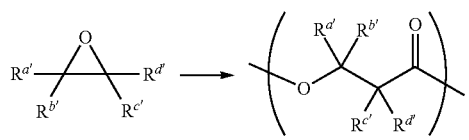

where each of $R^a$, $R^b$, $R^c$, and $R^d$, are as defined above.

In certain embodiments, methods of the present invention comprise the step of contacting ethyle oxide with carbon monoxide in the presence of any of the catalysts defined hereinabove or described in the classes, subclasses and Tables herein to provide polypropiolactone polymer.

In certain embodiments, methods of the present invention comprise the step of contacting ethyle oxide with carbon monoxide in the presence of any of the catalysts defined hereinabove or described in the classes, subclasses and Tables herein to provide poly-3-hydroxybutyrate polymer.

In other embodiments, the present invention includes methods for carbonylation of epoxides, aziridines, thiiranes, oxetanes, lactones, lactams and analogous compounds using the above-described catalysts. Suitable methods and reaction conditions for the carbonylation of such compounds are disclosed in Yutan et al. (*J. Am. Chem. Soc.* 2002, 124, 1174-1175), Mahadevan et al. (*Angew. Chem. Int. Ed.* 2002, 41, 2781-2784), Schmidt et al. (*Org. Lett.* 2004, 6, 373-376 and *J. Am. Chem. Soc.* 2005, 127, 11426-11435), Kramer et al. (*Org. Lett.* 2006, 8, 3709-3712 and *Tetrahedron* 2008, 64, 6973-6978) and Rowley et al. (*J. Am. Chem. Soc.* 2007, 129, 4948-4960, in U.S. Pat. No. 6,852,865 and in U.S. patent application Ser. No. 11/705,528, all of which are hereby incorporated herein in their entirety.

EXAMPLES

Example 1

A typical route to a salen aluminum (III) catalyst is shown in Scheme E1, below:

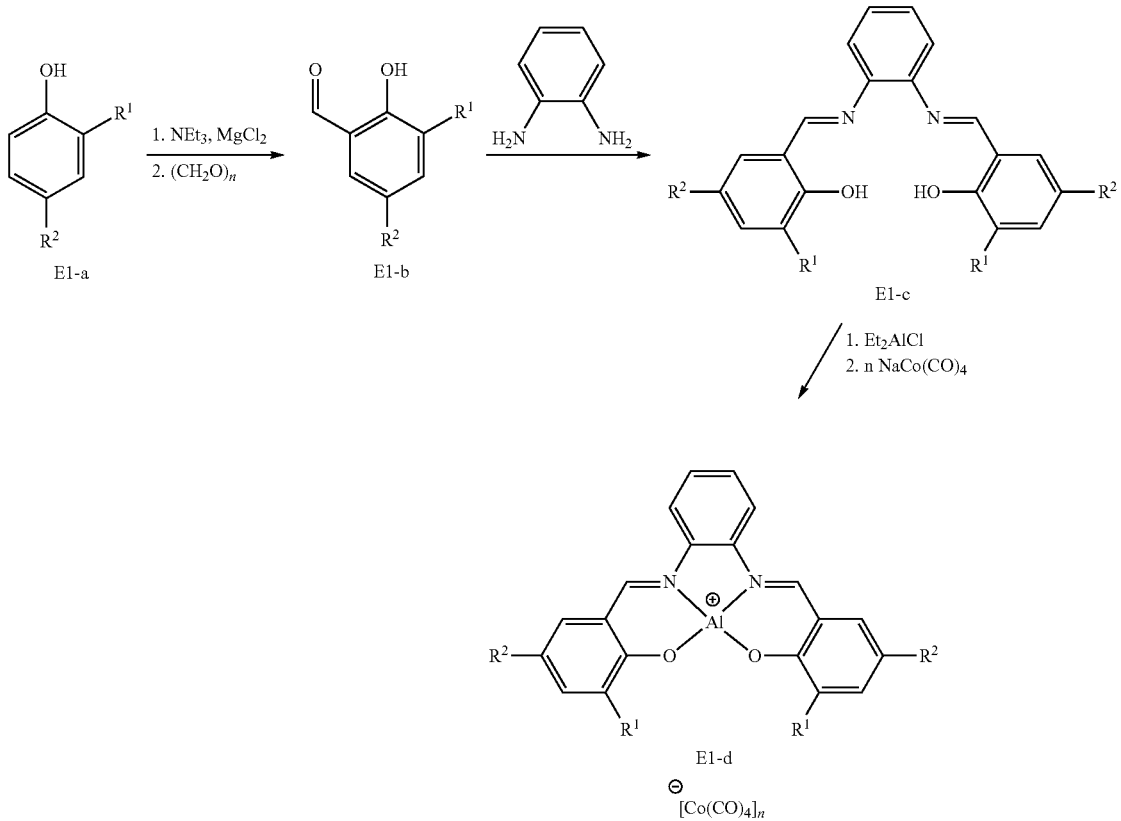

As shown in Scheme E1, disubstituted phenol E1-a is formylated to provide salicylaldehyde derivative E1-b. Two equivalents of this aldehyde are then reacted with a diamine (in this case 1,2-benzenediamine) to afford Schiff base E1-c. This compound is then reacted with diethyl aluminum chloride and sodium cobalt tetracarbonyl to give the active Al(III)-salen catalyst. Similar chemistries can be applied to synthesis of the catalysts described hereinabove. One skilled in the art of organic synthesis can adapt this chemistry as needed to provide the specific catalysts described herein, though in some cases routine experimentation to determine acceptable reaction conditions and functional group protection strategies may be required.

Example 2

Synthesis of [{tetrakis-(N-methyl-4-pyridinium)-porphyrin}Al(THF)$_2$][Co(CO)$_4$]$_5$ is shown in Scheme E2, below:

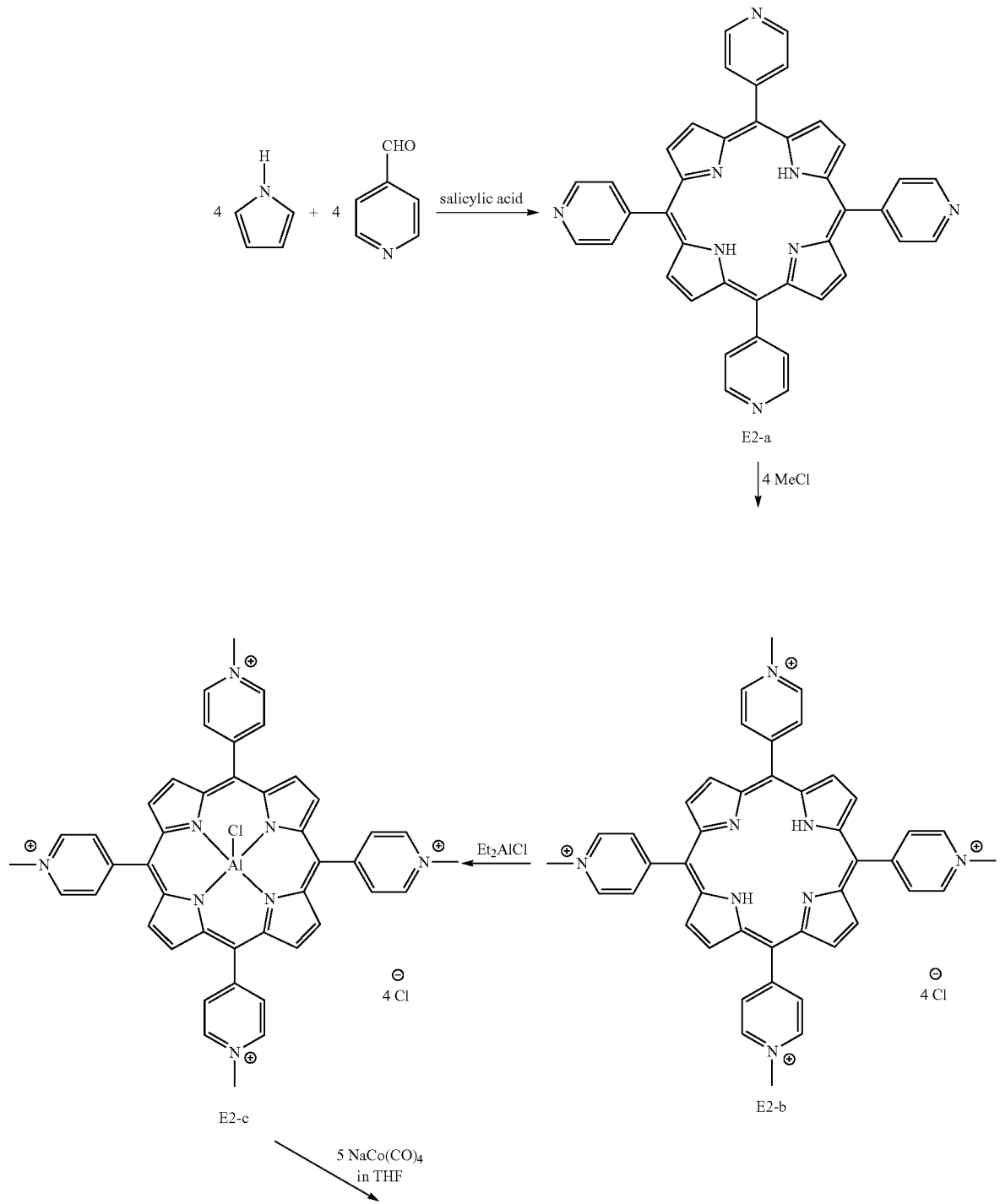

-continued

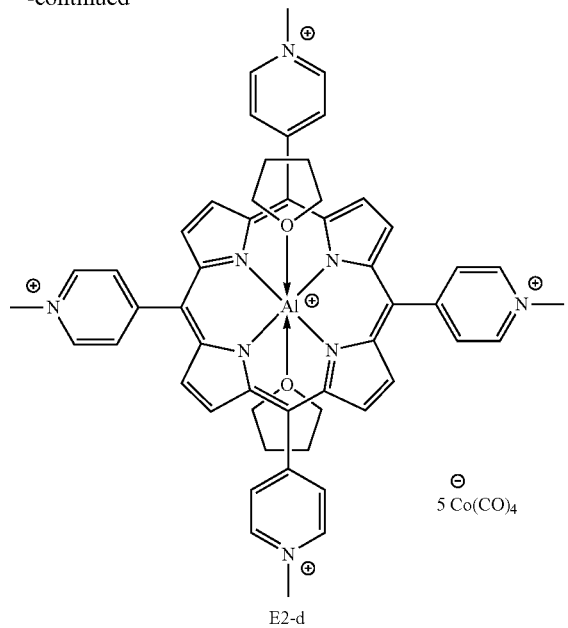

E2-d

As shown in Scheme E2, pyrrole, pyridine-4-carbaldehyde and salicylic acid are refluxed in xylene to give porphyrin E2-a. E2-a is further reacted with MeCl to afford E2-b. E2-b is reacted with diethyl aluminum chloride and then with five equivalents of NaCo(CO)$_4$ in THF to afford the active Al(III)-salen catalyst E2-d. One skilled in the art of organic synthesis can adapt this chemistry as needed to provide the specific catalysts described herein, though in some cases routine experimentation to determine acceptable reaction conditions and functional group protection strategies may be required.

This application refers to various issued patents, published patent applications journal articles, and other publications all of which are incorporated herein by reference.

Other Embodiments

The foregoing has been a description of certain non-limiting embodiments of the invention. Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A catalyst comprising:
   i) a metal complex of formula:

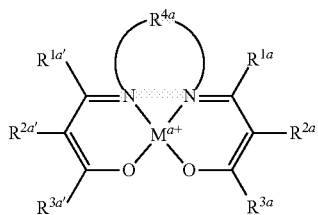

wherein:
M is a metal atom;
a is an integer from 1 to 4 inclusive;
at least on of $R^{1a}$, $R^{1a'}$, $R^{2a}$, $R^{2a'}$, $R^{3a}$, $R^{3a'}$, $R^c$, and $R^d$ is independently —∿∿— $(Z^+)_b$, wherein:
—∿∿— is a bond or a linker;
$Z^+$ comprises an atom selected from the group consisting of nitrogen, phosphorous, arsenic, and sulfur; and
b is an integer from 1 to 4 inclusive;
the remaining $R^{1a}$, $R^{1a'}$, $R^{2a}$, $R^{2a'}$, $R^{3a}$, $R^{3a'}$ at each occurrence are independently hydrogen, halogen, —OR$^4$, —NR$^y_2$, —CN, —NO$_2$, —SO$_2$R$^y$, —SO$_2$NR$^y_2$, —CNO, —NCO, or —N$_3$; or an optionally substituted group selected from the group consisting of:
C$_{1-20}$ aliphatic;
C$_{1-20}$ heteroaliphatic having 1-4 heteroatoms independently selected from the group consisting of nitrogen, oxygen, and sulfur;
6- to 10-membered aryl;
5- to 10-membered heteroaryl having 1-4 heteroatoms independently selected from nitrogen, oxygen, or sulfur; and
4- to 7-membered heterocyclic having 1-2 heteroatoms independently selected from the group consisting of nitrogen, oxygen, and sulfur;
wherein:
R$^4$ at each occurrence is a hydroxyl protecting group or R$^y$;
R$^y$ at each occurrence is independently hydrogen, or an optionally substituted group selected from the group consisting of:
acyl;
carbamoyl;
arylalkyl;
6- to 10-membered aryl;
C$_{1-12}$ aliphatic;
C$_{1-12}$ heteroaliphatic having 1-2 heteroatoms independently selected from the group consisting of nitrogen, oxygen, and sulfur;

5- to 10-membered heteroaryl having 1-4 heteroatoms independently selected from the group consisting of nitrogen, oxygen, and sulfur;
4- to 7-membered heterocyclic having 1-2 heteroatoms independently selected from the group consisting of nitrogen, oxygen, and sulfur;
an oxygen protecting group; and
a nitrogen protecting group; or
wherein two $R^y$ on the same nitrogen atom are taken with the nitrogen atom to form an optionally substituted 4- to 7-membered heterocyclic ring having 0-2 additional heteroatoms independently selected from the group consisting of nitrogen, oxygen, and sulfur;
wherein any of ($R^{2a'}$ and $R^{3a'}$), ($R^{2a}$ and $R^{3a}$), ($R^{1a}$ and $R^{2a}$), and ($R^{1a'}$ and $R^{2a'}$) may optionally be taken together with the carbon atoms to; which they are attached to form one or more rings:
$R^{4a}$ is selected from the group consisting of

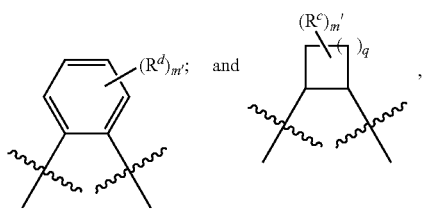

wherein:
$R^d$ at each occurrence is independently ⎯⎯⎯$(Z^+)_b$, hydrogen, halogen, —$OR^4$, —$NR^y_2$, —CN, —$NO_2$, —$SO_2R^y$, —$SOR^y$, —$SO_2NR^y_2$, —CNO, —NCO, or —$N_3$; or an optionally substituted group selected from the group consisting of:
$C_{1-20}$ aliphatic;
$C_{1-20}$ heteroaliphatic having 1-4 heteroatoms independently selected from the group consisting of nitrogen, oxygen, and sulfur;
6- to 10-membered aryl;
5- to 10-membered heteroaryl having 1-4 heteroatoms independently selected from the group consisting of nitrogen, oxygen, and sulfur; and
4- to 7-membered heterocyclic having 1-2 heteroatoms independently selected from the group consisting of nitrogen, oxygen, and sulfur, or
wherein two or more $R^d$ groups are taken together to form one or more optionally substituted rings;
$R^c$ at each occurrence is independently ⎯⎯⎯$(Z^+)_b$, hydrogen, halogen, —$NR^y_2$, —$SR_y$, —CN, —$NO_2$,—$SO_2R^y$, —$SOR^y$, —$SO_2NR^y_2$, —CNO, —NCO, or —$N_3$; or an optionally substituted group selected from the group consisting of:
$C_{1-20}$ aliphatic;
$C_{1-20}$ heteroaliphatic having 1-4 heteroatoms independently selected from the group consisting of nitrogen, oxygen, and sulfur;
6- to 10-membered aryl;
5- to 10-membered heteroaryl having 1-4 heteroatoms independently selected from nitrogen, oxygen, or sulfur; and
4- to 7-membered heterocyclic having 1-2 heteroatoms independently selected from the group consisting of nitrogen, oxygen, and sulfur; or
wherein two or more $R^c$ groups are taken together with the carbon atoms to which they are attached and any intervening atoms to form one or more rings; or wherein two $R^c$ groups are attached to the same carbon atom, and are taken together along with the carbon atom to which they are attached to form a moiety selected from the group consisting of:
a 3- to 8-membered spirocyclic ring;
a carbonyl;
an oxime;
a hydrazine; and
an imine:
m' is 0 or an integer from 1 to 4, inclusive; and
q is 0 or an integer from 1 to 4, inclusive; and
ii) at least one anionic metal carbonyl species associated with at least one of $Z^+$.

2. The catalyst of claim 1, wherein M is selected from the group consisting of Zn(II), Cu(II), Mn(II), Co(II), Ru(II), Fe(II), Co(II), Rh(II), Ni(II), Pd(II), Mg(II), Al(III), Cr(III), Cr(IV), Ti(IV), Fe(III), Co(III), Ti(III), In(III), Ga(III), and Mn(III).

3. The catalyst of claim 1, wherein M is aluminum.

4. The catalyst of claim 1, wherein M is chromium.

5. The catalyst of claim 1, wherein at least one anionic metal carbonyl species is X−, and X− is associated with at least on $Z^+$, wherein $Z^+X^-$ is selected from the group consisting of:

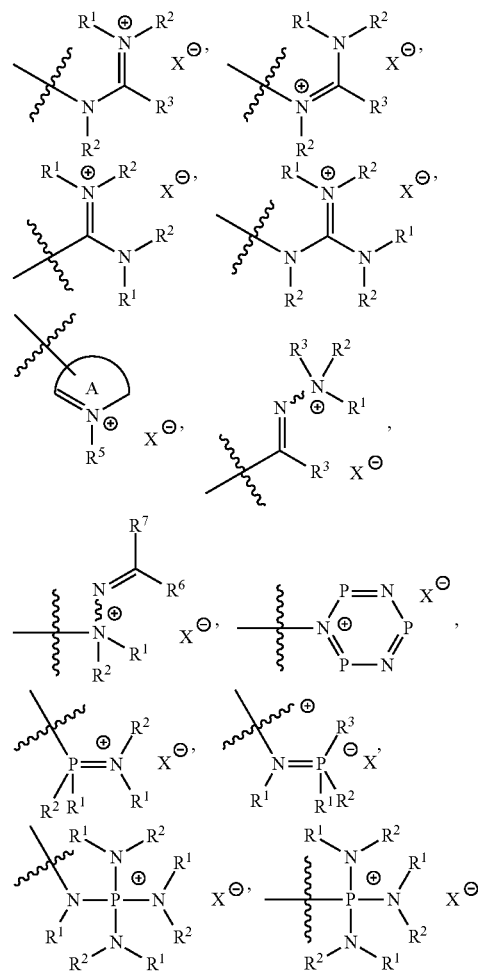

-continued

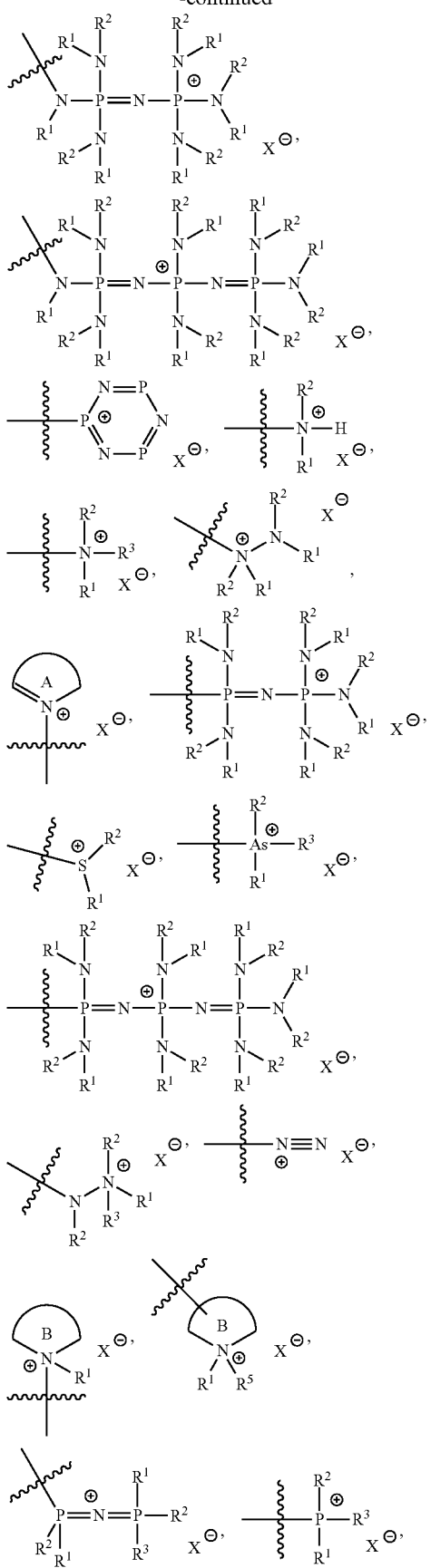

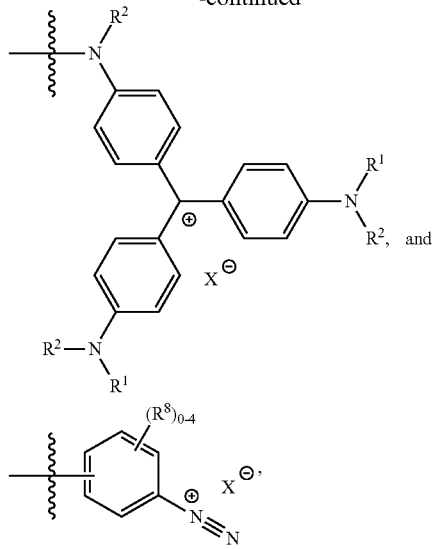

or a combination of two or more of these, wherein:
each R¹ and R² is independently hydrogen or an optionally substituted group selected from the group consisting of:
  $C_{1-20}$ aliphatic;
  $C_{1-20}$ heteroaliphatic;
  a 3- to 8-membered saturated or partially unsaturated monocyclic carbocycle;
  a 7- to 14-membered saturated or partially unsaturated polycyclic carbocycle;
  a 5- to 6-membered monocyclic heteroaryl ring having 1-4 heteroatoms independently selected from the group consisting of nitrogen, oxygen, and sulfur;
  an 8- to 14-membered polycyclic heteroaryl ring having 1-5 heteroatoms independently selected from the group consisting of nitrogen, oxygen, and sulfur;
  a 3- to 8-membered saturated or partially unsaturated monocyclic heterocyclic ring having 1-3 heteroatoms independently selected from the group consisting of nitrogen, oxygen, and sulfur;
  a 6- to 14-membered saturated or partially unsaturated polycyclic heterocycle having 1-5 heteroatoms independently selected from the group consisting of nitrogen, oxygen, and sulfur; phenyl; and
  an 8- to 14-membered polycyclic aryl ring; or
  wherein R¹ and R² are taken together with intervening atoms to form one or more optionally substituted rings optionally containing one or more additional heteroatoms;
each R³ is independently hydrogen or an optionally substituted group selected from the group consisting of:
  $C_{1-20}$ aliphatic;
  $C_{1-20}$ heteroaliphatic;
  a 3- to 8-membered saturated or partially unsaturated monocyclic carbocycle;
  a 7- to 14-membered saturated or partially unsaturated polycyclic carbocycle;
  a 5- to 6-membered monocyclic heteroaryl ring having 1-4 heteroatoms independently selected from the group consisting of nitrogen, oxygen, and sulfur;
  an 8- to 14-membered polycyclic heteroaryl ring having 1-5 heteroatoms independently selected from the group consisting of nitrogen, oxygen, and sulfur;

a 3- to 8-membered saturated or partially unsaturated monocyclic heterocyclic ring having 1-3 heteroatoms independently selected from the group consisting of nitrogen, oxygen, and sulfur;
a 6- to 14-membered saturated or partially unsaturated polycyclic heterocycle having 1-5 heteroatoms independently selected from the group consisting of nitrogen, oxygen, and sulfur; phenyl; and
an 8- to 14-membered polycyclic aryl ring; or
wherein an $R^3$ group are taken with an $R^1$ or $R^2$ group to form one or more optionally substituted rings; and
$R^5$ is $R^2$ or hydroxyl; or wherein $R^1$ and $R^5$ are taken together with intervening atoms to form one or more optionally substituted carbocyclic, heterocyclic, aryl, or heteroaryl rings;
each $R^6$ and $R^7$ is independently hydrogen or an optionally substituted group selected from the group consisting of:
$C_{1-20}$ aliphatic;
$C_{1-20}$ heteroaliphatic;
a 3- to 8-membered saturated or partially unsaturated monocyclic carbocycle;
a 7- to 14-membered saturated or partially unsaturated polycyclic carbocycle;
a 5- to 6-membered monocyclic heteroaryl ring having 1-4 heteroatoms independently selected from the group consisting of nitrogen, oxygen, and sulfur;
an 8- to 14-membered polycyclic heteroaryl ring having 1-5 heteroatoms independently selected from the group consisting of nitrogen, oxygen, and sulfur;
a 3- to 8-membered saturated or partially unsaturated monocyclic heterocyclic ring having 1-3 heteroatoms independently selected from the group consisting of nitrogen, oxygen, and sulfur;
a 6- to 14-membered saturated or partially unsaturated polycyclic heterocycle having 1-5 heteroatoms independently selected from the group consisting of nitrogen, oxygen, and sulfur; phenyl; and
an 8- to 14-membered polycyclic aryl ring; or
wherein $R^6$ and $R^7$ are taken together with intervening atoms to form one or more optionally substituted rings optionally containing one or more heteroatoms, or an $R^6$ and $R^7$ group are taken with an $R^1$ or $R^2$ group to form one or more optionally substituted rings;
each occurrence of $R^8$ is independently:
halogen, $-NO_2$, $-CN$, $-SR^y$, $-S(O)R^y$, $-S(O)_2R^y$, $-NR^yC(O)R^y$, $-OC(O)R^y$, $-CO_2R^y$, $-NCO$, $-N_3$, $-OR^y$, $-OC(O)N(R^y)_2$, $-N(R^y)_2$, $-NR^yC(O)R^y$, or $-NR^yC(O)OR^y$; or an optionally substituted group selected from the group consisting of:
$C_{1-20}$ aliphatic;
$C_{1-20}$ heteroaliphatic;
a 3- to 8-membered saturated or partially unsaturated monocyclic carbocycle;
a 7- to 14-membered saturated or partially unsaturated polycyclic carbocycle;
a 5- to 6-membered monocyclic heteroaryl ring having 1-4 heteroatoms independently selected from the group consisting of nitrogen, oxygen, and sulfur;
an 8- to 14-membered polycyclic heteroaryl ring having 1-5 heteroatoms independently selected from the group consisting of nitrogen, oxygen, and sulfur;
a 3- to 8-membered saturated or partially unsaturated monocyclic heterocyclic ring having 1-3 heteroatoms independently selected from the group consisting of nitrogen, oxygen, and sulfur;
a 6- to 14-membered saturated or partially unsaturated polycyclic heterocycle having 1-5 heteroatoms independently selected from the group consisting of nitrogen, oxygen, and sulfur; phenyl; and
an 8- to 14-membered polycyclic aryl ring;
wherein each $R^y$ is independently $-H$, or an optionally substituted group selected from the group consisting of $C_{1-6}$ aliphatic, phenyl, a 3-7 membered saturated or partially unsaturated carbocyclic ring, a 3-7 membered saturated or partially unsaturated monocyclic heterocyclic ring having 1-2 heteroatoms independently selected from the group consisting of nitrogen, oxygen, and sulfur, a 5-6 membered heteroaryl ring having 1-3 heteroatoms independently selected from the group consisting of nitrogen, oxygen, and sulfur, and an 8- to 10- membered aryl; or
wherein two or more adjacent $R^8$ groups are taken together to form an optionally substituted saturated, partially unsaturated, or aromatic 5- to 12-membered ring containing 0 to 4 heteroatoms;
Ring A is an optionally substituted, 5- to 10-membered heteroaryl group; and
Ring B is an optionally substituted, 3- to 8-membered saturated or partially unsaturated monocyclic heterocyclic ring having 0-2 heteroatoms in addition to the depicted ring nitrogen atom independently selected from the group consisting of nitrogen, oxygen, and sulfur;
wherein:
when ⎯⎯⎯ is a bond,

is the site of attachment of $Z^+$ to the metal complex;
when ⎯⎯⎯ is a linker,

is the site of attachment of $Z^+$ to the linker.
6. The catalyst of claim 5, wherein $Z^+X^-$ is selected from the group consisting of:

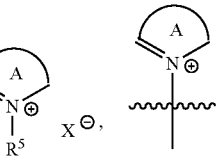

-continued

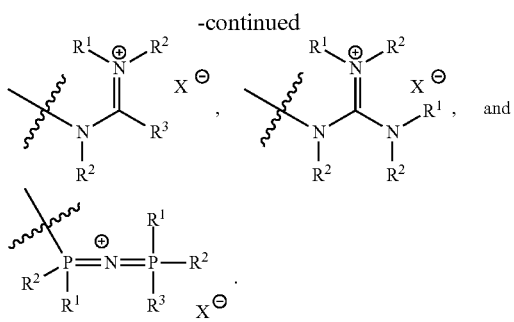

7. The catalyst of claim 6, wherein $Z^+X^-$ is selected from the group consisting of:

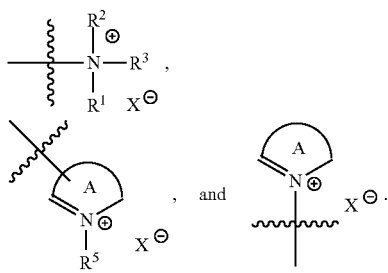

8. The catalyst of claim 6, wherein $Z^+X^-$ is selected from the group consisting of:

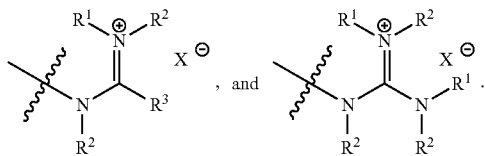

9. The catalyst of claim 6, wherein $Z^+X^-$ is selected from the group consisting of:

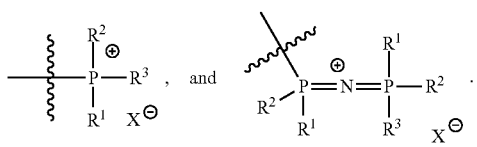

10. The catalyst of claim 1, wherein the linker comprises 1-30 atoms including at least one carbon atom and optionally one or more atoms selected from the group consisting of N, O, S, Si, B, and P.

11. The catalyst of claim 10, wherein the linker is an optionally substituted $C_{2-30}$ aliphatic group wherein one or more methylene units are optionally and independently replaced by:
—Cy-, —NR$^y$—, —N(R$^y$)C(O)—, —C(O)N(R$^y$)—, —O—, —C(O)—, —OC(O)—, —C(O)O—, —S—, —SO—, —SO$_2$—, —C(=S)—, —C(=NR$^y$)—, or —N=N—,
wherein each —Cy- is independently an optionally substituted 5-8 membered bivalent, saturated, partially unsaturated, or aryl ring having 0-4 heteroatoms independently selected from the group consisting of nitrogen, oxygen, and sulfur; or an optionally substituted 8-10 membered bivalent saturated, partially unsaturated, or aryl bicyclic ring having 0-5 heteroatoms independently selected from the group consisting of nitrogen, oxygen, and sulfur; and each R$^y$ is independently —H, or an optionally substituted group selected from the group consisting of:
$C_{1-6}$ aliphatic,
phenyl,
a 3-7 membered saturated or partially unsaturated carbocyclic ring,
a 3-7 membered saturated or partially unsaturated monocyclic heterocyclic ring having 1-2 heteroatoms independently selected from the group consisting of nitrogen, oxygen, and sulfur,
a 5-6 membered heteroaryl ring having 1-3 heteroatoms independently selected from the group consisting of nitrogen, oxygen, and sulfur, and an
8- to 10- membered aryl.

12. The catalyst of claim 1, wherein the at least one anionic metal carbonyl species is a compound of formula: $[Q_dM'_e(CO)_w]^{y-}$, wherein:
Q is a ligand and need not be present,
M' is a metal atom,
d is an integer between 0 and 8 inclusive,
e is an integer between 1 and 6 inclusive,
w is a number such as to provide a stable anionic metal carbonyl complex, and
y is the charge of the anionic metal carbonyl species.

13. The catalyst of claim 12, wherein the at least one anionic metal carbonyl species is selected from the group consisting of: monoanionic carbonyl complexes of metals from groups 5, 7 or 9 of the periodic table, and dianionic carbonyl complexes of metals from groups 4 or 8 of the periodic table.

14. The catalyst of claim 12, wherein the at least one anionic metal carbonyl species is selected from the group consisting of: $[Co(CO)_4]^-$, $[Ti(CO)_6]^{2-}$, $[V(CO)_6]^-$, $[Rh(CO)_4]^-$, $[Fe(CO)_4]^{2-}$, $[Ru(CO)_4]^{2-}$, $[Os(CO)_4]^{2-}$, $[Cr_2(CO)_{10}]^{2-}$, $[Fe_2(CO)_8]^{2-}$, $[Tc(CO)_5]^-$, $[Re(CO)_5]^-$, and $[Mn(CO)_5]^-$.

15. The catalyst of claim 1, wherein the at least one anionic metal carbonyl species is $[Co(CO)_4]^-$.

16. The catalyst of claim 1, wherein the metal complex has a structure selected from the group consisting of:

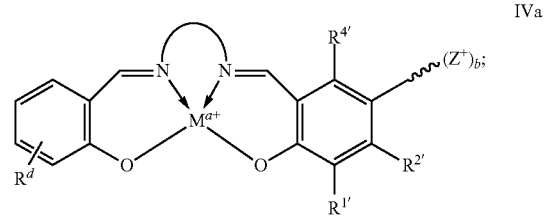

IVa

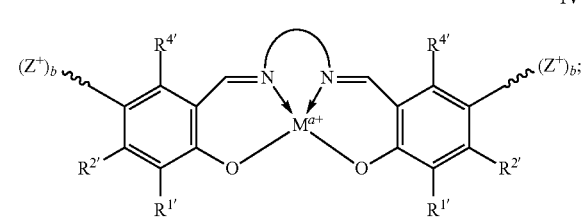

IVb

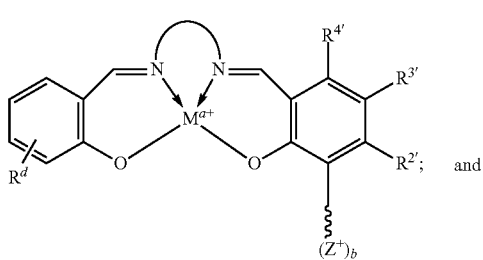

IIIa

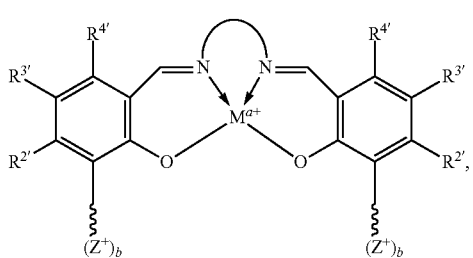

IIIb wherein:

⌒ is selected from the group consisting of

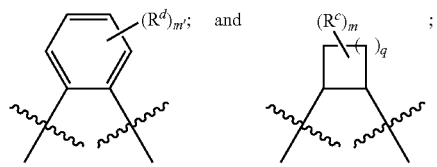

wherein q is 3; and $R^{1'}$, $R^{2'}$, $R^{3'}$, and $R^{4'}$ are independently at each occurrence: hydrogen, halogen, —$NO_2$, —CN, —$SR^y$, —S(O)$R^y$, —S(O)$_2R^y$, —$NR^yC(O)R^y$, —OC(O)$R^y$, —$CO_2R^y$, —NCO, —$N_3$, —$OR^4$, —OC(O)N($R^y$)$_2$, —N($R^y$)$_2$, —$NR^yC(O)R^y$, or —$NR^yC(O)OR^y$; or an optionally substituted group selected from the group consisting of:

$C_{1-20}$ aliphatic;

$C_{1-20}$ heteroaliphatic having 1-4 heteroatoms independently selected from the group consisting of nitrogen, oxygen, and sulfur;

6- to 10-membered aryl;

5- to 10-membered heteroaryl having 1-4 heteroatoms independently selected from the group consisting of nitrogen, oxygen, and sulfur; and 4- to 7-membered heterocyclic having 1-2 heteroatoms independently selected from the group consisting of nitrogen, oxygen, and sulfur, or wherein two or more adjacent $R^{1'}$, $R^{2'}$, $R^{3'}$, and $R^{4'}$ groups are taken together to form an optionally substituted saturated, partially unsaturated, or aromatic 5- to 12-membered ring containing 0 to 4 heteroatoms.

17. A catalyst comprising a compound selected from the group consisting of:

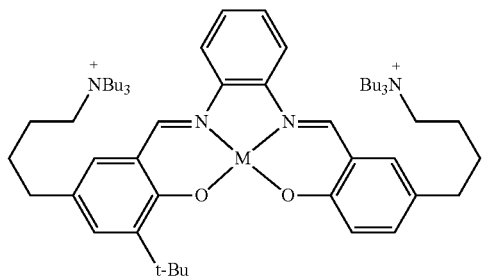

2 Co(CO)$_4^-$

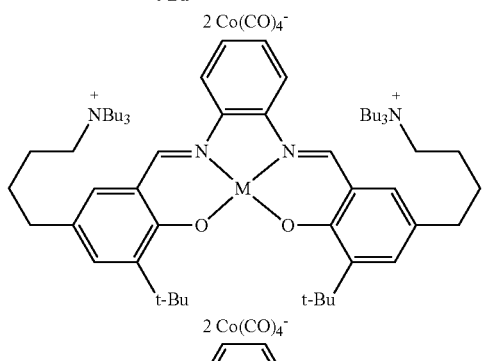

2 Co(CO)$_4^-$

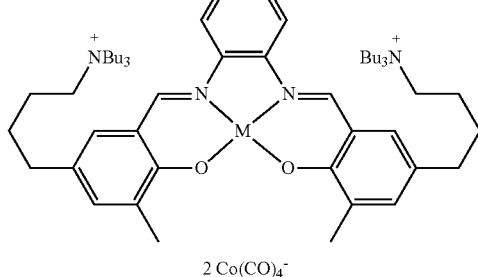

2 Co(CO)$_4^-$

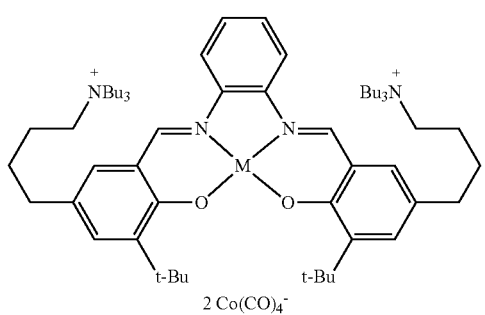

2 Co(CO)$_4^-$

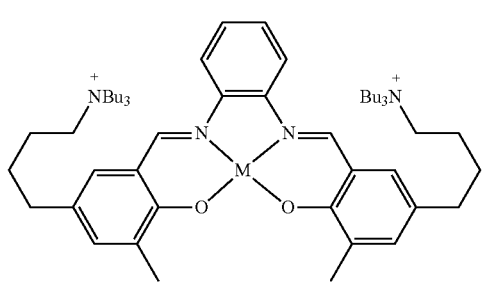

2 Co(CO)$_4^-$

177
-continued
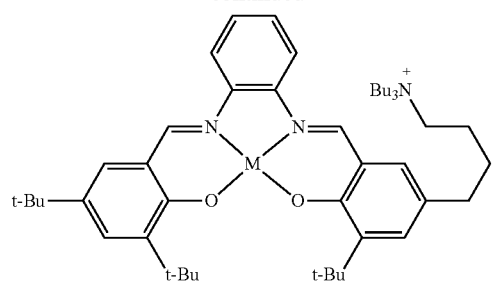
Co(CO)$_4^-$
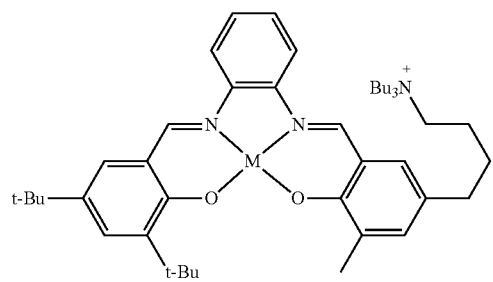
Co(CO)$_4^-$
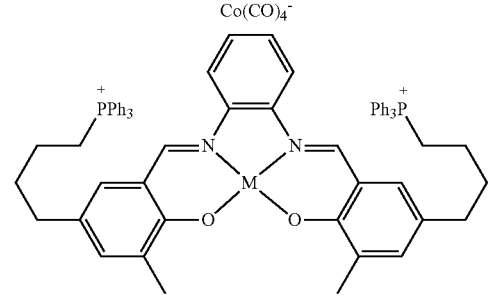
2 Co(CO)$_4^-$
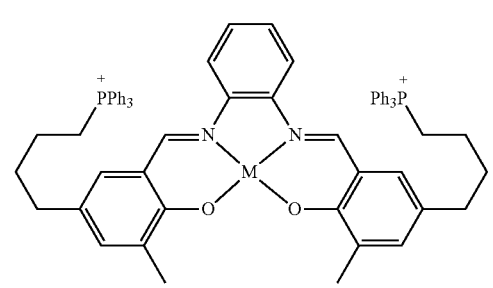
2 Co(CO)$_4^-$
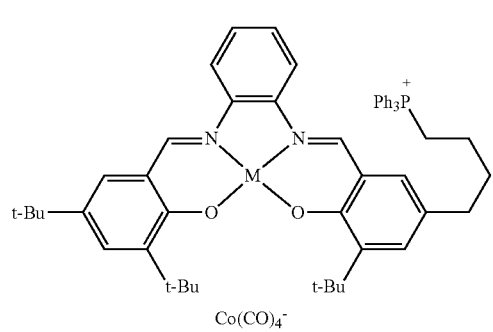
Co(CO)$_4^-$
178
-continued
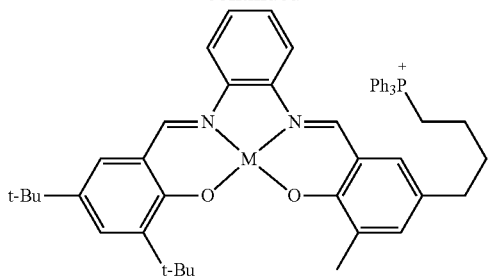
Co(CO)$_4^-$
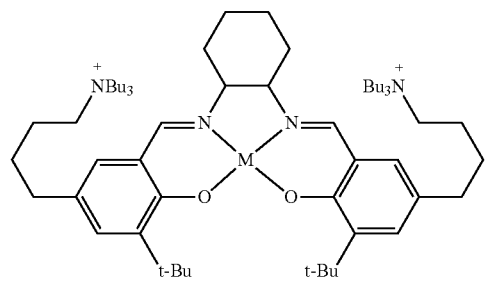
2 Co(CO)$_4^-$
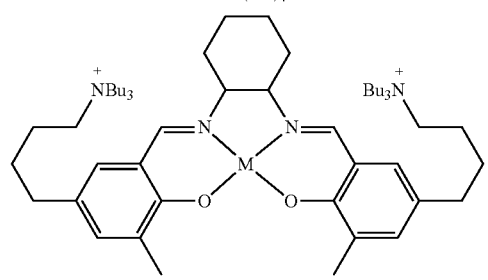
2 Co(CO)$_4^-$
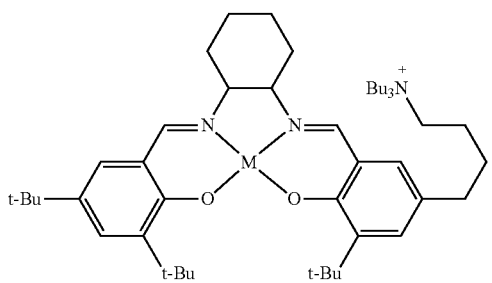
Co(CO)$_4^-$
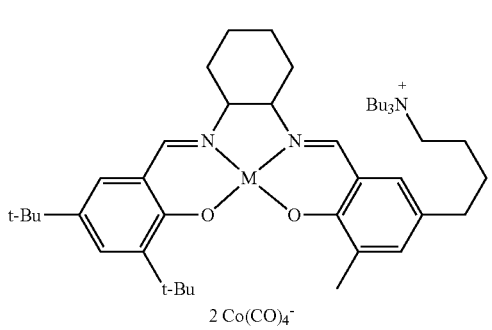
2 Co(CO)$_4^-$ -continued
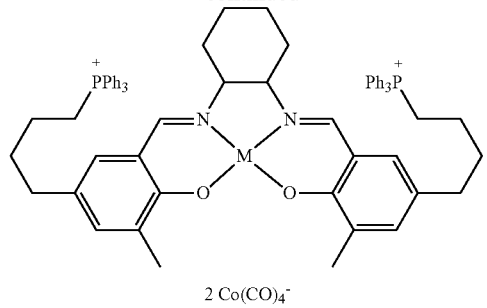
2 Co(CO)₄⁻
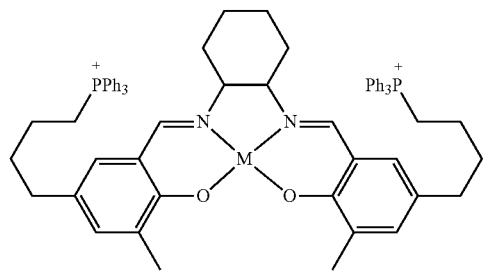
2 Co(CO)₄⁻
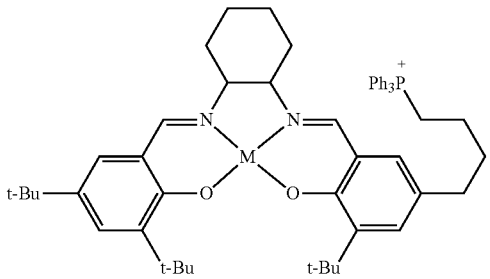
Co(CO)₄⁻
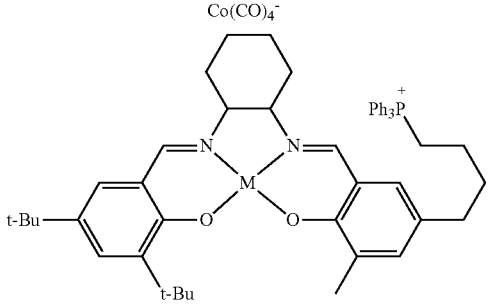
Co(CO)₄⁻
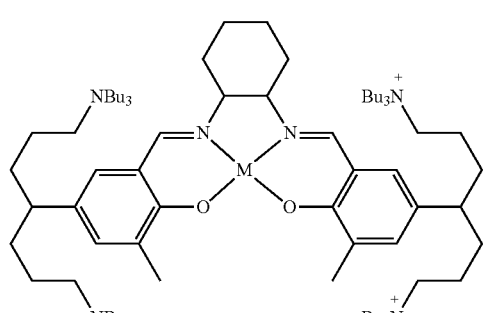
4 Co(CO)₄⁻
-continued
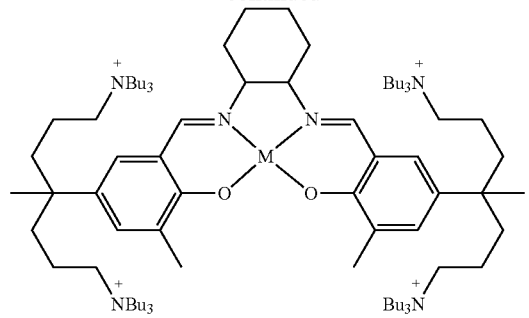
4 Co(CO)₄⁻
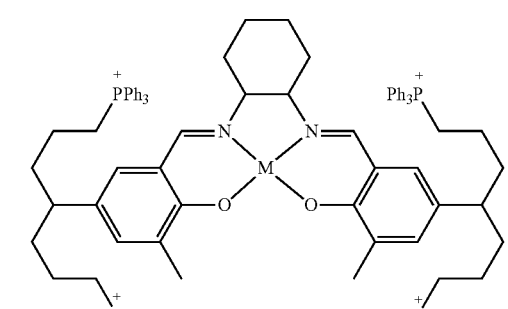
4 Co(CO)₄⁻
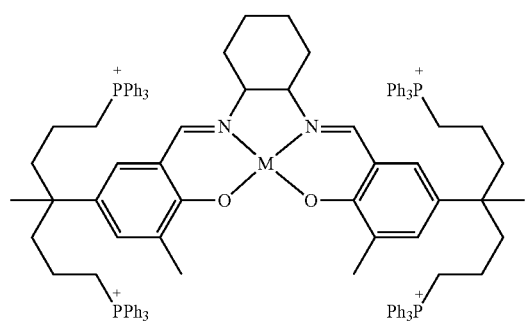
4 Co(CO)₄⁻
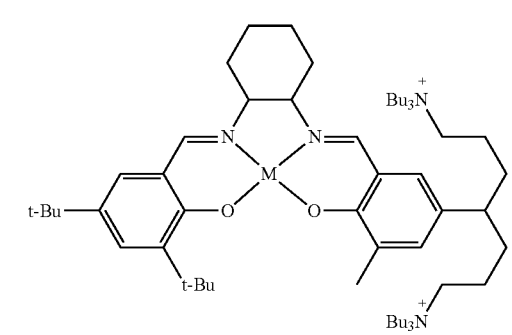
2 Co(CO)₄⁻

-continued
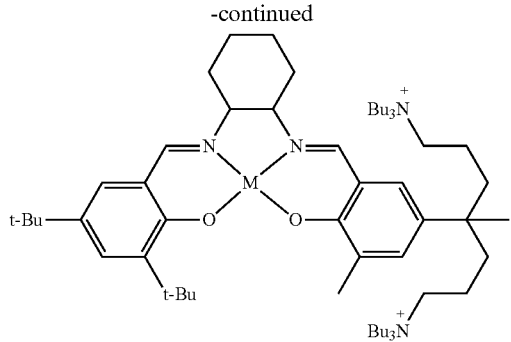
2 Co(CO)$_4^-$
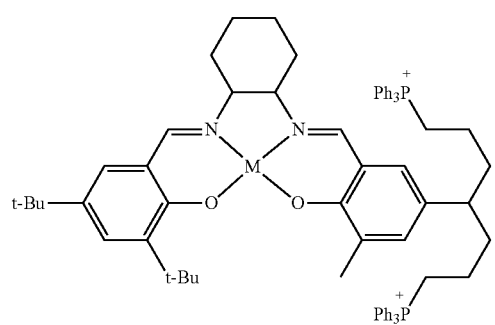
2 Co(CO)$_4^-$
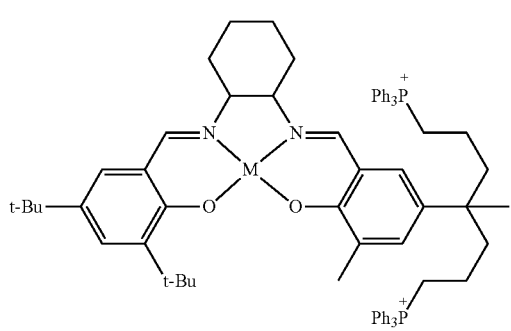
2 Co(CO)$_4^-$
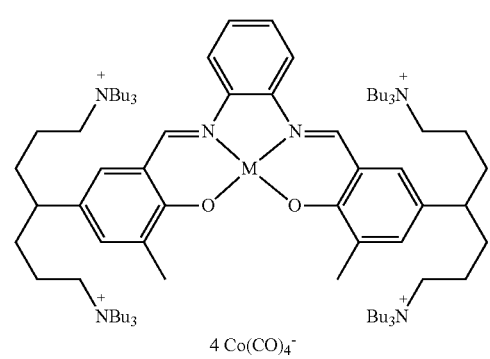
4 Co(CO)$_4^-$
-continued
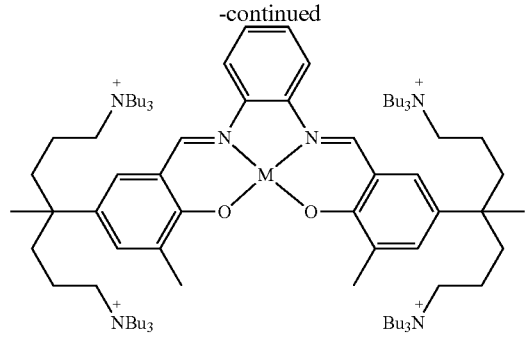
4 Co(CO)$_4^-$
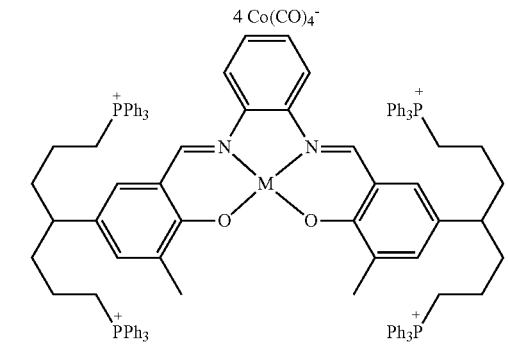
4 Co(CO)$_4^-$
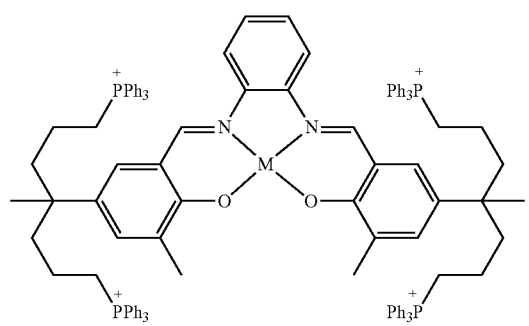
4 Co(CO)$_4^-$
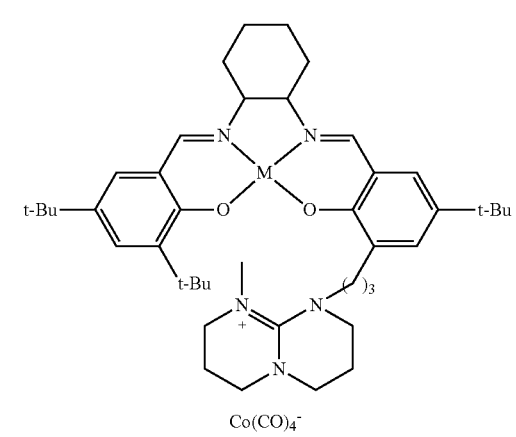
Co(CO)$_4^-$ 183
-continued
184
-continued
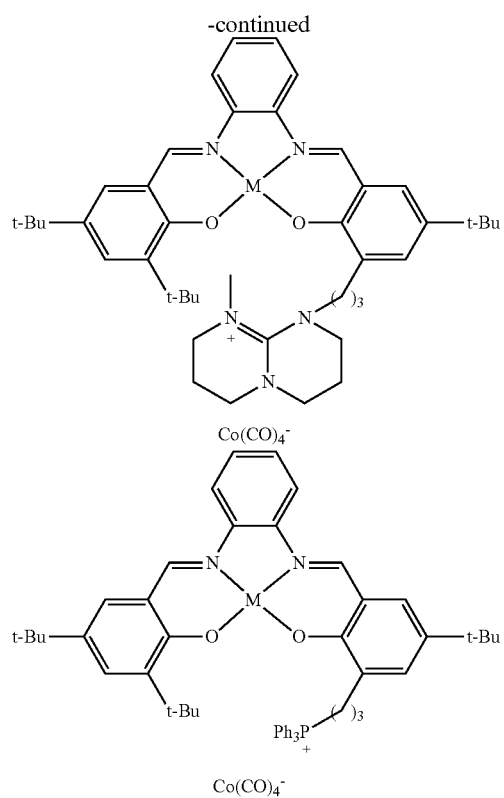
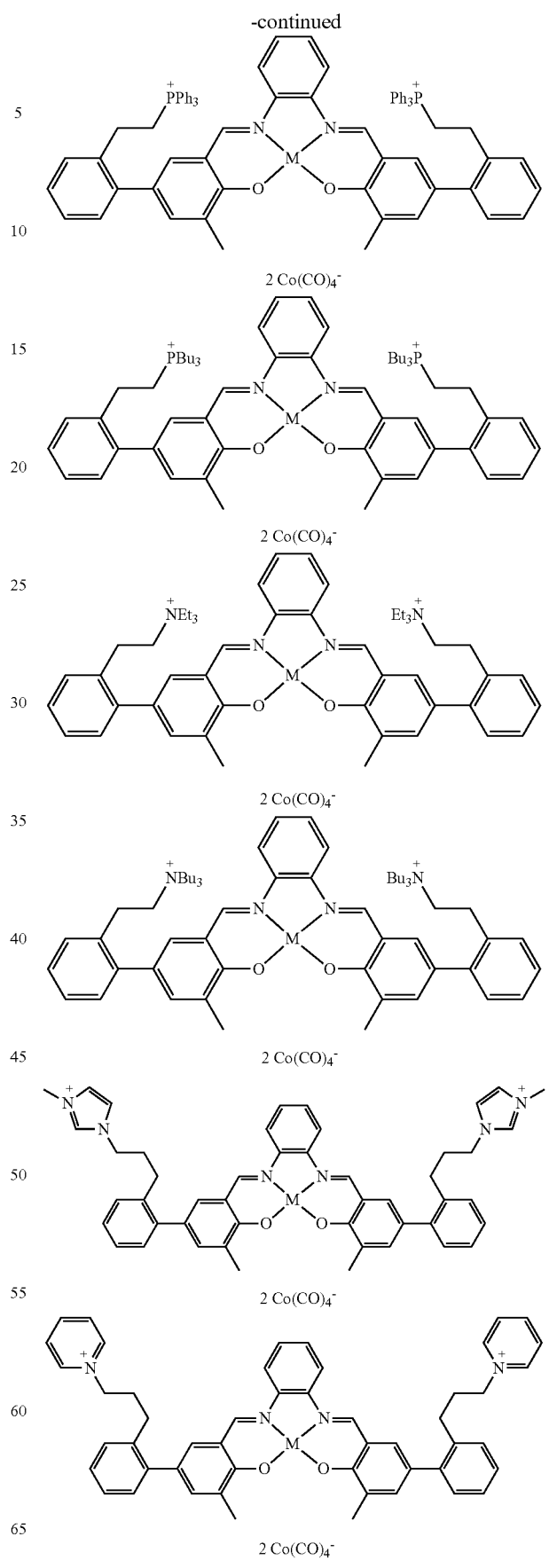

185
-continued

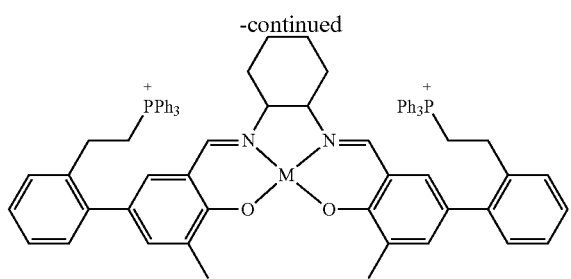

2 Co(CO)$_4^-$

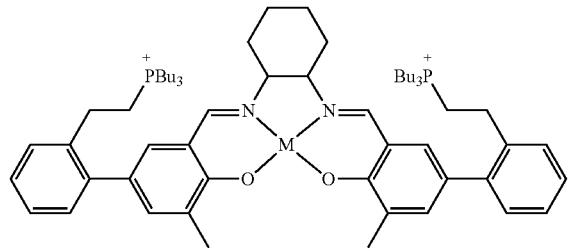

2 Co(CO)$_4^-$

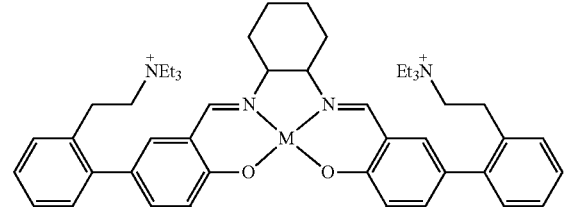

2 Co(CO)$_4^-$

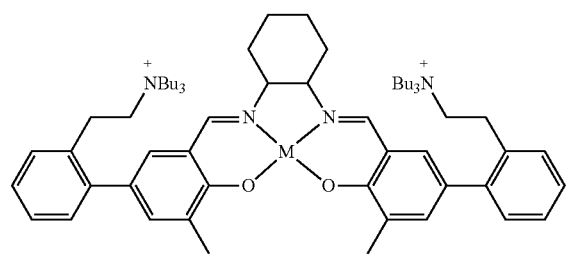

2 Co(CO)$_4^-$

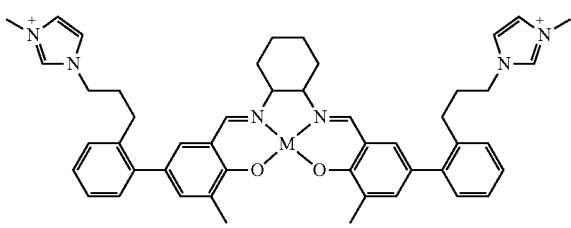

2 Co(CO)$_4^-$
and

186
-continued

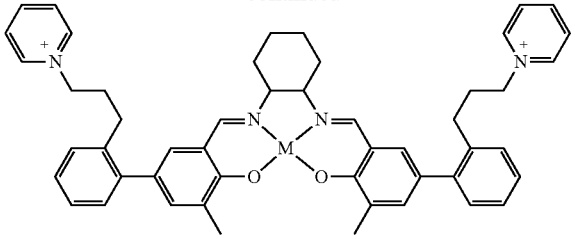

2 Co(CO)$_4^-$ wherein M is aluminum or chromium.

18. A method comprising contacting ethylene oxide with carbon monoxide in the presence of a catalyst of claim 1, to provide a product comprising beta propiolactone, succinic anhydride, or polypropiolactone, or a mixture of any two or more of these.

19. The method of claim 18, wherein the product comprises beta propiolactone.

20. The method claim 18, wherein the product comprises polypropiolactone.

21. The catalyst of claim 1, wherein the linker is selected from the group consisting of:

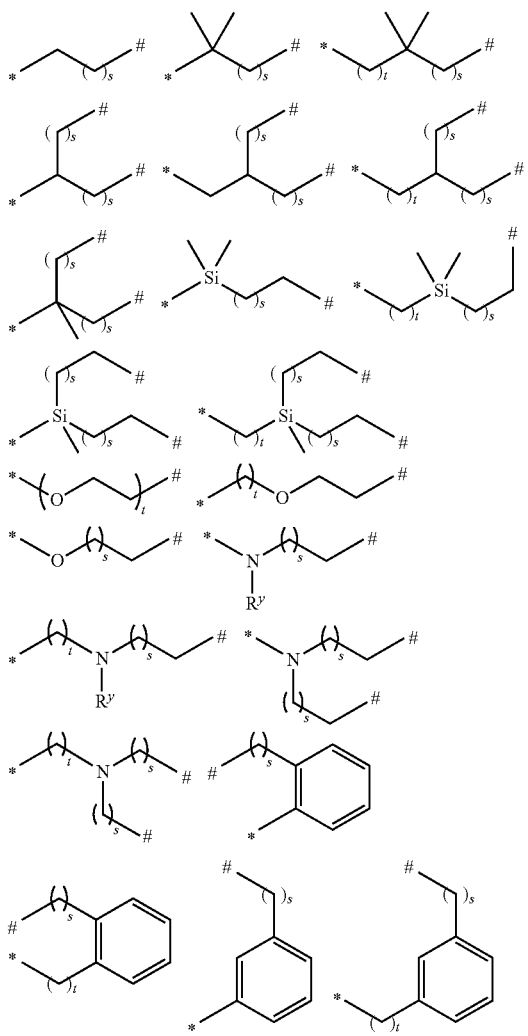

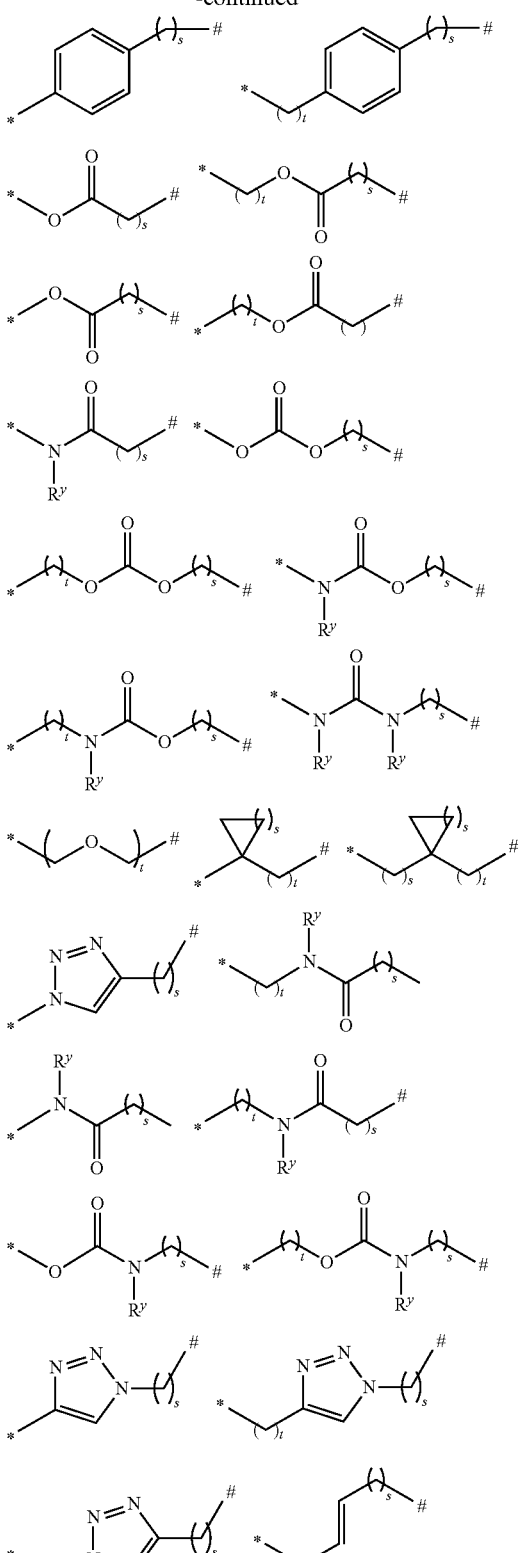

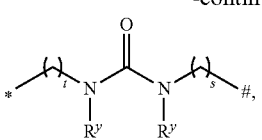

wherein each s is independently 0-6, t is 0-4, each * represents the site of attachment to the metal complex, and each # represents a site of attachment of $Z^+$.

22. The catalyst of claim 1, wherein the metal complex has a structure selected from the group consisting of:

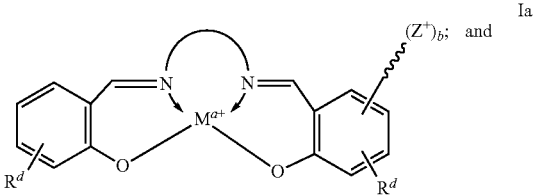

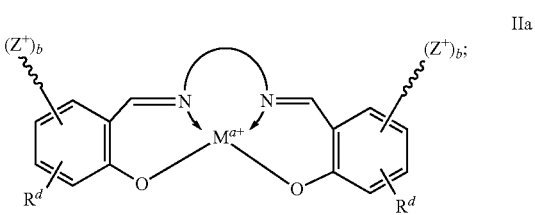

wherein:

⌒ is selected from the group consisting of

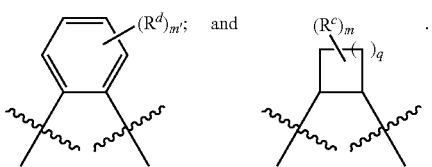

23. The catalyst of claim 1, wherein the metal complex has a structure selected from the group consisting of:

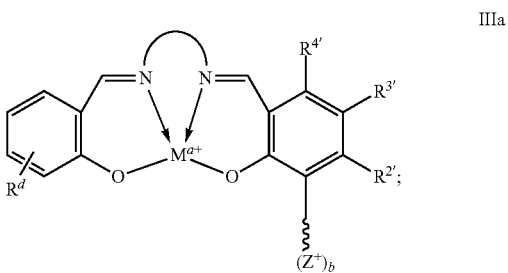

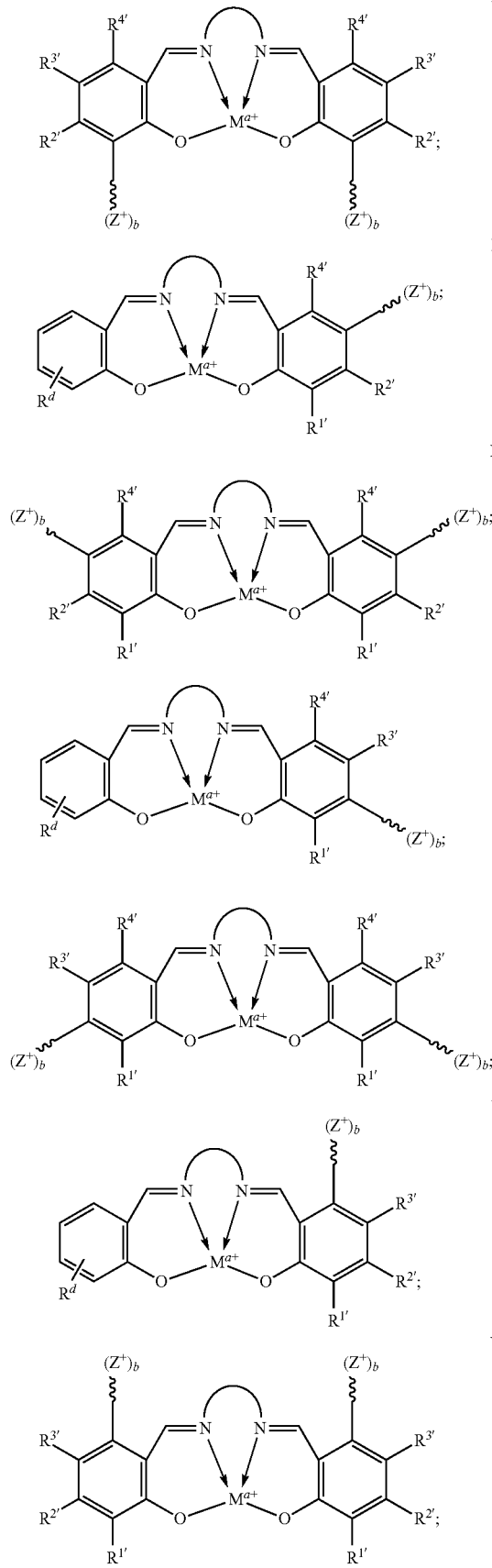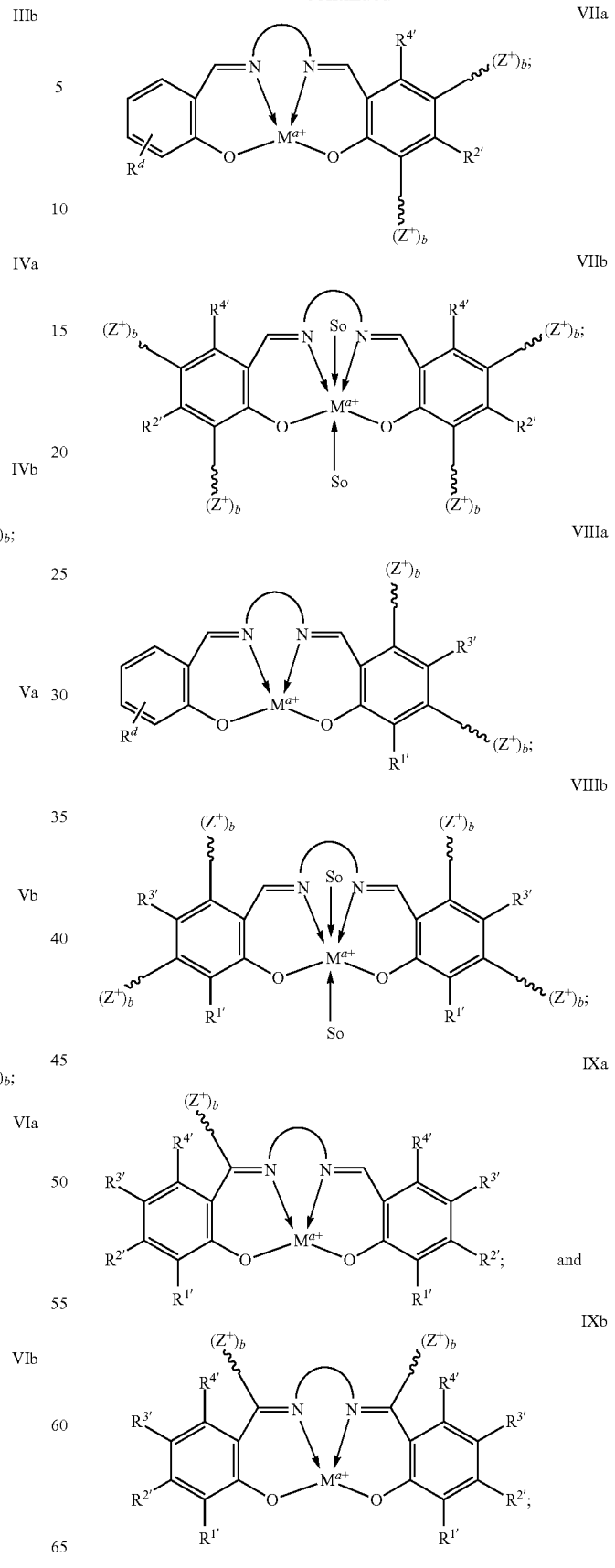

wherein:

⌒ is selected from the group consisting of

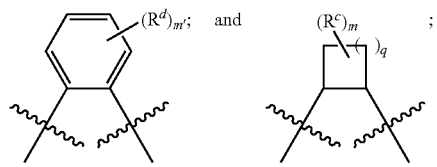

R$^{1'}$, R$^{2'}$, R$^{3'}$, and R$^{4'}$ are independently at each occurrence: hydrogen, halogen, —NO$_2$, —CN, —SR$^y$, —S(O)R$^y$, —S(O)$_2$R$^y$, —NR$^y$C(O)R$^y$, —OC(O)R$^y$, —CO$_2$R$^y$, —NCO, —N$_3$, —OR$^4$, —OC(O)N(R$^y$)$_2$, —N(R$^y$)$_2$, —NR$^y$C(O)R$^y$, or —NR$^y$C(O)OR$^y$; or an optionally substituted group selected from the group consisting of:

C$_{1-20}$ aliphatic;

C$_{1-20}$ heteroaliphatic having 1-4 heteroatoms independently selected from the group consisting of nitrogen, oxygen, and sulfur;

6- to 10-membered aryl;

5- to 10-membered heteroaryl having 1-4 heteroatoms independently selected from the group consisting of nitrogen, oxygen, and sulfur; and 4- to 7-membered heterocyclic having 1-2 heteroatoms independently selected from the group consisting of nitrogen, oxygen, and sulfur, or wherein two or more adjacent R$^{1'}$, R$^{2'}$, R$^{3'}$, and R$^{4'}$ groups are taken together to form an optionally substituted saturated, partially unsaturated, or aromatic 5- to 12-membered ring containing 0 to 4 heteroatoms; and So is an optionally present coordinated solvent molecule.

24. The catalyst of claim 1, wherein the metal complex has a structure selected from the group consisting of:

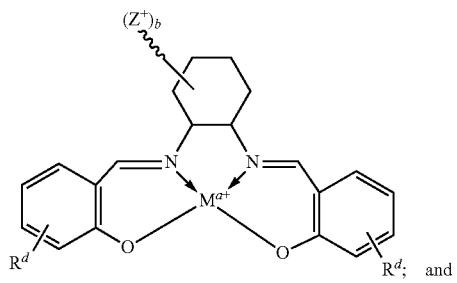

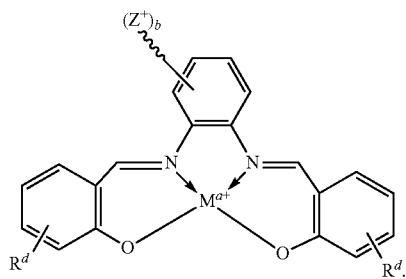

25. The catalyst of claim 1, wherein q is 3.

26. The catalyst of claim 1, wherein Z$^+$ comprises an atom selected from the group consisting of nitrogen and phosphorous.

27. The catalyst of claim 23, wherein the coordinated solvent molecule is an ether, an epoxide, DMSO, an amine, or other Lewis basic moiety.

28. A method comprising contacting ethylene oxide with carbon monoxide in the presence of a catalyst of claim 17, to provide a product comprising beta propiolactone, succinic anhydride, or polypropiolactone, or a mixture of any two or more of these.

29. The method of claim 28, wherein the product comprises beta propiolactone.

30. The method claim 28, wherein the product comprises polypropiolactone.

* * * * *